US011938180B2

(12) United States Patent
Macadam

(10) Patent No.: US 11,938,180 B2
(45) Date of Patent: Mar. 26, 2024

(54) POLIOVACCINE

(71) Applicant: Secretary of State for Health and Social Care, London (GB)

(72) Inventor: Andrew Macadam, South Mimms (GB)

(73) Assignee: SECRETARY OF STATE FOR HEALTH AND SOCIAL CARE, MINISTERIAL CORRESPONDENCE AND PUBLIC ENQUIRIES, DEPARTMENT OF HEALTH AND SOCIAL CARE, London (GB)

( * ) Notice: Subject to any disclaimer, the term of this patent is extended or adjusted under 35 U.S.C. 154(b) by 471 days.

(21) Appl. No.: 16/478,453

(22) PCT Filed: Jan. 17, 2018

(86) PCT No.: PCT/GB2018/050129
§ 371 (c)(1),
(2) Date: Jul. 16, 2019

(87) PCT Pub. No.: WO2018/134584
PCT Pub. Date: Jul. 26, 2018

(65) Prior Publication Data

US 2019/0358315 A1 Nov. 28, 2019

(30) Foreign Application Priority Data

Jan. 17, 2017 (GB) ...................................... 1700825

(51) Int. Cl.

| | |
|---|---|
| ***A61K 39/13*** | (2006.01) |
| ***A61K 39/00*** | (2006.01) |
| ***C12N 7/00*** | (2006.01) |

(52) U.S. Cl.
CPC ................ *A61K 39/13* (2013.01); *C12N 7/00* (2013.01); *A61K 2039/5258* (2013.01);
(Continued)

(58) Field of Classification Search
None
See application file for complete search history.

(56) References Cited

U.S. PATENT DOCUMENTS 11,058,760 B2 * 7/2021 Flanegan ............. C07K 14/105

FOREIGN PATENT DOCUMENTS

| | | |
|---|---|---|
| EP | 0508783 A1 | 10/1992 |
| WO | 2015/193324 A1 | 12/2015 |
| WO | 2017/184655 A1 | 10/2017 |

OTHER PUBLICATIONS

Minor PD et al. The temperature sensitivity of the Sabin type 3 vaccine strain of poliovirus: molecular and structural effects of a mutation in the capsid protein VP3. J.Gen. Virol. 1989;70:1117-1123. (Year: 1989).*

(Continued)

*Primary Examiner* — Michelle S Horning
(74) *Attorney, Agent, or Firm* — Kilpatrick Townsend & Stockton LLP

(57) ABSTRACT

The invention provides poliovirus like particles, which comprise stabilised empty poliovirus capsids that retain their native antigenic properties. The invention also provides methods of identifying mutations useful in the production of such poliovirus like particles, methods of producing such poliovirus like particles and the use of such poliovirus like particles in methods of vaccinating against poliovirus.

11 Claims, 10 Drawing Sheets

Specification includes a Sequence Listing.

(52) U.S. Cl.
CPC .................... *A61K 2039/53* (2013.01); *C12N 2770/32623* (2013.01); *C12N 2770/32634* (2013.01)

(56) References Cited

OTHER PUBLICATIONS

Macadam AJ, Ferguson G, Stone DM, Meredith J, Knowlson S, Auda G, Almond JW, Minor PD. Rational design of genetically stable, live-attenuated poliovirus vaccines of all three serotypes: relevance to poliomyelitis eradication. J Virol. Sep. 2006;80(17):8653-63. (Year: 2006).*

Pelletier et al. Characterization of the poliovirus 147S particle: new insights into poliovirus uncoating. Virology. Jan. 5, 2003;305(1):55-65.

Office Action in CN 2018800018370.4, dated Nov. 3, 2022, 9 pages.

Office Action in CN201880018370.4, dated May 17, 2023, 5, pages.

Decision of Refusal dated Jul. 3, 2023 in Japanese Application No. JP2019-559410, 2 pages.

International Search Report in PCT/GB2018/050129, dated Jun. 19, 2018.

Ansardi, et al. "Poliovirus capsid proteins derived from P1 precursors with glutamine-valine cleavage sites have defects in assembly and RNA encapsidation." Journal of virology 67, No. 12 (1993): 7284-7297.

Fox, et al. "Genetically thermo-stabilised, immunogenic poliovirus empty capsids; a strategy for non-replicating vaccines." PLoS pathogens 13, No. 1 (2017): e1006117.

John Innes Centre: "Plant-based vaccine among front runners in search for new polio jab" Jun. 10, 2016, XP055481324, retrieved from the Internet: https://www.jic.ac.uk/news-ad-events/news/2016/06/plant-based-vaccine-among-front-runners-search-new-polio-jab/ (retrieved Jun. 5, 2018).

Macadam, et al. "Reversion of the attenuated and temperature-sensitive phenotypes of the Sabin type 3 strain of poliovirus in vaccinees." Virology 172, No. 2 (1989): 408-414.

Macadam, et al. "An assembly defect as a result of an attenuating mutation in the capsid proteins of the poliovirus type 3 vaccine strain." Journal of virology 65, No. 10 (1991): 5225-5231.

Marsian, "Transient expression of poliovirus-like particles in plants. Developing a synthetic polio vaccine." PhD diss., University of East Anglia, 2016.

Marsian, et al. "Plant-made polio type 3 stabilized VLPs—a candidate synthetic polio vaccine." Nature communications 8, No. 1 (2017): 245.

Minor, et al. "The temperature sensitivity of the Sabin type 3 vaccine strain of poliovirus: molecular and structural effects of a mutation in the capsid protein VP3." Journal of General Virology 70, No. 5 (1989): 1117-1123.

Oluwapelumi et al. "Increasing type 1 poliovirus capsid stability by thermal selection." Journal of virology 91, No. 4 (2017): e01586-16.

Shiomi, et al. "Isolation and characterisation of poliovirus mutants resistant to heating at 50 c for 30 min." Journal of medical virology 74, No. 3 (2004): 484-491.

* cited by examiner

Figure 1

```
                  10        20        30        40        50
           ....|....|....|....|....|....|....|....|....|....|
Mahoney P1 MGAQVSSQKVGAHENSNRAYGGSTINYTTINYYRDSASNAASKQDFSQDP
Sabin 1 P1 ..................................................
MEF     P1 ..............................................A...
Sabin 2 P1 ..............................................A...
Saukett P1 .................................K...........Y....
Sabin 3 P1 .................................K...........Y....

                  60        70        80        90       100
           ....|....|....|....|....|....|....|....|....|....|
Mahoney P1 SKFTEPIKDVLIKTAPMLNSPNIEACGYSDRVLQLTLGNSTITTQEAANS
Sabin 1 P1 ..............S...................................
MEF     P1 ................T...............M.................
Sabin 2 P1 ................................M.................
Saukett P1 ......L.........T.....V...........................
Sabin 3 P1 ......L.........A.....V...........................

                 110       120       130       140       150
           ....|....|....|....|....|....|....|....|....|....|
Mahoney P1 VVAYGRWPEYLRDSEANPVDQPTEPDVAACRFYTLDTVSWTKESRGWWWK
Sabin 1 P1 ..................................................
MEF     P1 ..........IK..........................T.R.........
Sabin 2 P1 ..........I..T........................T.R.........
Saukett P1 .........FI..D..............T.........M.G...K.....
Sabin 3 P1 .........FI..D..............T.........M.G...K.....

                 160       170       180       190       200
           ....|....|....|....|....|....|....|....|....|....|
Mahoney P1 LPDALRDMGLFGQNMYYHYLGRSGYTVHVQCNASKFHQGALGVFAVPEMC
Sabin 1 P1 ..................................................
MEF     P1 .....K.........F......A...........................
Sabin 2 P1 .....K.........F......A...........................
Saukett P1 .............................................I..Y.
Sabin 3 P1 .............................................I..Y.

                 210       220       230       240       250
           ....|....|....|....|....|....|....|....|....|....|
Mahoney P1 LAGDSNTTTMHTSYQNANPGEKGGTFTGTFTPDNNQTSPARRFCPVDYLL
Sabin 1 P1 .................................D...............F
MEF     P1 .....-..H.F.K.E.........E.K.S..L.T.A.N...N.......F
Sabin 2 P1 .....-..H.F.K.E.........E.K.S..L.T.A.N...N.......F
Saukett P1 .....-DKQRY...A.........K.YSQ.NR.TAV...K.E........
Sabin 3 P1 .....-DKQRY...A......R..K.YSQ.NK..AV...K.E........

                 260       270       280       290       300
           ....|....|....|....|....|....|....|....|....|....|
Mahoney P1 GNGTLLGNAFVFPHQIINLRTNNCATLVLPYVNSLSIDSMVKHNNWGIAI
Sabin 1 P1 ..................................................
MEF     P1 .S.V.A.....Y............................T.........
Sabin 2 P1 .S.V.V.....Y............................T.........
Saukett P1 .C.V.......Y...........S..I......A.A..............
Sabin 3 P1 .C.V.......Y...........S..I......A.A..............
```

Figure 1 (continued)

```
                       310       320       330       340       350
                  ....|....|....|....|....|....|....|....|....|....|
Mahoney P1        LPLAPLNFASESSPEIPITLTIAPMCCEFNGLRNITLPRLQGLPVMNTPG
Sabin 1 P1        ..................................................
MEF     P1        ......D..T...T......................V..T.....L....
Sabin 2 P1        ......D..T...T......................V..T.....L....
Saukett P1        ...S..D..QD..V.....V......S.......V.A.KF.....L....
Sabin 3 P1        ...S..D..QD..V.....V......S.......V.A.KF.....L....

                       360       370       380       390       400
                  ....|....|....|....|....|....|....|....|....|....|
Mahoney P1        SNQYLTADNFQSPCALPEFDVTPPIDIPGEVKNMMELAEIDTMIPFDLSA
Sabin 1 P1        ..................................................
MEF     P1        .........Y.....I...............R.............LN.TN
Sabin 2 P1        .........Y.....I...............R.............LN.TS
Saukett P1        ......S..H.....I.............................LN.EN
Sabin 3 P1        ......S..H.....I.............................LN.ES

                       410       420       430       440       450
                  ....|....|....|....|....|....|....|....|....|....|
Mahoney P1        TKKNTMEMYRVRLSDKPHTDDPILCLSLSPASDPRLSHTMLGEILNYYTH
Sabin 1 P1        K.................................................
MEF     P1        QR....D....E.N.AA.S.T...............A.............
Sabin 2 P1        QR....D....E...TA.S.T...............A.............
Saukett P1        ..R...D....T...SADLSQ......................V......
Sabin 3 P1        ..R...D....T...SADLSQ..........F...........V......

                       460       470       480       490       500
                  ....|....|....|....|....|....|....|....|....|....|
Mahoney P1        WAGSLKFTFLFCGSMMATGKLLVSYAPPGADPPKKRKEAMLGTHVIWDIG
Sabin 1 P1        ..................................................
MEF     P1        ..............................EA..S...............
Sabin 2 P1        ..............................EA..S...............
Saukett P1        ....................I..A......Q..TS.............L.
Sabin 3 P1        ....................I..A......Q..TS.............L.

                       510       520       530       540       550
                  ....|....|....|....|....|....|....|....|....|....|
Mahoney P1        LQSSCTMVVPWISNTTYRQTIDDSFTEGGYISVFYQTRIVVPLSTPREMD
Sabin 1 P1        ..................................................
MEF     P1        .....................N..........M.....V........K..
Sabin 2 P1        .....................N..........M.....V........K..
Saukett P1        ..............V.....TQ..........M.............KS.S
Sabin 3 P1        ..............V.....TQ..........M.............KS.S

                       560       570       580       590       600
                  ....|....|....|....|....|....|....|....|....|....|
Mahoney P1        ILGFVSACNDFSVRLLRDTTHIEQKALAQGLGQMLESMIDNTVRETVGAA
Sabin 1 P1        ...............M..................................
MEF     P1        ......................S.E.MP....DLI.GVVEGVT.NALTPL
Sabin 2 P1        ......................S.E.MP..I.D.I.GAVEGITKNALVPP
Saukett P1        M.....................S.S..P..IEDLITEVAQGAL--.LSLP
Sabin 3 P1        M.....................S.S..P..IEDLISEVAQGAL--.LSLP
```

Figure 1 (continued)

```
                    610       620       630       640       650
            ....|....|....|....|....|....|....|....|....|....|
Mahoney P1  TSRDALPNTEASGPTHSKEIPALTAVETGATNPLVPSDTVQTRHVVQHRS
Sabin 1 P1  ..............A...................................
MEF     P1  .PANN..D.QS...A....T.........................I.K.T
Sabin 2 P1  ..TNS..D.KP...A..............................I.R.T
Saukett P1  KQQ.S..D.K....A....V.........................I.R..
Sabin 3 P1  KQQ.S..D.K....A....V..............A............R..

                    660       670       680       690       700
            ....|....|....|....|....|....|....|....|....|....|
Mahoney P1  RSESSIESFFARGACVTIMTVDNPASTTNKDKLFAVWKITYKDTVQLRRK
Sabin 1 P1  ................A.I....S...K......T...............
MEF     P1  ....TV..........A.IE...D.P.KRAS...S...............
Sabin 2 P1  ....TV..........A.IE...D.P.KRASR..S...............
Saukett P1  ....T...........A.IE...EEP..RAQ....T.R............
Sabin 3 P1  ....T...........A.IE...EQP..RAQ....M.R............

                    710       720       730       740       750
            ....|....|....|....|....|....|....|....|....|....|
Mahoney P1  LEFFTYSRFDMELTFVVTANFTETNNGHALNQVYQIMYVPPGAPVPEKWD
Sabin 1 P1  ............F.....................................
MEF     P1  ............F.....S.Y.DA..............I.....I.G..N
Sabin 2 P1  ............F.....S.YIDA..............I.....I.G..N
Saukett P1  ............F.........N...............I.....T.KS..
Sabin 3 P1  ............F.........NA..............I.....T.KS..

                    760       770       780       790       800
            ....|....|....|....|....|....|....|....|....|....|
Mahoney P1  DYTWQTSSNPSIFYTYGTAPARISVPYVGISNAYSHFYDGFSKVPLKDQS
Sabin 1 P1  ..................................................
MEF     P1  ...........V.....AP...........A..........A....AG.A
Sabin 2 P1  ...........V.....AP...........A..........A....AG.A
Saukett P1  .................A...........LA..........A.....TDA
Sabin 3 P1  .................A...........LA..........A.....TDA

                    810       820       830       840       850
            ....|....|....|....|....|....|....|....|....|....|
Mahoney P1  -AALGDSLYGAASLNDFGILAVRVVNDHNPTKVTSKIRVYLKPKHIRVWC
Sabin 1 P1  -.................................................
MEF     P1  -STE..............S.............L.......M....V....
Sabin 2 P1  -STE..............S............RL.......M....V....
Saukett P1  NDQI.....S.MTVD...V..I..............V.I.M....V....
Sabin 3 P1  NDQI.....S.MTVD...V.................V.I.M....V....

                    860       870       880
            ....|....|....|....|....|....|..
Mahoney P1  PRPPRAVAYYGPGVDYKDGTLTPLSTKDLTTY
Sabin 1 P1  ................................
MEF     P1  .......P...........-.A..PE.G....
Sabin 2 P1  .......P.F.........-....PE.G....
Saukett P1  .......P..........N-.N...E.G....
Sabin 3 P1  .......P........RNN-.D...E.G....
```

Figure 4
A
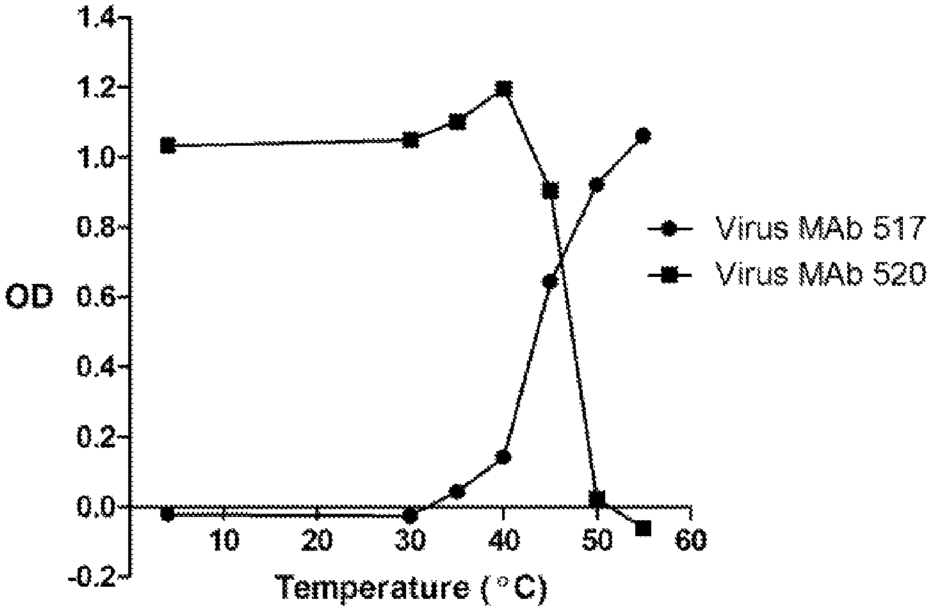
B
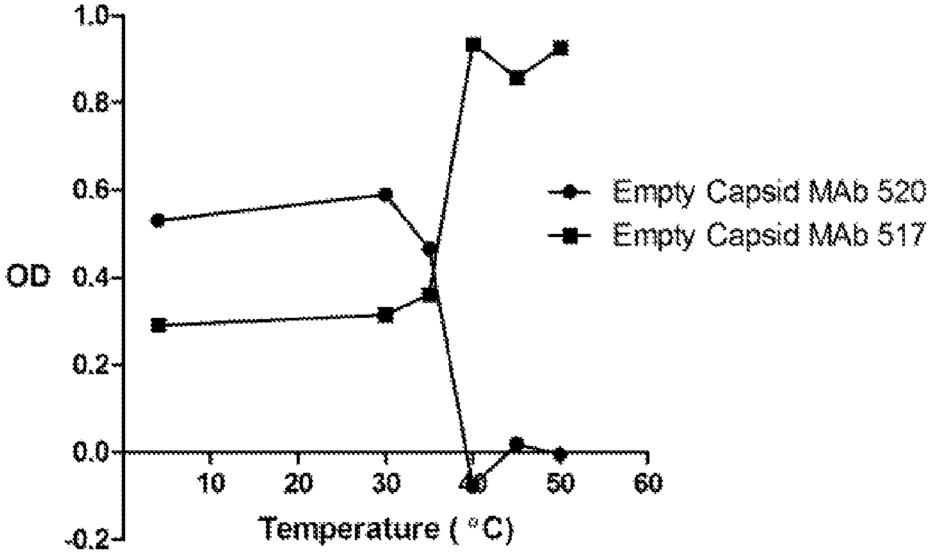

Figure 5
A
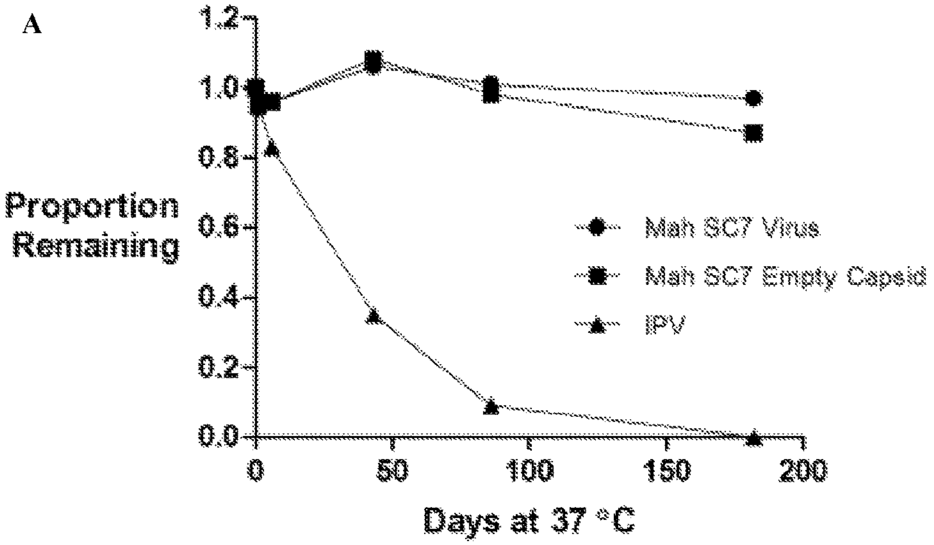
B
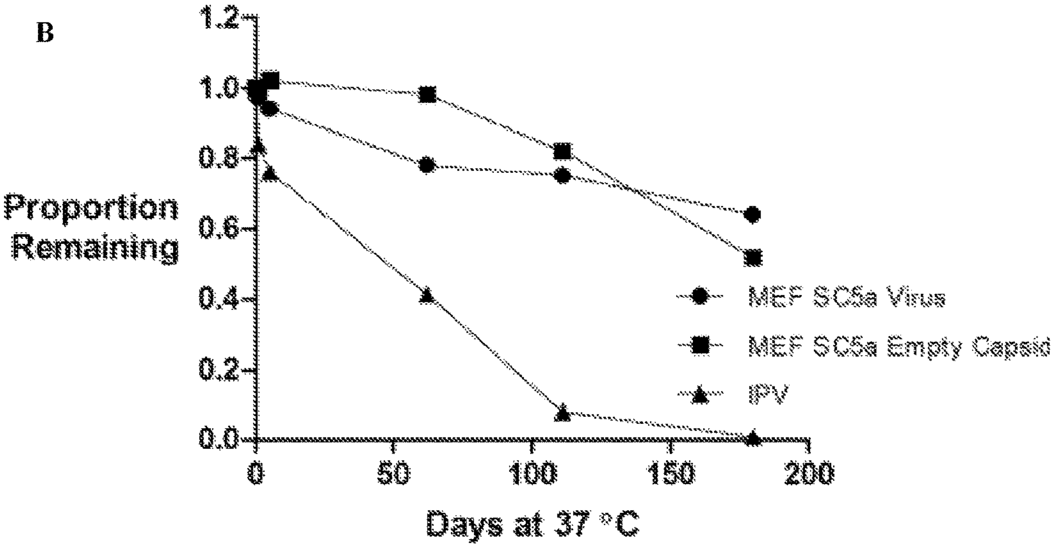
C
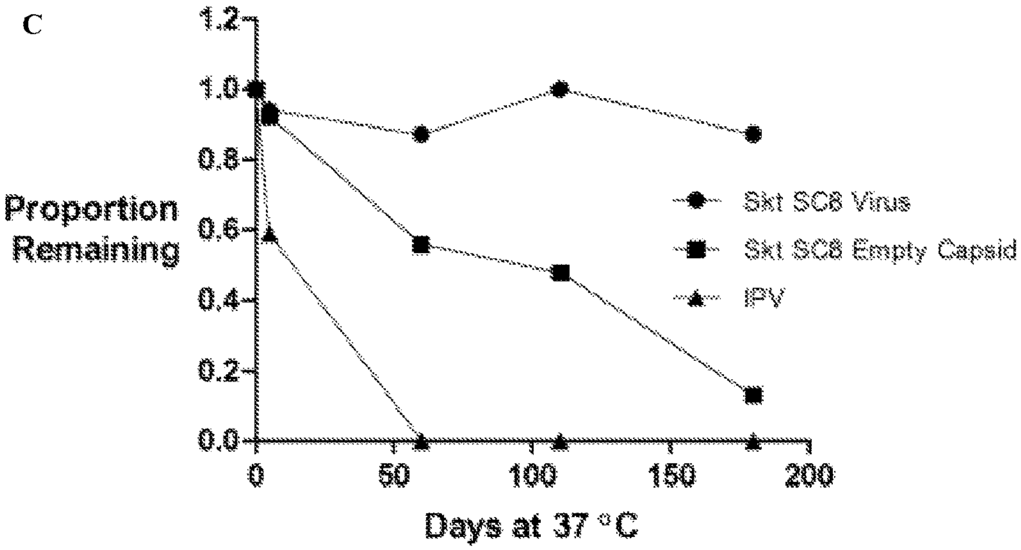

Figure 6
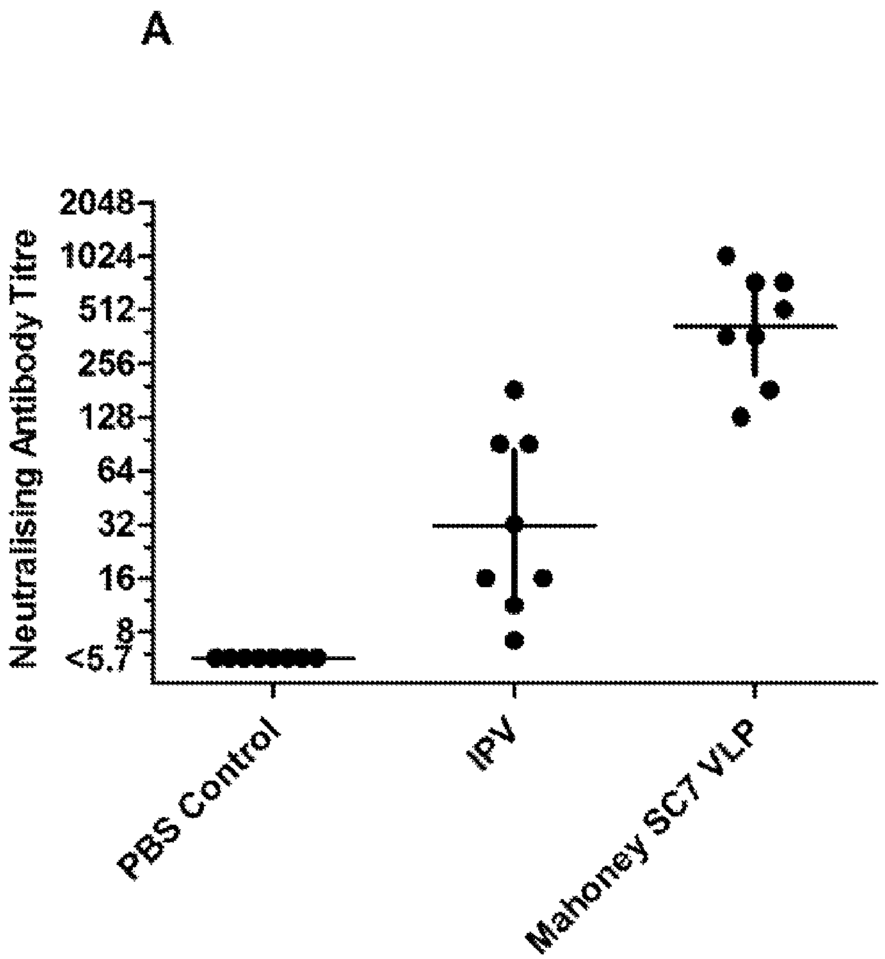
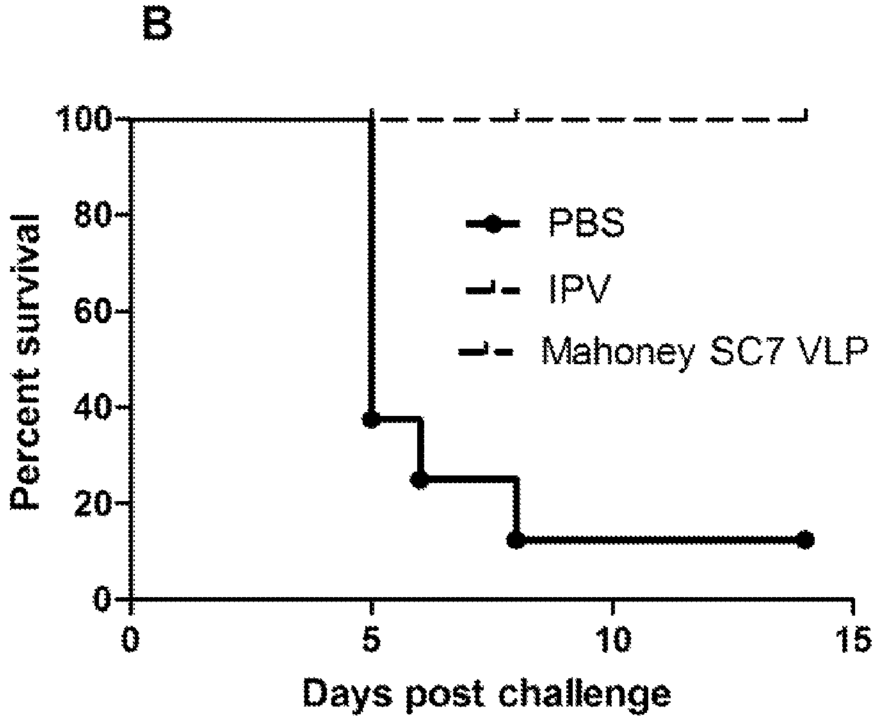

SEQUENCE LISTING

<160> NUMBER OF SEQ ID NOS: 23

<210> SEQ ID NO 1
<211> LENGTH: 302
<212> TYPE: PRT
<213> ORGANISM: Poliovirus

<400> SEQUENCE: 1

```
Gly Leu Gly Gln Met Leu Glu Ser Met Ile Asp Asn Thr Val Arg Glu
1               5                   10                  15

Thr Val Gly Ala Ala Thr Ser Arg Asp Ala Leu Pro Asn Thr Glu Ala
            20                  25                  30

Ser Gly Pro Thr His Ser Lys Glu Ile Pro Ala Leu Thr Ala Val Glu
        35                  40                  45

Thr Gly Ala Thr Asn Pro Leu Val Pro Ser Asp Thr Val Gln Thr Arg
    50                  55                  60

His Val Val Gln His Arg Ser Arg Ser Glu Ser Ser Ile Glu Ser Phe
65                  70                  75                  80

Phe Ala Arg Gly Ala Cys Val Thr Ile Met Thr Val Asp Asn Pro Ala
                85                  90                  95

Ser Thr Thr Asn Lys Asp Lys Leu Phe Ala Val Trp Lys Ile Thr Tyr
            100                 105                 110

Lys Asp Thr Val Gln Leu Arg Arg Lys Leu Glu Phe Phe Thr Tyr Ser
        115                 120                 125

Arg Phe Asp Met Glu Leu Thr Phe Val Val Thr Ala Asn Phe Thr Glu
    130                 135                 140

Thr Asn Asn Gly His Ala Leu Asn Gln Val Tyr Gln Ile Met Tyr Val
145                 150                 155                 160

Pro Pro Gly Ala Pro Val Pro Glu Lys Trp Asp Asp Tyr Thr Trp Gln
                165                 170                 175

Thr Ser Ser Asn Pro Ser Ile Phe Tyr Thr Tyr Gly Thr Ala Pro Ala
            180                 185                 190

Arg Ile Ser Val Pro Tyr Val Gly Ile Ser Asn Ala Tyr Ser His Phe
        195                 200                 205

Tyr Asp Gly Phe Ser Lys Val Pro Leu Lys Asp Gln Ser Ala Ala Leu
    210                 215                 220

Gly Asp Ser Leu Tyr Gly Ala Ala Ser Leu Asn Asp Phe Gly Ile Leu
225                 230                 235                 240

Ala Val Arg Val Val Asn Asp His Asn Pro Thr Lys Val Thr Ser Lys
                245                 250                 255

Ile Arg Val Tyr Leu Lys Pro Lys His Ile Arg Val Trp Cys Pro Arg
            260                 265                 270

Pro Pro Arg Gln Leu Ala Tyr Tyr Gly Pro Gly Val Asp Tyr Lys Asp
        275                 280                 285

Gly Thr Leu Thr Pro Leu Ser Thr Lys Asp Leu Thr Thr Tyr
    290                 295                 300
```

<210> SEQ ID NO 2
<211> LENGTH: 271
<212> TYPE: PRT
<213> ORGANISM: Poliovirus

<400> SEQUENCE: 2

```
Ser Pro Asn Ile Glu Ala Cys Gly Tyr Ser Asp Arg Val Leu Gln Leu
1               5                   10                  15

Thr Leu Gly Asn Ser Thr Ile Thr Thr Gln Glu Ala Ala Asn Ser Val
```

-continued

```
            20                  25                  30

Val Ala Tyr Gly Arg Trp Pro Glu Tyr Leu Arg Asp Ser Glu Ala Asn
        35                  40                  45

Pro Val Asp Gln Pro Thr Glu Pro Asp Val Ala Ala Cys Arg Phe Tyr
    50                  55                  60

Thr Leu Asp Thr Val Ser Trp Thr Lys Glu Ser Arg Gly Trp Trp Trp
65                  70                  75                  80

Lys Leu Pro Asp Ala Leu Arg Asp Met Gly Leu Phe Gly Gln Asn Met
                85                  90                  95

Tyr Tyr His Tyr Leu Gly Arg Ser Gly Tyr Thr Val His Val Gln Cys
            100                 105                 110

Asn Ala Ser Lys Phe His Gln Gly Ala Leu Gly Val Phe Ala Val Pro
        115                 120                 125

Glu Met Cys Leu Ala Gly Asp Ser Asn Thr Thr Thr Met His Thr Ser
    130                 135                 140

Tyr Gln Asn Ala Asn Pro Gly Glu Lys Gly Gly Thr Phe Thr Gly Thr
145                 150                 155                 160

Phe Thr Pro Asp Asn Asn Gln Thr Ser Pro Ala Arg Ser Ser Ala Arg
                165                 170                 175

Trp Ile Thr Ser Leu Glu Met Ala Arg Cys Trp Gly Met Pro Leu Cys
            180                 185                 190

Ser Ala Gln Ile Ile Asn Leu Arg Thr Asn Asn Cys Ala Thr Leu Val
        195                 200                 205

Leu Pro Tyr Val Asn Ser Leu Ser Leu Asp Ser Met Val Lys His Asn
    210                 215                 220

Asn Trp Gly Ile Ala Ile Leu Pro Leu Ala Pro Leu Asn Phe Val Ser
225                 230                 235                 240

Glu Ser Ser Pro Glu Ile Pro Ile Thr Leu Thr Ile Ala Pro Met Cys
                245                 250                 255

Cys Glu Phe Asn Gly Leu Arg Asn Ile Thr Leu Pro Arg Leu Gln
            260                 265                 270


<210> SEQ ID NO 3
<211> LENGTH: 237
<212> TYPE: PRT
<213> ORGANISM: Poliovirus

<400> SEQUENCE: 3

Gly Leu Pro Val Met Asn Thr Pro Gly Ser Asn Gln Tyr Leu Thr Ala
1               5                   10                  15

Asp Asn Phe Gln Ser Pro Cys Ala Leu Pro Glu Phe Asp Val Thr Pro
            20                  25                  30

Pro Ile Asp Ile Pro Gly Glu Val Lys Asn Met Met Leu Ala Glu Ile
        35                  40                  45

Asp Thr Met Ile Pro Phe Asp Leu Ser Ala Thr Lys Lys Asn Thr Met
    50                  55                  60

Glu Met Tyr Arg Val Arg Leu Ser Asp Lys Pro His Thr Ala Ala Ser
65                  70                  75                  80

Ile Leu Cys Leu Ser Leu Ser Pro Ala Ser Asp Pro Arg Leu Ser His
                85                  90                  95

Thr Met Leu Gly Glu Ile Leu Asn Tyr Tyr Thr His Trp Ala Gly Ser
            100                 105                 110

Leu Lys Phe Thr Phe Leu Phe Cys Gly Ser Met Met Ala Thr Gly Lys
        115                 120                 125
```

-continued

```
Leu Leu Val Ser Tyr Ala Pro Pro Gly Ala Asp Pro Pro Lys Lys Arg
    130                 135                 140

Lys Glu Ala Met Leu Gly Thr His Val Ile Trp Asp Ile Gly Leu Gln
145                 150                 155                 160

Ser Ser Cys Thr Met Val Val Pro Trp Ile Ser Asn Ser Thr Tyr Arg
                165                 170                 175

Gln Thr Ile Asp Asp Ser Phe Thr Glu Gly Gly Tyr Ile Ser Val Phe
            180                 185                 190

Tyr Gln Thr Arg Ile Val Val Pro Leu Ser Thr Pro Arg Glu Met Asp
        195                 200                 205

Ile Leu Gly Phe Val Ser Ala Cys Asn Asp Phe Ser Val Arg Leu Leu
    210                 215                 220

Arg Asp Thr Thr His Ile Glu Gln Lys Ala Leu Ala Gln
225                 230                 235


<210> SEQ ID NO 4
<211> LENGTH: 68
<212> TYPE: PRT
<213> ORGANISM: Poliovirus

<400> SEQUENCE: 4

Gly Ala Gln Val Ser Ser Gln Lys Val Gly Ala His Glu Asn Ser Asn
1               5                   10                  15

Arg Ala Tyr Gly Gly Ser Thr Ile Asn Tyr Thr Thr Ile Asn Tyr Tyr
            20                  25                  30

Arg Asp Ser Ala Ser Asn Ala Ala Ser Lys Gln Asp Phe Ser Gln Asp
        35                  40                  45

Pro Ser Lys Phe Thr Glu Pro Ile Lys Asp Val Leu Ile Lys Thr Ala
    50                  55                  60

Pro Met Leu Asn
65


<210> SEQ ID NO 5
<211> LENGTH: 339
<212> TYPE: PRT
<213> ORGANISM: Poliovirus

<400> SEQUENCE: 5

Gly Ala Gln Val Ser Ser Gln Lys Val Gly Ala His Glu Asn Ser Asn
1               5                   10                  15

Arg Ala Tyr Gly Gly Ser Thr Ile Asn Tyr Thr Thr Ile Asn Tyr Tyr
            20                  25                  30

Arg Asp Ser Ala Ser Asn Ala Ala Ser Lys Gln Asp Phe Ser Gln Asp
        35                  40                  45

Pro Ser Lys Phe Thr Glu Pro Ile Lys Asp Val Leu Ile Lys Thr Ala
    50                  55                  60

Pro Met Leu Asn Ser Pro Asn Ile Glu Ala Cys Gly Tyr Ser Asp Arg
65                  70                  75                  80

Val Leu Gln Leu Thr Leu Gly Asn Ser Thr Ile Thr Thr Gln Glu Ala
                85                  90                  95

Ala Asn Ser Val Val Ala Tyr Gly Arg Trp Pro Glu Tyr Leu Arg Asp
            100                 105                 110

Ser Glu Ala Asn Pro Val Asp Gln Pro Thr Glu Pro Asp Val Ala Ala
        115                 120                 125

Cys Arg Phe Tyr Thr Leu Asp Thr Val Ser Trp Thr Lys Glu Ser Arg
    130                 135                 140
```

-continued

```
Gly Trp Trp Trp Lys Leu Pro Asp Ala Leu Arg Asp Met Gly Leu Phe
145                 150                 155                 160

Gly Gln Asn Met Tyr Tyr His Tyr Leu Gly Arg Ser Gly Tyr Thr Val
                165                 170                 175

His Val Gln Cys Asn Ala Ser Lys Phe His Gln Gly Ala Leu Gly Val
            180                 185                 190

Phe Ala Val Pro Glu Met Cys Leu Ala Gly Asp Ser Asn Thr Thr Thr
        195                 200                 205

Met His Thr Ser Tyr Gln Asn Ala Asn Pro Gly Glu Lys Gly Gly Thr
    210                 215                 220

Phe Thr Gly Thr Phe Thr Pro Asp Asn Asn Gln Thr Ser Pro Ala Arg
225                 230                 235                 240

Ser Ser Ala Arg Trp Ile Thr Ser Leu Glu Met Ala Arg Cys Trp Gly
                245                 250                 255

Met Pro Leu Cys Ser Ala Gln Ile Ile Asn Leu Arg Thr Asn Asn Cys
            260                 265                 270

Ala Thr Leu Val Leu Pro Tyr Val Asn Ser Leu Ser Leu Asp Ser Met
        275                 280                 285

Val Lys His Asn Asn Trp Gly Ile Ala Ile Leu Pro Leu Ala Pro Leu
    290                 295                 300

Asn Phe Val Ser Glu Ser Ser Pro Glu Ile Pro Ile Thr Leu Thr Ile
305                 310                 315                 320

Ala Pro Met Cys Cys Glu Phe Asn Gly Leu Arg Asn Ile Thr Leu Pro
                325                 330                 335

Arg Leu Gln


<210> SEQ ID NO 6
<211> LENGTH: 301
<212> TYPE: PRT
<213> ORGANISM: Poliovirus

<400> SEQUENCE: 6

Gly Leu Gly Asp Leu Ile Glu Gly Val Val Glu Gly Val Thr Arg Asn
1               5                   10                  15

Ala Leu Thr Pro Leu Thr Pro Ala Asn Asn Leu Pro Asp Thr Gln Ser
            20                  25                  30

Ser Gly Pro Ala His Ser Lys Glu Thr Pro Ala Leu Thr Ala Val Glu
        35                  40                  45

Thr Gly Ala Thr Asn Pro Leu Val Pro Ser Asp Thr Val Gln Thr Arg
    50                  55                  60

His Val Ile Gln Lys Arg Thr Arg Ser Glu Ser Thr Val Glu Ser Phe
65                  70                  75                  80

Phe Ala Arg Gly Ala Cys Val Ala Ile Ile Glu Val Asp Asn Asp Ala
                85                  90                  95

Pro Thr Lys Arg Ala Ser Lys Leu Phe Ser Val Trp Lys Ile Thr Tyr
            100                 105                 110

Lys Asp Thr Val Gln Leu Arg Arg Lys Leu Glu Phe Phe Thr Tyr Ser
        115                 120                 125

Arg Phe Asp Met Glu Phe Thr Phe Val Val Thr Ser Asn Tyr Thr Asp
    130                 135                 140

Ala Asn Asn Gly His Ala Leu Asn Gln Val Tyr Gln Ile Met Tyr Ile
145                 150                 155                 160

Pro Pro Gly Ala Pro Ile Pro Gly Lys Trp Asn Asp Tyr Thr Trp Gln
                165                 170                 175
```

```
Thr Ser Ser Asn Pro Ser Val Phe Tyr Thr Tyr Gly Ala Pro Pro Ala
            180                 185                 190

Arg Ile Ser Val Pro Tyr Val Gly Ile Ala Asn Ala Tyr Ser His Phe
        195                 200                 205

Tyr Asp Gly Phe Ala Lys Val Pro Leu Ala Gly Gln Ala Ser Thr Glu
    210                 215                 220

Gly Asp Ser Leu Tyr Gly Ala Ala Ser Leu Asn Asp Phe Gly Ser Leu
225                 230                 235                 240

Ala Val Arg Val Val Asn Asp His Asn Pro Thr Lys Leu Thr Ser Lys
                245                 250                 255

Ile Arg Val Tyr Met Lys Pro Lys His Val Arg Val Trp Cys Pro Arg
            260                 265                 270

Pro Pro Arg Ala Val Pro Tyr Tyr Gly Pro Gly Val Asp Tyr Lys Asp
        275                 280                 285

Gly Leu Ala Pro Leu Pro Glu Lys Gly Leu Thr Thr Tyr
    290                 295                 300


<210> SEQ ID NO 7
<211> LENGTH: 271
<212> TYPE: PRT
<213> ORGANISM: Poliovirus

<400> SEQUENCE: 7

Ser Pro Asn Ile Glu Ala Cys Gly Tyr Ser Asp Arg Val Met Gln Leu
1               5                   10                  15

Thr Leu Gly Asn Ser Thr Ile Thr Thr Gln Glu Ala Ala Asn Ser Val
            20                  25                  30

Val Ala Tyr Gly Arg Trp Pro Glu Tyr Ile Lys Asp Ser Glu Ala Asn
        35                  40                  45

Pro Val Asp Gln Pro Thr Glu Pro Asp Val Ala Ala Cys Arg Phe Tyr
    50                  55                  60

Thr Leu Asp Thr Val Thr Trp Arg Lys Glu Ser Arg Gly Trp Trp Trp
65                  70                  75                  80

Lys Leu Pro Asp Ala Leu Lys Asp Met Gly Leu Phe Gly Gln Asn Met
                85                  90                  95

Phe Tyr His Tyr Leu Gly Arg Ala Gly Tyr Thr Val His Val Gln Cys
            100                 105                 110

Asn Ala Ser Lys Phe His Gln Gly Ala Leu Gly Val Phe Ala Val Pro
        115                 120                 125

Glu Met Cys Leu Ala Gly Asp Ser Thr Thr His Met Phe Thr Lys Tyr
    130                 135                 140

Glu Asn Ala Asn Pro Gly Glu Lys Gly Gly Glu Phe Lys Gly Ser Phe
145                 150                 155                 160

Thr Leu Asp Thr Asn Ala Thr Asn Pro Ala Arg Asn Phe Cys Pro Val
                165                 170                 175

Asp Tyr Leu Phe Gly Ser Gly Val Leu Ala Gly Asn Ala Phe Val Tyr
            180                 185                 190

Pro His Gln Ile Ile Asn Leu Arg Thr Asn Asn Cys Ala Thr Leu Val
        195                 200                 205

Leu Pro Tyr Val Asn Ser Leu Ser Ile Asp Ser Met Thr Lys His Asn
    210                 215                 220

Asn Trp Gly Ile Ala Ile Leu Pro Leu Ala Pro Leu Asp Phe Ala Thr
225                 230                 235                 240

Glu Ser Ser Thr Glu Ile Pro Ile Thr Leu Thr Ile Ala Pro Met Cys
                245                 250                 255
```

```
Cys Glu Phe Asn Gly Leu Arg Asn Ile Thr Val Pro Arg Thr Gln
            260                 265                 270


<210> SEQ ID NO 8
<211> LENGTH: 238
<212> TYPE: PRT
<213> ORGANISM: Poliovirus

<400> SEQUENCE: 8

Gly Leu Pro Val Leu Asn Thr Pro Gly Ser Asn Gln Tyr Leu Thr Ala
1               5                   10                  15

Asp Asn Tyr Gln Ser Pro Cys Ala Ile Pro Glu Phe Asp Val Thr Pro
            20                  25                  30

Pro Ile Asp Ile Pro Gly Glu Val Arg Asn Met Met Glu Leu Ala Glu
        35                  40                  45

Ile Asp Thr Met Ile Pro Leu Asn Leu Thr Asn Gln Arg Lys Asn Thr
    50                  55                  60

Met Asp Met Tyr Arg Val Glu Leu Asn Asp Ala Ala His Ser Asp Thr
65                  70                  75                  80

Pro Ile Leu Cys Leu Ser Leu Ser Pro Ala Ser Asp Pro Arg Leu Ala
                85                  90                  95

His Thr Met Leu Gly Glu Ile Leu Asn Tyr Tyr Thr His Trp Ala Gly
            100                 105                 110

Ser Leu Lys Phe Thr Phe Leu Phe Cys Gly Ser Met Met Ala Thr Gly
        115                 120                 125

Lys Leu Leu Val Ser Tyr Ala Pro Pro Gly Ala Glu Ala Pro Lys Ser
    130                 135                 140

Arg Lys Glu Ala Met Leu Gly Thr His Val Ile Trp Asp Ile Gly Leu
145                 150                 155                 160

Gln Ser Ser Cys Thr Met Val Val Pro Trp Ile Ser Asn Thr Thr Tyr
                165                 170                 175

Arg Gln Thr Ile Asn Asp Ser Phe Thr Glu Gly Gly Tyr Ile Ser Met
            180                 185                 190

Phe Tyr Gln Thr Arg Val Val Val Pro Leu Ser Thr Pro Arg Lys Met
        195                 200                 205

Asp Ile Leu Gly Phe Val Ser Ala Cys Asn Asp Phe Ser Val Arg Leu
    210                 215                 220

Leu Arg Asp Thr Thr His Ile Ser Gln Glu Ala Met Pro Gln
225                 230                 235


<210> SEQ ID NO 9
<211> LENGTH: 69
<212> TYPE: PRT
<213> ORGANISM: Poliovirus

<400> SEQUENCE: 9

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ala Gln
        35                  40                  45

Asp Pro Ser Lys Phe Thr Glu Pro Ile Lys Asp Val Leu Ile Lys Thr
    50                  55                  60

Ala Pro Thr Leu Asn
65
```

-continued

<210> SEQ ID NO 10
<211> LENGTH: 271
<212> TYPE: PRT
<213> ORGANISM: Poliovirus

<400> SEQUENCE: 10

```
Ser Pro Asn Ile Glu Ala Cys Gly Tyr Ser Asp Arg Val Met Gln Leu
1               5                   10                  15

Thr Leu Gly Asn Ser Thr Ile Thr Thr Gln Glu Ala Ala Asn Ser Val
            20                  25                  30

Val Ala Tyr Gly Arg Trp Pro Glu Tyr Ile Lys Asp Ser Glu Ala Asn
        35                  40                  45

Pro Val Asp Gln Pro Thr Glu Pro Asp Val Ala Ala Cys Arg Phe Tyr
    50                  55                  60

Thr Leu Asp Thr Val Thr Trp Arg Lys Glu Ser Arg Gly Trp Trp Trp
65                  70                  75                  80

Lys Leu Pro Asp Ala Leu Lys Asp Met Gly Leu Phe Gly Gln Asn Met
                85                  90                  95

Phe Tyr His Tyr Leu Gly Arg Ala Gly Tyr Thr Val His Val Gln Cys
            100                 105                 110

Asn Ala Ser Lys Phe His Gln Gly Ala Leu Gly Val Phe Ala Val Pro
        115                 120                 125

Glu Met Cys Leu Ala Gly Asp Ser Thr Thr His Met Phe Thr Lys Tyr
    130                 135                 140

Glu Asn Ala Asn Pro Gly Glu Lys Gly Gly Glu Phe Lys Gly Ser Phe
145                 150                 155                 160

Thr Leu Asp Thr Asn Ala Thr Asn Pro Ala Arg Asn Phe Cys Pro Val
                165                 170                 175

Asp Tyr Leu Phe Gly Ser Gly Val Leu Ala Gly Asn Ala Phe Val Tyr
            180                 185                 190

Pro His Gln Ile Ile Asn Leu Arg Thr Asn Asn Cys Ala Thr Leu Val
        195                 200                 205

Leu Pro Tyr Val Asn Ser Leu Ser Ile Asp Ser Met Thr Lys His Asn
    210                 215                 220

Asn Trp Gly Ile Ala Ile Leu Pro Leu Ala Pro Leu Asp Phe Ala Thr
225                 230                 235                 240

Glu Ser Ser Thr Glu Ile Pro Ile Thr Leu Thr Ile Ala Pro Met Cys
                245                 250                 255

Cys Glu Phe Asn Gly Leu Arg Asn Ile Thr Val Pro Arg Thr Gln
            260                 265                 270
```

<210> SEQ ID NO 11
<211> LENGTH: 300
<212> TYPE: PRT
<213> ORGANISM: Poliovirus

<400> SEQUENCE: 11

```
Gly Ile Glu Asp Leu Ile Thr Glu Val Ala Gln Gly Ala Leu Thr Leu
1               5                   10                  15

Ser Leu Pro Lys Gln Gln Asp Ser Leu Pro Asp Thr Lys Ala Ser Gly
            20                  25                  30

Pro Ala His Ser Lys Glu Val Pro Ala Leu Thr Ala Val Glu Thr Gly
        35                  40                  45

Ala Thr Asn Pro Leu Val Pro Ser Asp Thr Val Gln Thr Arg His Val
    50                  55                  60
```

```
Ile Gln Arg Arg Ser Arg Ser Glu Ser Thr Ile Glu Ser Phe Phe Ala
65                  70                  75                  80

Arg Gly Ala Cys Val Ala Ile Ile Glu Val Asp Asn Glu Glu Pro Thr
                85                  90                  95

Thr Arg Ala Gln Lys Leu Phe Ala Thr Trp Arg Ile Thr Tyr Lys Asp
            100                 105                 110

Thr Val Gln Leu Arg Arg Lys Leu Glu Phe Phe Thr Tyr Ser Arg Phe
        115                 120                 125

Asp Met Glu Phe Thr Phe Val Val Thr Ala Asn Phe Thr Asn Thr Asn
    130                 135                 140

Asn Gly His Ala Leu Asn Gln Val Tyr Gln Ile Met Tyr Ile Pro Pro
145                 150                 155                 160

Gly Ala Pro Thr Pro Lys Ser Trp Asp Asp Tyr Thr Trp Gln Thr Ser
                165                 170                 175

Ser Asn Pro Ser Ile Phe Tyr Thr Tyr Gly Ala Ala Pro Ala Arg Ile
            180                 185                 190

Ser Val Pro Tyr Val Gly Leu Ala Asn Ala Tyr Ser His Phe Tyr Asp
        195                 200                 205

Gly Phe Ala Lys Val Pro Leu Lys Thr Asp Ala Asn Asp Gln Ile Gly
    210                 215                 220

Asp Ser Leu Tyr Ser Ala Met Thr Val Asp Asp Phe Gly Val Leu Ala
225                 230                 235                 240

Ile Arg Val Val Asn Asp His Asn Pro Thr Lys Val Thr Ser Lys Val
                245                 250                 255

Arg Ile Tyr Met Lys Pro Lys His Val Arg Val Trp Cys Pro Arg Pro
            260                 265                 270

Pro Arg Ala Val Pro Tyr Tyr Gly Pro Gly Val Asp Tyr Lys Asp Asn
        275                 280                 285

Leu Asn Pro Leu Ser Glu Lys Gly Leu Thr Thr Tyr
    290                 295                 300


<210> SEQ ID NO 12
<211> LENGTH: 271
<212> TYPE: PRT
<213> ORGANISM: Poliovirus

<400> SEQUENCE: 12

Ser Pro Asn Val Glu Ala Cys Gly Tyr Ser Asp Arg Val Leu Gln Leu
1               5                   10                  15

Thr Leu Gly Asn Ser Thr Ile Thr Thr Gln Glu Ala Ala Asn Ser Val
            20                  25                  30

Val Ala Tyr Gly Arg Trp Pro Glu Phe Ile Arg Asp Asp Glu Ala Asn
        35                  40                  45

Pro Val Asp Gln Pro Thr Glu Pro Asp Val Ala Thr Cys Arg Phe Tyr
    50                  55                  60

Thr Leu Asp Thr Val Met Trp Gly Lys Glu Ser Lys Gly Trp Trp Trp
65                  70                  75                  80

Lys Leu Pro Asp Ala Leu Arg Asp Met Gly Leu Phe Gly Gln Asn Met
                85                  90                  95

Tyr Tyr His Tyr Leu Gly Arg Ser Gly Tyr Thr Val His Val Gln Cys
            100                 105                 110

Asn Ala Ser Lys Phe His Gln Gly Ala Leu Gly Val Phe Ala Ile Pro
        115                 120                 125

Glu Tyr Cys Leu Ala Gly Asp Ser Asp Lys Gln Arg Tyr Thr Ser Tyr
```

```
    130                 135                 140

Ala Asn Ala Asn Pro Gly Glu Lys Gly Gly Lys Phe Tyr Ser Gln Phe
145                 150                 155                 160

Asn Arg Asp Thr Ala Val Thr Ser Pro Lys Arg Glu Phe Cys Pro Val
                165                 170                 175

Asp Tyr Leu Leu Gly Cys Gly Val Leu Leu Gly Asn Ala Phe Val Tyr
            180                 185                 190

Pro His Gln Ile Ile Asn Leu Arg Thr Asn Asn Ser Ala Thr Ile Val
        195                 200                 205

Leu Pro Tyr Val Asn Ala Leu Ala Ile Asp Ser Met Val Lys His Asn
    210                 215                 220

Asn Trp Gly Ile Ala Ile Leu Pro Leu Ser Pro Leu Asp Phe Ala Gln
225                 230                 235                 240

Asp Ser Ser Val Glu Ile Pro Ile Thr Val Thr Ile Ala Pro Met Cys
                245                 250                 255

Ser Glu Phe Asn Gly Leu Arg Asn Val Thr Ala Pro Lys Phe Gln
            260                 265                 270


<210> SEQ ID NO 13
<211> LENGTH: 238
<212> TYPE: PRT
<213> ORGANISM: Poliovirus

<400> SEQUENCE: 13

Gly Leu Pro Val Leu Asn Thr Pro Gly Ser Asn Gln Tyr Leu Thr Ser
1               5                   10                  15

Asp Asn His Gln Ser Pro Cys Ala Ile Pro Glu Phe Asp Val Thr Pro
            20                  25                  30

Pro Ile Asp Ile Pro Gly Glu Val Lys Asn Met Met Glu Leu Ala Glu
        35                  40                  45

Ile Asp Thr Met Ile Pro Leu Asn Leu Glu Asn Thr Lys Arg Asn Thr
    50                  55                  60

Met Asp Met Tyr Arg Val Thr Leu Ser Asp Ser Ala Asp Leu Ser Gln
65                  70                  75                  80

Pro Ile Leu Cys Leu Ser Leu Ser Pro Ala Ser Asp Pro Arg Leu Ser
                85                  90                  95

His Thr Met Leu Gly Glu Val Leu Asn Tyr Tyr Thr His Trp Ala Gly
            100                 105                 110

Ser Leu Lys Phe Thr Phe Leu Phe Cys Gly Ser Met Met Ala Thr Gly
        115                 120                 125

Lys Ile Leu Val Ala Tyr Ala Pro Pro Gly Ala Gln Pro Pro Thr Ser
    130                 135                 140

Arg Lys Glu Ala Met Leu Gly Thr His Val Ile Trp Asp Leu Gly Leu
145                 150                 155                 160

Gln Ser Ser Cys Thr Met Val Val Pro Trp Ile Ser Asn Val Thr Tyr
                165                 170                 175

Arg Gln Thr Thr Gln Asp Ser Phe Thr Glu Gly Gly Tyr Ile Ser Met
            180                 185                 190

Phe Tyr Gln Thr Arg Ile Val Val Pro Leu Ser Thr Pro Lys Ser Met
        195                 200                 205

Ser Met Leu Gly Phe Val Ser Ala Cys Asn Asp Phe Ser Val Arg Leu
    210                 215                 220

Leu Arg Asp Thr Thr His Ile Ser Gln Ser Ala Leu Pro Gln
225                 230                 235
```

<210> SEQ ID NO 14
<211> LENGTH: 69
<212> TYPE: PRT
<213> ORGANISM: Poliovirus

<400> SEQUENCE: 14

```
Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Lys Asp Ser Ala Ser Asn Ala Ala Ser Lys Gln Asp Tyr Ser Gln
        35                  40                  45

Asp Pro Ser Lys Phe Thr Glu Pro Leu Lys Asp Val Leu Ile Lys Thr
    50                  55                  60

Ala Pro Thr Leu Asn
65
```

<210> SEQ ID NO 15
<211> LENGTH: 340
<212> TYPE: PRT
<213> ORGANISM: Poliovirus

<400> SEQUENCE: 15

```
Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Lys Asp Ser Ala Ser Asn Ala Ala Ser Lys Gln Asp Tyr Ser Gln
        35                  40                  45

Asp Pro Ser Lys Phe Thr Glu Pro Leu Lys Asp Val Leu Ile Lys Thr
    50                  55                  60

Ala Pro Thr Leu Asn Ser Pro Asn Val Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Phe Ile Arg
            100                 105                 110

Asp Asp Glu Ala Asn Pro Val Asp Gln Pro Thr Glu Pro Asp Val Ala
        115                 120                 125

Thr Cys Arg Phe Tyr Thr Leu Asp Thr Val Met Trp Gly Lys Glu Ser
    130                 135                 140

Lys Gly Trp Trp Trp Lys Leu Pro Asp Ala Leu Arg Asp Met Gly Leu
145                 150                 155                 160

Phe Gly Gln Asn Met Tyr Tyr His Tyr Leu Gly Arg Ser Gly Tyr Thr
                165                 170                 175

Val His Val Gln Cys Asn Ala Ser Lys Phe His Gln Gly Ala Leu Gly
            180                 185                 190

Val Phe Ala Ile Pro Glu Tyr Cys Leu Ala Gly Asp Ser Asp Lys Gln
        195                 200                 205

Arg Tyr Thr Ser Tyr Ala Asn Ala Asn Pro Gly Glu Lys Gly Gly Lys
    210                 215                 220

Phe Tyr Ser Gln Phe Asn Arg Asp Thr Ala Val Thr Ser Pro Lys Arg
225                 230                 235                 240

Glu Phe Cys Pro Val Asp Tyr Leu Leu Gly Cys Gly Val Leu Leu Gly
                245                 250                 255
```

-continued

```
Asn Ala Phe Val Tyr Pro His Gln Ile Ile Asn Leu Arg Thr Asn Asn
            260                 265                 270

Ser Ala Thr Ile Val Leu Pro Tyr Val Asn Ala Leu Ala Ile Asp Ser
        275                 280                 285

Met Val Lys His Asn Asn Trp Gly Ile Ala Ile Leu Pro Leu Ser Pro
    290                 295                 300

Leu Asp Phe Ala Gln Asp Ser Ser Val Glu Ile Pro Ile Thr Val Thr
305                 310                 315                 320

Ile Ala Pro Met Cys Ser Glu Phe Asn Gly Leu Arg Asn Val Thr Ala
                325                 330                 335

Pro Lys Phe Gln
            340


<210> SEQ ID NO 16
<211> LENGTH: 881
<212> TYPE: PRT
<213> ORGANISM: Poliovirus

<400> SEQUENCE: 16

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ser Gln
        35                  40                  45

Asp Pro Ser Lys Phe Thr Glu Pro Ile Lys Asp Val Leu Ile Lys Thr
    50                  55                  60

Ala Pro Met Leu Asn Ser Pro Asn Ile Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Leu Arg
            100                 105                 110

Asp Ser Glu Ala Asn Pro Val Asp Gln Pro Thr Glu Pro Asp Val Ala
        115                 120                 125

Ala Cys Arg Phe Tyr Thr Leu Asp Thr Val Ser Trp Thr Lys Glu Ser
    130                 135                 140

Arg Gly Trp Trp Trp Lys Leu Pro Asp Ala Leu Arg Asp Met Gly Leu
145                 150                 155                 160

Phe Gly Gln Asn Met Tyr Tyr His Tyr Leu Gly Arg Ser Gly Tyr Thr
                165                 170                 175

Val His Val Gln Cys Asn Ala Ser Lys Phe His Gln Gly Ala Leu Gly
            180                 185                 190

Val Phe Ala Val Pro Glu Met Cys Leu Ala Gly Asp Ser Asn Thr Thr
        195                 200                 205

Thr Met His Thr Ser Tyr Gln Asn Ala Asn Pro Gly Glu Lys Gly Gly
    210                 215                 220

Thr Phe Thr Gly Thr Phe Thr Pro Asp Asn Asn Gln Thr Ser Pro Ala
225                 230                 235                 240

Arg Arg Phe Cys Pro Val Asp Tyr Leu Leu Gly Asn Gly Thr Leu Leu
                245                 250                 255

Gly Asn Ala Phe Val Phe Pro His Gln Ile Ile Asn Leu Arg Thr Asn
            260                 265                 270

Asn Cys Ala Thr Leu Val Leu Pro Tyr Val Asn Ser Leu Ser Ile Asp
        275                 280                 285
```

-continued

```
Ser Met Val Lys His Asn Asn Trp Gly Ile Ala Ile Leu Pro Leu Ala
    290                 295                 300

Pro Leu Asn Phe Ala Ser Glu Ser Ser Pro Glu Ile Pro Ile Thr Leu
305                 310                 315                 320

Thr Ile Ala Pro Met Cys Cys Glu Phe Asn Gly Leu Arg Asn Ile Thr
                325                 330                 335

Leu Pro Arg Leu Gln Gly Leu Pro Val Met Asn Thr Pro Gly Ser Asn
            340                 345                 350

Gln Tyr Leu Thr Ala Asp Asn Phe Gln Ser Pro Cys Ala Leu Pro Glu
        355                 360                 365

Phe Asp Val Thr Pro Pro Ile Asp Ile Pro Gly Glu Val Lys Asn Met
    370                 375                 380

Met Glu Leu Ala Glu Ile Asp Thr Met Ile Pro Phe Asp Leu Ser Ala
385                 390                 395                 400

Thr Lys Lys Asn Thr Met Glu Met Tyr Arg Val Arg Leu Ser Asp Lys
                405                 410                 415

Pro His Thr Asp Asp Pro Ile Leu Cys Leu Ser Leu Ser Pro Ala Ser
            420                 425                 430

Asp Pro Arg Leu Ser His Thr Met Leu Gly Glu Ile Leu Asn Tyr Tyr
        435                 440                 445

Thr His Trp Ala Gly Ser Leu Lys Phe Thr Phe Leu Phe Cys Gly Ser
    450                 455                 460

Met Met Ala Thr Gly Lys Leu Leu Val Ser Tyr Ala Pro Pro Gly Ala
465                 470                 475                 480

Asp Pro Pro Lys Lys Arg Lys Glu Ala Met Leu Gly Thr His Val Ile
                485                 490                 495

Trp Asp Ile Gly Leu Gln Ser Ser Cys Thr Met Val Val Pro Trp Ile
            500                 505                 510

Ser Asn Thr Thr Tyr Arg Gln Thr Ile Asp Asp Ser Phe Thr Glu Gly
        515                 520                 525

Gly Tyr Ile Ser Val Phe Tyr Gln Thr Arg Ile Val Val Pro Leu Ser
    530                 535                 540

Thr Pro Arg Glu Met Asp Ile Leu Gly Phe Val Ser Ala Cys Asn Asp
545                 550                 555                 560

Phe Ser Val Arg Leu Leu Arg Asp Thr Thr His Ile Glu Gln Lys Ala
                565                 570                 575

Leu Ala Gln Gly Leu Gly Gln Met Leu Glu Ser Met Ile Asp Asn Thr
            580                 585                 590

Val Arg Glu Thr Val Gly Ala Ala Thr Ser Arg Asp Ala Leu Pro Asn
        595                 600                 605

Thr Glu Ala Ser Gly Pro Thr His Ser Lys Glu Ile Pro Ala Leu Thr
    610                 615                 620

Ala Val Glu Thr Gly Ala Thr Asn Pro Leu Val Pro Ser Asp Thr Val
625                 630                 635                 640

Gln Thr Arg His Val Val Gln His Arg Ser Arg Ser Glu Ser Ser Ile
                645                 650                 655

Glu Ser Phe Phe Ala Arg Gly Ala Cys Val Thr Ile Met Thr Val Asp
            660                 665                 670

Asn Pro Ala Ser Thr Thr Asn Lys Asp Lys Leu Phe Ala Val Trp Lys
        675                 680                 685

Ile Thr Tyr Lys Asp Thr Val Gln Leu Arg Arg Lys Leu Glu Phe Phe
    690                 695                 700
```

-continued

Thr Tyr Ser Arg Phe Asp Met Glu Leu Thr Phe Val Val Thr Ala Asn
705 710 715 720

Phe Thr Glu Thr Asn Asn Gly His Ala Leu Asn Gln Val Tyr Gln Ile
725 730 735

Met Tyr Val Pro Pro Gly Ala Pro Val Pro Glu Lys Trp Asp Asp Tyr
740 745 750

Thr Trp Gln Thr Ser Ser Asn Pro Ser Ile Phe Tyr Thr Tyr Gly Thr
755 760 765

Ala Pro Ala Arg Ile Ser Val Pro Tyr Val Gly Ile Ser Asn Ala Tyr
770 775 780

Ser His Phe Tyr Asp Gly Phe Ser Lys Val Pro Leu Lys Asp Gln Ser
785 790 795 800

Ala Ala Leu Gly Asp Ser Leu Tyr Gly Ala Ala Ser Leu Asn Asp Phe
805 810 815

Gly Ile Leu Ala Val Arg Val Val Asn Asp His Asn Pro Thr Lys Val
820 825 830

Thr Ser Lys Ile Arg Val Tyr Leu Lys Pro Lys His Ile Arg Val Trp
835 840 845

Cys Pro Arg Pro Pro Arg Ala Val Ala Tyr Tyr Gly Pro Gly Val Asp
850 855 860

Tyr Lys Asp Gly Thr Leu Thr Pro Leu Ser Thr Lys Asp Leu Thr Thr
865 870 875 880

Tyr

<210> SEQ ID NO 17
<211> LENGTH: 881
<212> TYPE: PRT
<213> ORGANISM: Poliovirus

<400> SEQUENCE: 17

Met Gly Ala Gln Val Ser Ser Gln Lys Val Gly Ala His Glu Asn Ser
1 5 10 15

Asn Arg Ala Tyr Gly Gly Ser Thr Ile Asn Tyr Thr Thr Ile Asn Tyr
20 25 30

Tyr Arg Asp Ser Ala Ser Asn Ala Ala Ser Lys Gln Asp Phe Ser Gln
35 40 45

Asp Pro Ser Lys Phe Thr Glu Pro Ile Lys Asp Val Leu Ile Lys Thr
50 55 60

Ser Pro Met Leu Asn Ser Pro Asn Ile Glu Ala Cys Gly Tyr Ser Asp
65 70 75 80

Arg Val Leu Gln Leu Thr Leu Gly Asn Ser Thr Ile Thr Thr Gln Glu
85 90 95

Ala Ala Asn Ser Val Val Ala Tyr Gly Arg Trp Pro Glu Tyr Leu Arg
100 105 110

Asp Ser Glu Ala Asn Pro Val Asp Gln Pro Thr Glu Pro Asp Val Ala
115 120 125

Ala Cys Arg Phe Tyr Thr Leu Asp Thr Val Ser Trp Thr Lys Glu Ser
130 135 140

Arg Gly Trp Trp Trp Lys Leu Pro Asp Ala Leu Arg Asp Met Gly Leu
145 150 155 160

Phe Gly Gln Asn Met Tyr Tyr His Tyr Leu Gly Arg Ser Gly Tyr Thr
165 170 175

Val His Val Gln Cys Asn Ala Ser Lys Phe His Gln Gly Ala Leu Gly
180 185 190

-continued

```
Val Phe Ala Val Pro Glu Met Cys Leu Ala Gly Asp Ser Asn Thr Thr
        195                 200                 205

Thr Met His Thr Ser Tyr Gln Asn Ala Asn Pro Gly Glu Lys Gly Gly
    210                 215                 220

Thr Phe Thr Gly Thr Phe Thr Pro Asp Asp Asn Gln Thr Ser Pro Ala
225                 230                 235                 240

Arg Arg Phe Cys Pro Val Asp Tyr Leu Phe Gly Asn Gly Thr Leu Leu
                245                 250                 255

Gly Asn Ala Phe Val Phe Pro His Gln Ile Ile Asn Leu Arg Thr Asn
            260                 265                 270

Asn Cys Ala Thr Leu Val Leu Pro Tyr Val Asn Ser Leu Ser Ile Asp
        275                 280                 285

Ser Met Val Lys His Asn Asn Trp Gly Ile Ala Ile Leu Pro Leu Ala
    290                 295                 300

Pro Leu Asn Phe Ala Ser Glu Ser Ser Pro Glu Ile Pro Ile Thr Leu
305                 310                 315                 320

Thr Ile Ala Pro Met Cys Cys Glu Phe Asn Gly Leu Arg Asn Ile Thr
                325                 330                 335

Leu Pro Arg Leu Gln Gly Leu Pro Val Met Asn Thr Pro Gly Ser Asn
            340                 345                 350

Gln Tyr Leu Thr Ala Asp Asn Phe Gln Ser Pro Cys Ala Leu Pro Glu
        355                 360                 365

Phe Asp Val Thr Pro Pro Ile Asp Ile Pro Gly Glu Val Lys Asn Met
    370                 375                 380

Met Glu Leu Ala Glu Ile Asp Thr Met Ile Pro Phe Asp Leu Ser Ala
385                 390                 395                 400

Lys Lys Lys Asn Thr Met Glu Met Tyr Arg Val Arg Leu Ser Asp Lys
                405                 410                 415

Pro His Thr Asp Asp Pro Ile Leu Cys Leu Ser Leu Ser Pro Ala Ser
            420                 425                 430

Asp Pro Arg Leu Ser His Thr Met Leu Gly Glu Ile Leu Asn Tyr Tyr
        435                 440                 445

Thr His Trp Ala Gly Ser Leu Lys Phe Thr Phe Leu Phe Cys Gly Ser
    450                 455                 460

Met Met Ala Thr Gly Lys Leu Leu Val Ser Tyr Ala Pro Pro Gly Ala
465                 470                 475                 480

Asp Pro Pro Lys Lys Arg Lys Glu Ala Met Leu Gly Thr His Val Ile
                485                 490                 495

Trp Asp Ile Gly Leu Gln Ser Ser Cys Thr Met Val Val Pro Trp Ile
            500                 505                 510

Ser Asn Thr Thr Tyr Arg Gln Thr Ile Asp Asp Ser Phe Thr Glu Gly
        515                 520                 525

Gly Tyr Ile Ser Val Phe Tyr Gln Thr Arg Ile Val Val Pro Leu Ser
    530                 535                 540

Thr Pro Arg Glu Met Asp Ile Leu Gly Phe Val Ser Ala Cys Asn Asp
545                 550                 555                 560

Phe Ser Val Arg Leu Met Arg Asp Thr Thr His Ile Glu Gln Lys Ala
                565                 570                 575

Leu Ala Gln Gly Leu Gly Gln Met Leu Glu Ser Met Ile Asp Asn Thr
            580                 585                 590

Val Arg Glu Thr Val Gly Ala Ala Thr Ser Arg Asp Ala Leu Pro Asn
        595                 600                 605

Thr Glu Ala Ser Gly Pro Ala His Ser Lys Glu Ile Pro Ala Leu Thr
```

-continued

```
    610                 615                 620

Ala Val Glu Thr Gly Ala Thr Asn Pro Leu Val Pro Ser Asp Thr Val
625                 630                 635                 640

Gln Thr Arg His Val Val Gln His Arg Ser Arg Ser Glu Ser Ser Ile
                645                 650                 655

Glu Ser Phe Phe Ala Arg Gly Ala Cys Val Ala Ile Ile Thr Val Asp
            660                 665                 670

Asn Ser Ala Ser Thr Lys Asn Lys Asp Lys Leu Phe Ala Val Trp Lys
        675                 680                 685

Ile Thr Tyr Lys Asp Thr Val Gln Leu Arg Arg Lys Leu Glu Phe Phe
    690                 695                 700

Thr Tyr Ser Arg Phe Asp Met Glu Phe Thr Phe Val Val Thr Ala Asn
705                 710                 715                 720

Phe Thr Glu Thr Asn Asn Gly His Ala Leu Asn Gln Val Tyr Gln Ile
                725                 730                 735

Met Tyr Val Pro Pro Gly Ala Pro Val Pro Glu Lys Trp Asp Asp Tyr
            740                 745                 750

Thr Trp Gln Thr Ser Ser Asn Pro Ser Ile Phe Tyr Thr Tyr Gly Thr
        755                 760                 765

Ala Pro Ala Arg Ile Ser Val Pro Tyr Val Gly Ile Ser Asn Ala Tyr
    770                 775                 780

Ser His Phe Tyr Asp Gly Phe Ser Lys Val Pro Leu Lys Asp Gln Ser
785                 790                 795                 800

Ala Ala Leu Gly Asp Ser Leu Tyr Gly Ala Ala Ser Leu Asn Asp Phe
                805                 810                 815

Gly Ile Leu Ala Val Arg Val Val Asn Asp His Asn Pro Thr Lys Val
            820                 825                 830

Thr Ser Lys Ile Arg Val Tyr Leu Lys Pro Lys His Ile Arg Val Trp
        835                 840                 845

Cys Pro Arg Pro Pro Arg Ala Val Ala Tyr Tyr Gly Pro Gly Val Asp
    850                 855                 860

Tyr Lys Asp Gly Thr Leu Thr Pro Leu Ser Thr Lys Asp Leu Thr Thr
865                 870                 875                 880

Tyr


<210> SEQ ID NO 18
<211> LENGTH: 879
<212> TYPE: PRT
<213> ORGANISM: Poliovirus

<400> SEQUENCE: 18

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ala Gln
        35                  40                  45

Asp Pro Ser Lys Phe Thr Glu Pro Ile Lys Asp Val Leu Ile Lys Thr
    50                  55                  60

Ala Pro Met Leu Asn Ser Pro Asn Ile Glu Ala Cys Gly Tyr Ser Asp
65                  70                  75                  80

Arg Val Met Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Ile Lys
```

-continued

```
            100                 105                 110

Asp Ser Glu Ala Asn Pro Val Asp Gln Pro Thr Glu Pro Asp Val Ala
        115                 120                 125

Ala Cys Arg Phe Tyr Thr Leu Asp Thr Val Thr Trp Arg Lys Glu Ser
    130                 135                 140

Arg Gly Trp Trp Trp Lys Leu Pro Asp Ala Leu Lys Asp Met Gly Leu
145                 150                 155                 160

Phe Gly Gln Asn Met Phe Tyr His Tyr Leu Gly Arg Ser Gly Tyr Thr
                165                 170                 175

Val His Val Gln Cys Asn Ala Ser Lys Phe His Gln Gly Ala Leu Gly
            180                 185                 190

Val Phe Ala Val Pro Glu Met Cys Leu Ala Gly Asp Ser Thr Thr His
        195                 200                 205

Met Phe Thr Lys Tyr Glu Asn Ala Asn Pro Gly Glu Lys Gly Gly Glu
    210                 215                 220

Phe Lys Gly Ser Phe Thr Leu Asp Thr Asn Ala Thr Asn Pro Ala Arg
225                 230                 235                 240

Asn Phe Cys Pro Val Asp Tyr Leu Phe Gly Ser Gly Val Leu Ala Gly
                245                 250                 255

Asn Ala Phe Val Tyr Pro His Gln Ile Ile Asn Leu Arg Thr Asn Asn
            260                 265                 270

Cys Ala Thr Leu Val Leu Pro Tyr Val Asn Ser Leu Ser Ile Asp Ser
        275                 280                 285

Met Thr Lys His Asn Asn Trp Gly Ile Ala Ile Leu Pro Leu Ala Pro
    290                 295                 300

Leu Asp Phe Ala Thr Glu Ser Ser Thr Glu Ile Pro Ile Thr Leu Thr
305                 310                 315                 320

Ile Ala Pro Met Cys Cys Glu Phe Asn Gly Leu Arg Asn Ile Thr Val
                325                 330                 335

Pro Arg Thr Gln Gly Leu Pro Val Leu Asn Thr Pro Gly Ser Asn Gln
            340                 345                 350

Tyr Leu Thr Ala Asp Asn Tyr Gln Ser Pro Cys Ala Ile Pro Glu Phe
        355                 360                 365

Asp Val Thr Pro Pro Ile Asp Ile Pro Gly Glu Val Arg Asn Met Met
    370                 375                 380

Glu Leu Ala Glu Ile Asp Thr Met Ile Pro Leu Asn Leu Thr Asn Gln
385                 390                 395                 400

Arg Lys Asn Thr Met Asp Met Tyr Arg Val Glu Leu Asn Asp Ala Ala
                405                 410                 415

His Ser Asp Thr Pro Ile Leu Cys Leu Ser Leu Ser Pro Ala Ser Asp
            420                 425                 430

Pro Arg Leu Ala His Thr Met Leu Gly Glu Ile Leu Asn Tyr Tyr Thr
        435                 440                 445

His Trp Ala Gly Ser Leu Lys Phe Thr Phe Leu Phe Cys Gly Ser Met
    450                 455                 460

Met Ala Thr Gly Lys Leu Leu Val Ser Tyr Ala Pro Pro Gly Ala Glu
465                 470                 475                 480

Ala Pro Lys Ser Arg Lys Glu Ala Met Leu Gly Thr His Val Ile Trp
                485                 490                 495

Asp Ile Gly Leu Gln Ser Ser Cys Thr Met Val Val Pro Trp Ile Ser
            500                 505                 510

Asn Thr Thr Tyr Arg Gln Thr Ile Asn Asp Ser Phe Thr Glu Gly Gly
        515                 520                 525
```

-continued

```
Tyr Ile Ser Met Phe Tyr Gln Thr Arg Val Val Val Pro Leu Ser Thr
    530                 535                 540

Pro Arg Lys Met Asp Ile Leu Gly Phe Val Ser Ala Cys Asn Asp Phe
545                 550                 555                 560

Ser Val Arg Leu Leu Arg Asp Thr Thr His Ile Ser Gln Glu Ala Met
                565                 570                 575

Pro Gln Gly Leu Gly Asp Leu Ile Glu Gly Val Val Glu Gly Val Thr
            580                 585                 590

Arg Asn Ala Leu Thr Pro Leu Thr Pro Ala Asn Asn Leu Pro Asp Thr
        595                 600                 605

Gln Ser Ser Gly Pro Ala His Ser Lys Glu Thr Pro Ala Leu Thr Ala
    610                 615                 620

Val Glu Thr Gly Ala Thr Asn Pro Leu Val Pro Ser Asp Thr Val Gln
625                 630                 635                 640

Thr Arg His Val Ile Gln Lys Arg Thr Arg Ser Glu Ser Thr Val Glu
                645                 650                 655

Ser Phe Phe Ala Arg Gly Ala Cys Val Ala Ile Ile Glu Val Asp Asn
            660                 665                 670

Asp Ala Pro Thr Lys Arg Ala Ser Lys Leu Phe Ser Val Trp Lys Ile
        675                 680                 685

Thr Tyr Lys Asp Thr Val Gln Leu Arg Arg Lys Leu Glu Phe Phe Thr
    690                 695                 700

Tyr Ser Arg Phe Asp Met Glu Phe Thr Phe Val Val Thr Ser Asn Tyr
705                 710                 715                 720

Thr Asp Ala Asn Asn Gly His Ala Leu Asn Gln Val Tyr Gln Ile Met
                725                 730                 735

Tyr Ile Pro Pro Gly Ala Pro Ile Pro Gly Lys Trp Asn Asp Tyr Thr
            740                 745                 750

Trp Gln Thr Ser Ser Asn Pro Ser Val Phe Tyr Thr Tyr Gly Ala Pro
        755                 760                 765

Pro Ala Arg Ile Ser Val Pro Tyr Val Gly Ile Ala Asn Ala Tyr Ser
    770                 775                 780

His Phe Tyr Asp Gly Phe Ala Lys Val Pro Leu Ala Gly Gln Ala Ser
785                 790                 795                 800

Thr Glu Gly Asp Ser Leu Tyr Gly Ala Ala Ser Leu Asn Asp Phe Gly
                805                 810                 815

Ser Leu Ala Val Arg Val Val Asn Asp His Asn Pro Thr Lys Leu Thr
            820                 825                 830

Ser Lys Ile Arg Val Tyr Met Lys Pro Lys His Val Arg Val Trp Cys
        835                 840                 845

Pro Arg Pro Pro Arg Ala Val Pro Tyr Tyr Gly Pro Gly Val Asp Tyr
    850                 855                 860

Lys Asp Gly Leu Ala Pro Leu Pro Glu Lys Gly Leu Thr Thr Tyr
865                 870                 875


<210> SEQ ID NO 19
<211> LENGTH: 880
<212> TYPE: PRT
<213> ORGANISM: Poliovirus

<400> SEQUENCE: 19

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
```

-continued

```
            20                  25                  30

Tyr Arg Asp Ser Ala Ser Asn Ala Ala Ser Lys Gln Asp Phe Ala Gln
        35                  40                  45

Asp Pro Ser Lys Phe Thr Glu Pro Ile Lys Asp Val Leu Ile Lys Thr
    50                  55                  60

Ala Pro Met Leu Asn Ser Pro Asn Ile Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Ile Arg
            100                 105                 110

Asp Thr Glu Ala Asn Pro Val Asp Gln Pro Thr Glu Pro Asp Val Ala
        115                 120                 125

Ala Cys Arg Phe Tyr Thr Leu Asp Thr Val Thr Trp Arg Lys Glu Ser
    130                 135                 140

Arg Gly Trp Trp Trp Lys Leu Pro Asp Ala Leu Lys Asp Met Gly Leu
145                 150                 155                 160

Phe Gly Gln Asn Met Phe Tyr His Tyr Leu Gly Arg Ala Gly Tyr Thr
                165                 170                 175

Val His Val Gln Cys Asn Ala Ser Lys Phe His Gln Gly Ala Leu Gly
            180                 185                 190

Val Phe Ala Val Pro Glu Met Cys Leu Ala Gly Asp Ser Thr Thr His
        195                 200                 205

Met Phe Thr Lys Tyr Glu Asn Ala Asn Pro Gly Glu Lys Gly Gly Glu
    210                 215                 220

Phe Lys Gly Ser Phe Thr Leu Asp Thr Asn Ala Thr Asn Pro Ala Arg
225                 230                 235                 240

Asn Phe Cys Pro Val Asp Tyr Leu Phe Gly Ser Gly Val Leu Val Gly
                245                 250                 255

Asn Ala Phe Val Tyr Pro His Gln Ile Ile Asn Leu Arg Thr Asn Asn
            260                 265                 270

Cys Ala Thr Leu Val Leu Pro Tyr Val Asn Ser Leu Ser Ile Asp Ser
        275                 280                 285

Met Thr Lys His Asn Asn Trp Gly Ile Ala Ile Leu Pro Leu Ala Pro
    290                 295                 300

Leu Asp Phe Ala Thr Glu Ser Ser Thr Glu Ile Pro Ile Thr Leu Thr
305                 310                 315                 320

Ile Ala Pro Met Cys Cys Glu Phe Asn Gly Leu Arg Asn Ile Thr Val
                325                 330                 335

Pro Arg Thr Gln Gly Leu Pro Val Leu Asn Thr Pro Gly Ser Asn Gln
            340                 345                 350

Tyr Leu Thr Ala Asp Asn Tyr Gln Ser Pro Cys Ala Ile Pro Glu Phe
        355                 360                 365

Asp Val Thr Pro Pro Ile Asp Ile Pro Gly Glu Val Arg Asn Met Met
    370                 375                 380

Glu Leu Ala Glu Ile Asp Thr Met Ile Pro Leu Asn Leu Thr Ser Gln
385                 390                 395                 400

Arg Lys Asn Thr Met Asp Met Tyr Arg Val Glu Leu Ser Asp Thr Ala
                405                 410                 415

His Ser Asp Thr Pro Ile Leu Cys Leu Ser Leu Ser Pro Ala Ser Asp
            420                 425                 430

Pro Arg Leu Ala His Thr Met Leu Gly Glu Ile Leu Asn Tyr Tyr Thr
        435                 440                 445
```

-continued

His Trp Ala Gly Ser Leu Lys Phe Thr Phe Leu Phe Cys Gly Ser Met
    450                 455                 460

Met Ala Thr Gly Lys Leu Leu Val Ser Tyr Ala Pro Pro Gly Ala Glu
465                 470                 475                 480

Ala Pro Lys Ser Arg Lys Glu Ala Met Leu Gly Thr His Val Ile Trp
                485                 490                 495

Asp Ile Gly Leu Gln Ser Ser Cys Thr Met Val Val Pro Trp Ile Ser
            500                 505                 510

Asn Thr Thr Tyr Arg Gln Thr Ile Asn Asp Ser Phe Thr Glu Gly Gly
        515                 520                 525

Tyr Ile Ser Met Phe Tyr Gln Thr Arg Val Val Val Pro Leu Ser Thr
    530                 535                 540

Pro Arg Lys Met Asp Ile Leu Gly Phe Val Ser Ala Cys Asn Asp Phe
545                 550                 555                 560

Ser Val Arg Leu Leu Arg Asp Thr Thr His Ile Ser Gln Glu Ala Met
                565                 570                 575

Pro Gln Gly Ile Gly Asp Met Ile Glu Gly Ala Val Glu Gly Ile Thr
            580                 585                 590

Lys Asn Ala Leu Val Pro Pro Thr Ser Thr Asn Ser Leu Pro Asp Thr
        595                 600                 605

Lys Pro Ser Gly Pro Ala His Ser Lys Glu Ile Pro Ala Leu Thr Ala
    610                 615                 620

Val Glu Thr Gly Ala Thr Asn Pro Leu Val Pro Ser Asp Thr Val Gln
625                 630                 635                 640

Thr Arg His Val Ile Gln Arg Arg Thr Arg Ser Glu Ser Thr Val Glu
                645                 650                 655

Ser Phe Phe Ala Arg Gly Ala Cys Val Ala Ile Ile Glu Val Asp Asn
            660                 665                 670

Asp Ala Pro Thr Lys Arg Ala Ser Arg Leu Phe Ser Val Trp Lys Ile
        675                 680                 685

Thr Tyr Lys Asp Thr Val Gln Leu Arg Arg Lys Leu Glu Phe Phe Thr
    690                 695                 700

Tyr Ser Arg Phe Asp Met Glu Phe Thr Phe Val Val Thr Ser Asn Tyr
705                 710                 715                 720

Ile Asp Ala Asn Asn Gly His Ala Leu Asn Gln Val Tyr Gln Ile Met
                725                 730                 735

Tyr Ile Pro Pro Gly Ala Pro Ile Pro Gly Lys Trp Asn Asp Tyr Thr
            740                 745                 750

Trp Gln Thr Ser Ser Asn Pro Ser Val Phe Tyr Thr Tyr Gly Ala Pro
        755                 760                 765

Pro Ala Arg Ile Ser Val Pro Tyr Val Gly Ile Ala Asn Ala Tyr Ser
    770                 775                 780

His Phe Tyr Asp Gly Phe Ala Lys Val Pro Leu Ala Gly Gln Ala Ser
785                 790                 795                 800

Thr Glu Gly Asp Ser Leu Tyr Gly Ala Ala Ser Leu Asn Asp Phe Gly
                805                 810                 815

Ser Leu Ala Val Arg Val Val Asn Asp His Asn Pro Thr Arg Leu Thr
            820                 825                 830

Ser Lys Ile Arg Val Tyr Met Lys Pro Lys His Val Arg Val Trp Cys
        835                 840                 845

Pro Arg Pro Pro Arg Ala Val Pro Tyr Phe Gly Pro Gly Val Asp Tyr
    850                 855                 860

-continued

```
Lys Asp Gly Thr Leu Thr Pro Leu Pro Glu Lys Gly Leu Thr Thr Tyr
865                 870                 875                 880


<210> SEQ ID NO 20
<211> LENGTH: 878
<212> TYPE: PRT
<213> ORGANISM: Poliovirus

<400> SEQUENCE: 20

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Lys Asp Ser Ala Ser Asn Ala Ala Ser Lys Gln Asp Tyr Ser Gln
        35                  40                  45

Asp Pro Ser Lys Phe Thr Glu Pro Leu Lys Asp Val Leu Ile Lys Thr
    50                  55                  60

Ala Pro Thr Leu Asn Ser Pro Asn Val Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Phe Ile Arg
            100                 105                 110

Asp Asp Glu Ala Asn Pro Val Asp Gln Pro Thr Glu Pro Asp Val Ala
        115                 120                 125

Thr Cys Arg Phe Tyr Thr Leu Asp Thr Val Met Trp Gly Lys Glu Ser
    130                 135                 140

Lys Gly Trp Trp Trp Lys Leu Pro Asp Ala Leu Arg Asp Met Gly Leu
145                 150                 155                 160

Phe Gly Gln Asn Met Tyr Tyr His Tyr Leu Gly Arg Ser Gly Tyr Thr
                165                 170                 175

Val His Val Gln Cys Asn Ala Ser Lys Phe His Gln Gly Ala Leu Gly
            180                 185                 190

Val Phe Ala Ile Pro Glu Tyr Cys Leu Ala Gly Asp Ser Asp Lys Gln
        195                 200                 205

Arg Tyr Thr Ser Tyr Ala Asn Ala Asn Pro Gly Glu Lys Gly Gly Lys
    210                 215                 220

Phe Tyr Ser Gln Phe Asn Arg Asp Thr Ala Val Thr Ser Pro Lys Arg
225                 230                 235                 240

Glu Phe Cys Pro Val Asp Tyr Leu Leu Gly Cys Gly Val Leu Leu Gly
                245                 250                 255

Asn Ala Phe Val Tyr Pro His Gln Ile Ile Asn Leu Arg Thr Asn Asn
            260                 265                 270

Ser Ala Thr Ile Val Leu Pro Tyr Val Asn Ala Leu Ala Ile Asp Ser
        275                 280                 285

Met Val Lys His Asn Asn Trp Gly Ile Ala Ile Leu Pro Leu Ser Pro
    290                 295                 300

Leu Asp Phe Ala Gln Asp Ser Ser Val Glu Ile Pro Ile Thr Val Thr
305                 310                 315                 320

Ile Ala Pro Met Cys Ser Glu Phe Asn Gly Leu Arg Asn Val Thr Ala
                325                 330                 335

Pro Lys Phe Gln Gly Leu Pro Val Leu Asn Thr Pro Gly Ser Asn Gln
            340                 345                 350

Tyr Leu Thr Ser Asp Asn His Gln Ser Pro Cys Ala Ile Pro Glu Phe
        355                 360                 365
```

```
Asp Val Thr Pro Pro Ile Asp Ile Pro Gly Glu Val Lys Asn Met Met
    370                 375                 380

Glu Leu Ala Glu Ile Asp Thr Met Ile Pro Leu Asn Leu Glu Asn Thr
385                 390                 395                 400

Lys Arg Asn Thr Met Asp Met Tyr Arg Val Thr Leu Ser Asp Ser Ala
                405                 410                 415

Asp Leu Ser Gln Pro Ile Leu Cys Leu Ser Leu Ser Pro Ala Ser Asp
            420                 425                 430

Pro Arg Leu Ser His Thr Met Leu Gly Glu Val Leu Asn Tyr Tyr Thr
        435                 440                 445

His Trp Ala Gly Ser Leu Lys Phe Thr Phe Leu Phe Cys Gly Ser Met
    450                 455                 460

Met Ala Thr Gly Lys Ile Leu Val Ala Tyr Ala Pro Pro Gly Ala Gln
465                 470                 475                 480

Pro Pro Thr Ser Arg Lys Glu Ala Met Leu Gly Thr His Val Ile Trp
                485                 490                 495

Asp Leu Gly Leu Gln Ser Ser Cys Thr Met Val Val Pro Trp Ile Ser
            500                 505                 510

Asn Val Thr Tyr Arg Gln Thr Thr Gln Asp Ser Phe Thr Glu Gly Gly
        515                 520                 525

Tyr Ile Ser Met Phe Tyr Gln Thr Arg Ile Val Val Pro Leu Ser Thr
    530                 535                 540

Pro Lys Ser Met Ser Met Leu Gly Phe Val Ser Ala Cys Asn Asp Phe
545                 550                 555                 560

Ser Val Arg Leu Leu Arg Asp Thr Thr His Ile Ser Gln Ser Ala Leu
                565                 570                 575

Pro Gln Gly Ile Glu Asp Leu Ile Thr Glu Val Ala Gln Gly Ala Leu
            580                 585                 590

Thr Leu Ser Leu Pro Lys Gln Gln Asp Ser Leu Pro Asp Thr Lys Ala
        595                 600                 605

Ser Gly Pro Ser His Ser Lys Glu Val Pro Ala Leu Thr Ala Val Glu
    610                 615                 620

Thr Gly Ala Thr Asn Pro Leu Val Pro Ser Asp Thr Val Gln Thr Arg
625                 630                 635                 640

His Val Ile Gln Arg Arg Ser Arg Ser Glu Ser Thr Ile Glu Ser Phe
                645                 650                 655

Phe Ala Arg Gly Ala Cys Val Ala Ile Ile Glu Val Asp Asn Glu Glu
            660                 665                 670

Pro Thr Thr Arg Ala Gln Lys Leu Phe Ala Thr Trp Arg Ile Thr Tyr
        675                 680                 685

Lys Asp Thr Val Gln Leu Arg Arg Lys Leu Glu Phe Phe Thr Tyr Ser
    690                 695                 700

Arg Phe Asp Met Glu Phe Thr Phe Val Val Thr Ala Asn Phe Thr Asn
705                 710                 715                 720

Thr Asn Asn Gly His Ala Leu Asn Gln Val Tyr Gln Ile Met Tyr Ile
                725                 730                 735

Pro Pro Gly Ala Pro Thr Pro Lys Ser Trp Asp Asp Tyr Thr Trp Gln
            740                 745                 750

Thr Ser Ser Asn Pro Ser Ile Phe Tyr Thr Tyr Gly Ala Ala Pro Ala
        755                 760                 765

Arg Ile Ser Val Pro Tyr Val Gly Leu Ala Asn Ala Tyr Ser His Phe
    770                 775                 780
```

Tyr Asp Gly Phe Ala Lys Val Pro Leu Lys Thr Asp Ala Asn Asp Gln
785 790 795 800

Ile Gly Asp Ser Leu Tyr Ser Ala Met Thr Val Asp Asp Phe Gly Val
805 810 815

Leu Ala Ile Arg Val Val Asn Asp His Asn Pro Thr Lys Val Thr Ser
820 825 830

Lys Val Arg Ile Tyr Met Lys Pro Lys His Val Arg Val Trp Cys Pro
835 840 845

Arg Pro Pro Arg Ala Val Pro Tyr Tyr Gly Pro Gly Val Asp Tyr Lys
850 855 860

Asp Asn Leu Asn Pro Leu Ser Glu Lys Gly Leu Thr Thr Tyr
865 870 875

<210> SEQ ID NO 21
<211> LENGTH: 878
<212> TYPE: PRT
<213> ORGANISM: Poliovirus

<400> SEQUENCE: 21

Met Gly Ala Gln Val Ser Ser Gln Lys Val Gly Ala His Glu Asn Ser
1 5 10 15

Asn Arg Ala Tyr Gly Gly Ser Thr Ile Asn Tyr Thr Thr Ile Asn Tyr
20 25 30

Tyr Lys Asp Ser Ala Ser Asn Ala Ala Ser Lys Gln Asp Tyr Ser Gln
35 40 45

Asp Pro Ser Lys Phe Thr Glu Pro Leu Lys Asp Val Leu Ile Lys Thr
50 55 60

Ala Pro Ala Leu Asn Ser Pro Asn Val Glu Ala Cys Gly Tyr Ser Asp
65 70 75 80

Arg Val Leu Gln Leu Thr Leu Gly Asn Ser Thr Ile Thr Thr Gln Glu
85 90 95

Ala Ala Asn Ser Val Val Ala Tyr Gly Arg Trp Pro Glu Phe Ile Arg
100 105 110

Asp Asp Glu Ala Asn Pro Val Asp Gln Pro Thr Glu Pro Asp Val Ala
115 120 125

Thr Cys Arg Phe Tyr Thr Leu Asp Thr Val Met Trp Gly Lys Glu Ser
130 135 140

Lys Gly Trp Trp Trp Lys Leu Pro Asp Ala Leu Arg Asp Met Gly Leu
145 150 155 160

Phe Gly Gln Asn Met Tyr Tyr His Tyr Leu Gly Arg Ser Gly Tyr Thr
165 170 175

Val His Val Gln Cys Asn Ala Ser Lys Phe His Gln Gly Ala Leu Gly
180 185 190

Val Phe Ala Ile Pro Glu Tyr Cys Leu Ala Gly Asp Ser Asp Lys Gln
195 200 205

Arg Tyr Thr Ser Tyr Ala Asn Ala Asn Pro Gly Glu Arg Gly Gly Lys
210 215 220

Phe Tyr Ser Gln Phe Asn Lys Asp Asn Ala Val Thr Ser Pro Lys Arg
225 230 235 240

Glu Phe Cys Pro Val Asp Tyr Leu Leu Gly Cys Gly Val Leu Leu Gly
245 250 255

Asn Ala Phe Val Tyr Pro His Gln Ile Ile Asn Leu Arg Thr Asn Asn
260 265 270

Ser Ala Thr Ile Val Leu Pro Tyr Val Asn Ser Leu Ala Ile Asp Ser
275 280 285

```
Met Val Lys His Asn Asn Trp Gly Ile Ala Ile Leu Pro Leu Ser Pro
    290                 295                 300

Leu Asp Phe Ala Gln Asp Ser Ser Val Glu Ile Pro Ile Thr Val Thr
305                 310                 315                 320

Ile Ala Pro Met Cys Ser Glu Phe Asn Gly Leu Arg Asn Val Thr Ala
                325                 330                 335

Pro Lys Phe Gln Gly Leu Pro Val Leu Asn Thr Pro Gly Ser Asn Gln
            340                 345                 350

Tyr Leu Thr Ser Asp Asn His Gln Ser Pro Cys Ala Ile Pro Glu Phe
        355                 360                 365

Asp Val Thr Pro Pro Ile Asp Ile Pro Gly Glu Val Lys Asn Met Met
    370                 375                 380

Glu Leu Ala Glu Ile Asp Thr Met Ile Pro Leu Asn Leu Glu Ser Thr
385                 390                 395                 400

Lys Arg Asn Thr Met Asp Met Tyr Arg Val Thr Leu Ser Asp Ser Ala
                405                 410                 415

Asp Leu Ser Gln Pro Ile Leu Cys Leu Ser Leu Ser Pro Ala Phe Asp
            420                 425                 430

Pro Arg Leu Ser His Thr Met Leu Gly Glu Val Leu Asn Tyr Tyr Thr
        435                 440                 445

His Trp Ala Gly Ser Leu Lys Phe Thr Phe Leu Phe Cys Gly Ser Met
    450                 455                 460

Met Ala Thr Gly Lys Ile Leu Val Ala Tyr Ala Pro Pro Gly Ala Gln
465                 470                 475                 480

Pro Pro Thr Ser Arg Lys Glu Ala Met Leu Gly Thr His Val Ile Trp
                485                 490                 495

Asp Leu Gly Leu Gln Ser Ser Cys Thr Met Val Val Pro Trp Ile Ser
            500                 505                 510

Asn Val Thr Tyr Arg Gln Thr Thr Gln Asp Ser Phe Thr Glu Gly Gly
        515                 520                 525

Tyr Ile Ser Met Phe Tyr Gln Thr Arg Ile Val Val Pro Leu Ser Thr
    530                 535                 540

Pro Lys Ser Met Ser Met Leu Gly Phe Val Ser Ala Cys Asn Asp Phe
545                 550                 555                 560

Ser Val Arg Leu Leu Arg Asp Thr Thr His Ile Ser Gln Ser Ala Leu
                565                 570                 575

Pro Gln Gly Ile Glu Asp Leu Ile Ser Glu Val Ala Gln Gly Ala Leu
            580                 585                 590

Thr Leu Ser Leu Pro Lys Gln Gln Asp Ser Leu Pro Asp Thr Lys Ala
        595                 600                 605

Ser Gly Pro Ala His Ser Lys Glu Val Pro Ala Leu Thr Ala Val Glu
    610                 615                 620

Thr Gly Ala Thr Asn Pro Leu Ala Pro Ser Asp Thr Val Gln Thr Arg
625                 630                 635                 640

His Val Val Gln Arg Arg Ser Arg Ser Glu Ser Thr Ile Glu Ser Phe
                645                 650                 655

Phe Ala Arg Gly Ala Cys Val Ala Ile Ile Glu Val Asp Asn Glu Gln
            660                 665                 670

Pro Thr Thr Arg Ala Gln Lys Leu Phe Ala Met Trp Arg Ile Thr Tyr
        675                 680                 685

Lys Asp Thr Val Gln Leu Arg Arg Lys Leu Glu Phe Phe Thr Tyr Ser
    690                 695                 700
```

-continued

```
Arg Phe Asp Met Glu Phe Thr Phe Val Val Thr Ala Asn Phe Thr Asn
705                 710                 715                 720

Ala Asn Asn Gly His Ala Leu Asn Gln Val Tyr Gln Ile Met Tyr Ile
                725                 730                 735

Pro Pro Gly Ala Pro Thr Pro Lys Ser Trp Asp Asp Tyr Thr Trp Gln
            740                 745                 750

Thr Ser Ser Asn Pro Ser Ile Phe Tyr Thr Tyr Gly Ala Ala Pro Ala
        755                 760                 765

Arg Ile Ser Val Pro Tyr Val Gly Leu Ala Asn Ala Tyr Ser His Phe
    770                 775                 780

Tyr Asp Gly Phe Ala Lys Val Pro Leu Lys Thr Asp Ala Asn Asp Gln
785                 790                 795                 800

Ile Gly Asp Ser Leu Tyr Ser Ala Met Thr Val Asp Asp Phe Gly Val
                805                 810                 815

Leu Ala Val Arg Val Val Asn Asp His Asn Pro Thr Lys Val Thr Ser
            820                 825                 830

Lys Val Arg Ile Tyr Met Lys Pro Lys His Val Arg Val Trp Cys Pro
        835                 840                 845

Arg Pro Pro Arg Ala Val Pro Tyr Tyr Gly Pro Gly Val Asp Tyr Arg
    850                 855                 860

Asn Asn Leu Asp Pro Leu Ser Glu Lys Gly Leu Thr Thr Tyr
865                 870                 875


<210> SEQ ID NO 22
<211> LENGTH: 24
<212> TYPE: DNA
<213> ORGANISM: Artificial Sequence
<220> FEATURE:
<223> OTHER INFORMATION: Primer P1F

<400> SEQUENCE: 22

gcgagttgga ttggccatcc agtg                                            24


<210> SEQ ID NO 23
<211> LENGTH: 24
<212> TYPE: DNA
<213> ORGANISM: Artificial Sequence
<220> FEATURE:
<223> OTHER INFORMATION: Primer P1R

<400> SEQUENCE: 23

tggaaggtgg gtcccacaaa cgac                                            24
```

POLIOVACCINE

CROSS REFERENCE TO RELATED APPLICATIONS

This application is a U.S. National Stage Application of PCT/GB2018/050129, International Filing Date, 17 Jan. 2018, which claims priority to GB 1700825.1, filed 17 Jan. 2017, the disclosures of which are incorporated herein by reference.

REFERENCE TO SUBMISSION OF A SEQUENCE LISTING AS A TEXT FILE

The Sequence Listing written in file Sequence-Listing-1148672.txt created on Jul. 16, 2019, 77,824 bytes, machine format IBM-PC, MS-Windows operating system, is hereby incorporated by reference in its entirety for all purposes.

FIELD OF THE INVENTION

This invention relates to poliovaccines. In particular, the invention relates to poliovirus like particles, methods of identifying modifications useful in the production of such poliovirus like particles, methods of producing such poliovirus like particles and the use of such poliovirus like particles in methods of vaccinating against poliovirus.

BACKGROUND OF THE INVENTION

The global polio eradication initiative of the World Health Organisation (WHO) has made great progress. The main tool used in the eradication initiative has been the live attenuated oral polio vaccine. As a result of the initiative, naturally occurring wild type 2 poliovirus has not been seen globally since 1999, type 3 since 2012 and Afghanistan and Pakistan are the only countries where endogenous type 1 virus is still circulating.

The situation is complex however, largely as a consequence of the live attenuated nature of the vaccine. In particular, the live attenuated vaccine has been known for many years to cause vaccine associated poliomyelitis in a small proportion of recipients or their contacts, and more recently to be able to revert to a transmissible phenotype, causing outbreaks in several parts of the world where vaccine programs have become less vigorous as polio has disappeared. Prolonged excretion of vaccine-derived polioviruses by some immunodeficient patients has also been well documented. The use of the oral polio vaccine and its ability to alter its phenotype is therefore an issue in the eradication of polio worldwide.

It would be extremely unwise to stop vaccination immediately the last wild type virus is believed to have been isolated because wild type virus may be circulating undetected due to poor surveillance in some areas. Also, immunodeficient individuals may continue to excrete virus for a very long time after vaccination and could be a source for re-emergence. Further, there may still be outbreaks caused by the oral vaccine from the last rounds of its use.

Vaccination and surveillance must therefore continue for some time after eradication of the wild type virus is declared. Processes are being put in place to ensure that when polio is eradicated it does not re-emerge and these encompass the containment of work on the live virus and of production of the vaccine needed to ensure that coverage is maintained to guard against possible re-emergence. The issues have been brought into focus by the WHO decision to withdraw the type 2 component from the oral polio vaccine (OPV) from mid-2016, and to introduce a single immunisation with an inactivated polio vaccine (IPV).

All vaccines in current use depend on growth of virus and most of the non-replicating vaccines (i.e. IPV) involve wild type viruses known to cause poliomyelitis. In more detail, IPV production involves the growth of large quantities of live poliovirus, which are then inactivated with formalin. The poliovirus strains in current use are mainly wild types known to be able to cause poliomyelitis in humans, although two companies have licensed products based on the live attenuated Sabin strains used in the current oral polio vaccine. Safe production of IPV is essential and conventional research is focused on devising viable production strains that are intrinsically safer than the attenuated live strains currently in use.

The Salk vaccine is based on three wild, virulent wild type strains of poliovirus namely the Mahoney (type 1 poliovirus), MEF-1 (type 2 poliovirus), and Saukett (type 3 poliovirus) strains, grown in Vero cells ex vivo (Wood et al, Biologicals 25:59-64, 1997). The wild type polioviruses are then inactivated with formalin to produce the IPV. The wild type strains currently used in IPV production are known to be paralytic in humans and are used in large amounts in IPV production. This presents a serious containment issue, which may not be easy to reconcile with the production scales required for IPV. Some interest has been expressed in using the same strains in the manufacture of inactivated vaccine as are used in the oral vaccine on the grounds that they are attenuated and therefore present less of a hazard should they escape. However, their instability on replication in humans means that they remain hazardous, and their immunogenic properties are different from those of the wild type strains currently used so that a major clinical development program would be required to develop an IPV based on these strains.

The live attenuated poliovirus vaccines developed by Sabin in the 1950s using essentially empirical procedures have been used throughout the world as live oral poliovaccines. Over the past several years, scientists have employed a number of molecular biological techniques in an attempt to elucidate the mechanism by which the neurovirulence of these vaccine strains is reduced. Most of the work has concentrated on serotypes 1 and 3. For both of these the complete nucleotide sequences of the vaccine strains have been compared with those of their neurovirulent progenitors. In the case of poliovirus type 1, the vaccine strain differs from its progenitor at 47 positions in the 7441 base genome (Nomoto et al., Proc. Natl. Acad. Sci. USA 79:5793-5797, 1982). Analogous studies on poliovirus type 3 reveal just 10 nucleotide sequence differences in the 7432 base genome between the vaccine and its progenitor strain (Stanway et al., Proc. Natl. Acad. Sci. USA 81:1539-1543, 1984). The type 2 strain was developed from a naturally attenuated parent but analysis of a neurovirulent revertant strain, isolated from a case of vaccine-associated poliomyelitis, identified 17 differences from Sabin 2 (Pollard et al., J. Virol. 63: 4949-4951, 1989). As described above, there are though challenges associated with the use of live attenuated viruses, such as the risk of reversion to a virulent transmissible form.

It would therefore be highly desirable to develop a vaccine which does not involve infectious poliovirus at any stage in the production process.

SUMMARY OF THE INVENTION

A possible solution to the need for virus growth would be to generate empty viral capsids by recombinant technology.

However, hitherto such particles are so unstable as to be unusable. The present inventors have developed a method which allows the identification of modifications within the poliovirus capsid which modulate capsid stability, particularly modifications which stabilise the poliovirus capsid. Such modifications are typically mutations in the capsid amino acid sequence. Using this method, the inventors have genetically manipulated the poliovirus capsid, to produce stable empty capsids, also known as poliovirus like particles (VLP) for all three serotypes. The present inventors have demonstrated that said VLP are extremely stable and generate high levels of protective antibodies in animal models. These VLP therefore provide major advantages compared to the current OPV and IPV in terms of both safety and the properties of the product.

Accordingly, the present invention provides a poliovirus-like particle (VLP) comprising at least one modification relative to the poliovirus particle from which the VLP is derived, wherein said at least one modification stabilises the VLP. Said at least one modification may be a modification as defined in Table 1, 2 or 3. Typically there is at least one modification in each of (a) a protomer interface; and (b) a pentamer interface, wherein said at least one modification in each of the protomer interface and pentamer interface is a modification as defined in Table 1, 2 or 3. The poliovirus-like particle (VLP) of the invention may be is derived from a wild-type poliovirus or from a vaccine strain, and may be derived from a type 1, type 2 or type 3 poliovirus. The poliovirus-like particle (VLP) of the invention may be derived from: (a) a type 1 poliovirus selected from Mahoney and Sabin 1; (b) a type 2 poliovirus selected from MEF and Sabin 2; or (c) a type 3 poliovirus selected from Saukett and Sabin 3.

In preferred embodiments, the invention provides a poliovirus-like particle (VLP) which comprises at least three modifications relative to the poliovirus particle from which the VLP is derived which stabilise the VLP, wherein there is at least one modification in each of: (a) a protomer interface; and (b) a pentamer interface.

The poliovirus-like particle (VLP) of the invention may further comprise at least one modification in a pocket domain relative to the poliovirus particle from which the VLP is derived, said modification may be as defined in Table 1, 2 or 3.

A poliovirus-like particle (VLP) of the invention may be derived from a type 1 poliovirus, wherein: (a) the protomer interface comprises a mutation at one or both of residues 3178 and 1248 or residues corresponding thereto; and/or (b) the pentamer interface comprises a mutation at one or both of residues 2025 and 2057 or residues corresponding thereto; wherein optionally said VLP comprises a modification in a pocket domain, and said modification is preferably a mutation at residue 1196 or a residue corresponding thereto. In some embodiments: (a) the protomer interface comprises one or both of the mutations Q3178L and H1248P; and/or (b) the pentamer interface comprises one or both of the mutations T2025A and D2057E; wherein optionally said VLP comprises a modification in a pocket domain, and said modification is preferably the mutation V1196L. The poliovirus-like particle (VLP) may comprise both the mutations at residues 3178 and 1248 of the protomer interface or residues corresponding thereto, both mutations at residues 2025 and 2057 of the pentamer interface or residues corresponding thereto and optionally the mutation at residue 1196 of the pocket domain or a residue corresponding thereto.

A poliovirus-like particle (VLP) of the invention may be derived from a type 2 poliovirus, wherein: (a) the protomer interface comprises a mutation at one or both of residues 3178 and 1107 or residues corresponding thereto; and/or (b) the pentamer interface comprises a mutation at one or more of residues 3085, 1041 and 2057 or residues corresponding thereto; wherein optionally said VLP comprises a modification in a pocket domain, and said modification is preferably a mutation at one or more of residues 1134, 1159 and 1183 or residues corresponding thereto. In some embodiments: (a) the protomer interface comprises one or both of the mutations Q3178L and V1107I; and/or (b) the pentamer interface comprises one or more of the mutations L3085F, T1041I and D2057A; wherein optionally said VLP comprises a modification in a pocket domain, and said modification is preferably one or more of the mutations F1134L, Y1159F and V1183L. The poliovirus-like particle may comprise (a) the mutations at residue 3178 of the protomer interface or a residue corresponding thereto, mutations at both residues 3085 and 1041 of the pentamer interface or residues corresponding thereto and optionally mutations at both residues 1134 and 1159 of the pocket domain or residues corresponding thereto; or (b) both mutations at residues 3178 and 1107 of the protomer interface or residues corresponding thereto, the mutation at residue 2057 of the pentamer interface or a residue corresponding thereto, and optionally mutations at both residues 1134 and 1183 of the pocket domain or residues corresponding thereto.

A poliovirus-like particle (VLP) of the invention may be derived from a type 3 poliovirus, wherein: (a) the protomer interface comprises a mutation at one or both of residues 2215 and 3091 or residues corresponding thereto; and/or (b) the pentamer interface comprises a mutation at one or both of residues 2018 and 3085 or residues corresponding thereto; wherein optionally said VLP comprises a modification in a pocket domain, and said modification is preferably a mutation at residue 1132 (VP1 132) or a residue corresponding thereto. In some embodiments: (a) the protomer interface comprises one or both of the mutations L2215M and F3091S; and/or (b) the pentamer interface comprises one or both of the mutations L20181 and L3085F; wherein optionally said VLP comprises a modification in a pocket domain, and said modification is preferably the mutation F1132L. The poliovirus-like particle (VLP) may comprise both mutations at residues 2215 and 3091 of the protomer interface or residues corresponding thereto, both mutations at residues 2018 and 3085 of the pentamer interface or residues corresponding thereto, and optionally the mutation at residue 1132 of the pocket domain, or a residue corresponding thereto.

The poliovirus-like particle (VLP) of the invention may further comprise one or more additional modification within one or more of the pocket domain, the protomer interface and/or the pentamer interface, wherein optionally said one or more additional modification is a modification as defined in Table 1, 2 or 3.

The poliovirus-like particle (VLP) of the invention may further comprise at least one further modification in one or more additional structural domain, wherein optionally said one or more additional modification is a modification as defined in Table 1, 2 or 3. Said one or more additional structural domain may be selected from: (a) a VP2/VP3 interface; (b) an internal network; and/or (c) a canyon. The internal network may comprise a three-fold axis, a five-fold axis and/or a tube below the five-fold axis, and wherein said at least one further modification is located at or in close proximity to said three-fold axis, five-fold axis or tube below the five-fold axis.

The VLP of the invention may be derived from a type 1 poliovirus, wherein: (a) the VP2/VP3 interface comprises a mutation at residue 3119 or a residue corresponding thereto; and/or the internal network comprises a mutation at residue 4018 or a residue corresponding thereto. In some embodiments: (a) the VP2/VP3 interface comprises the mutation L3319M; and/or (b) the internal network comprises the mutation R4018G. The VLP of the invention may be derived from a type 2 poliovirus, wherein the internal network comprises a mutation at residue 4057, or a residue corresponding thereto. In some embodiments, the internal network comprises the mutation 14057V. The poliovirus-like particle (VLP) may be derived from a type 3 poliovirus, wherein: (a) the VP2/VP3 interface comprises a mutation at residue 2241 or a residue corresponding thereto; (b) the internal network comprises a mutation at one or more of residues 1054, 4067 and 3019 or residues corresponding thereto; and/or (c) the canyon comprises a mutation at residue 1105 or a residue corresponding thereto. In some embodiments: (a) the VP2/VP3 interface comprises the mutation D2241E; (b) the internal network comprises one or more of the mutations VP1 54 alanine to valine, T4067A and H3019Y; and/or (c) the canyon comprises the mutation T1105M. The poliovirus-like particle (VLP) may further comprise one or more additional modification within one or more of the VP2/VP3 interface, the internal network and/or the canyon, wherein optionally said one or more additional modification is a modification as defined in Table 1, 2, or 3.

In some embodiments, the poliovirus-like particle (VLP) of the invention: (a) is derived from a type 1 poliovirus and comprises (i) the mutations Q3178L and H1248P in the protomer interface, (ii) the mutations T2025A and D2057E in the pentamer interface, (iii) the mutation L3119M in the VP2/VP3 interface, and (iv) the mutation R4018G in the internal network; wherein said VLP optionally further comprises the mutation V1196L in the pocket domain; (b) is derived from a type 2 poliovirus and comprises (i) the mutations F1134L and Y1159F in the pocket domain, (ii) the mutation Q3178L in the protomer interface, and (iii) the mutations L3085F and T1041I in the pentamer interface; (c) is derived from a type 2 poliovirus and comprises (i) the mutations F1134L and V1183L in the pocket domain, (ii) the mutations Q3178L and V1107I in the protomer interface, (iii) the mutation D2057A in the pentamer interface; and (iv) the mutation 1405V in the internal network; or (d) is derived from a type 3 poliovirus and comprises (i) the mutation F1132L in the pocket domain, (ii) the mutations L2215M and F3091S in the protomer interface, (iii) the mutations L20181 and L3085F in the pentamer interface, (iv) the mutation D2241E in the VP2/VP3 interface, (v) the mutations T4067A, H3019Y and optionally A1054V in the internal network, and (vi) the mutation T1105M in the canyon.

In some embodiments, the poliovirus-like particle (VLP) of the invention is: (a) a type 1 VLP derived from a type 1 poliovirus with (i) a P1 having an amino acid sequence of SEQ ID NO: 16 or 17; (ii) a VP1 having an amino acid sequence of SEQ ID NO: 1, a VP0 having an amino acid sequence of SEQ ID NO: 5, and a VP3 having an amino acid sequence of SEQ ID NO: 3, (iii) a VP1 having an amino acid sequence of SEQ ID NO: 1, a VP2 having an amino acid sequence of SEQ ID NO: 2, and a VP3 having an amino acid sequence of SEQ ID NO: 3 and a VP4 having an amino acid sequence of SEQ ID NO: 4; and/or (iv) a P1; VP1, VP0 and VP3; or a VP1, VP2, VP3 and VP4 having an amino acid sequence with at least 90% sequence identity to the amino acid sequences of (i) to (iii); (b) a type 2 VLP derived from a type 2 poliovirus with (i) a P1 having an amino acid sequence of SEQ ID NO: 18 or 19; (ii) a VP1 having an amino acid sequence of SEQ ID NO: 6, a VP0 having an amino acid sequence of SEQ ID NO: 10, and a VP3 having an amino acid sequence of SEQ ID NO: 8, (iii) a VP1 having an amino acid sequence of SEQ ID NO: 6, a VP2 having an amino acid sequence of SEQ ID NO: 7, and a VP3 having an amino acid sequence of SEQ ID NO: 8 and a VP4 having an amino acid sequence of SEQ ID NO: 9; and/or (iv) a P1; VP1, VP0 and VP3; or a VP1, VP2, VP3 and VP4 having an amino acid sequence with at least 90% sequence identity to the amino acid sequences of (i) to (iii); or (c) a type 3 VLP derived from a type 3 poliovirus with (i) a P1 having an amino acid sequence of SEQ ID NO: 20 or 21; (ii) a VP1 having an amino acid sequence of SEQ ID NO: 11, a VP0 having an amino acid sequence of SEQ ID NO: 15, and a VP3 having an amino acid sequence of SEQ ID NO: 13, (iii) a VP1 having an amino acid sequence of SEQ ID NO: 11, a VP2 having an amino acid sequence of SEQ ID NO: 12, and a VP3 having an amino acid sequence of SEQ ID NO: 13 and a VP4 having an amino acid sequence of SEQ ID NO: 14; and/or (iv) a P1; VP1, VP0 and VP3; or a VP1, VP2, VP3 and VP4 having an amino acid sequence with at least 90% sequence identity to the amino acid sequences of (i) to (iii).

The invention further provides a method of identifying a modification within a poliovirus capsid which increase the stability of said poliovirus capsid, comprising: (a) introducing a destabilising mutation into the capsid of a poliovirus strain; (b) growing said poliovirus strain at semi-permissive temperatures; and (c) screening the resulting polioviruses to identify one or more modification that reverse the effect of the destabilising mutation. The semi-permissive temperature may be a temperature in the range of from about 38° C. to about 40° C. Said method may further comprise the step of introducing one or more modification identified in step (c) into a wild-type poliovirus and verifying that said one or more modification increases the stability of the poliovirus capsid.

The invention also provides a method of producing a poliovirus-like particle (VLP) comprising: (a) introducing an infectious RNA transcript encoding the VLP into a host mammalian cell; or (b) recombinantly producing poliovirus capsid-derived polypeptides comprising one or more modification identified by the method of the invention, and assembling said polypeptides to form a VLP.

The invention further provides a poliovirus-like particle (VLP) obtainable by the method of the invention. Said VLP may be as defined herein.

The invention also provides a composition comprising the poliovirus-like particle (VLP) of the invention and a pharmaceutically acceptable excipient or diluent.

The invention further provides a vaccine comprising: (i) the poliovirus-like particle (VLP) of the invention; or (ii) a nucleic acid encoding the VLP of the invention; and an adjuvant. Said vaccine may be a nucleic acid vector comprising the polynucleotide or expression vector of the invention. Said vaccine may be an RNA vaccine comprising a P1 RNA encoding for the poliovirus-like particle (VLP) and which further encodes a viral protease for cleavage of the P1 precursor.

The invention also provides the poliovirus-like particle (VLP), composition or vaccine of the invention for use in a method of vaccinating against poliovirus.

The invention further provides the use of a poliovirus like particle (VLP) or composition of the invention in the manufacture of a medicament for use in a method of vaccinating against poliovirus.

The invention also provides a method of vaccinating a subject against poliovirus, the method comprising administering to a subject in need thereof an effective amount of a poliovirus-like particle (VLP), composition or vaccine of the invention.

The invention also provides a polynucleotide molecule encoding a poliovirus-like particle (VLP) of the invention.

The invention further provides an expression vector comprising a polynucleotide of the invention, which is operably linked to a promoter.

The invention also provides a cell producing a poliovirus-like particle (VLP) of the invention, wherein optionally said cell comprises a polynucleotide or expression vector of the invention.

BRIEF DESCRIPTION OF THE DRAWINGS

FIG. 1: Alignment of the P1 capsid precursor polypeptide of the Mahoney (SEQ ID NO:16), Sabin 1 (SEQ ID NO:17), MEF (SEQ ID NO:18), Sabin 2 (SEQ ID NO:19), Saukett (SEQ ID NO:20), and Sabin 3 (SEQ ID NO:21) strains. The mature VP proteins as cleaved from the P1 precursor as indicated as follows: VP0 (residues 1-341 of Mahoney, SEQ ID NO:16) shown in bold; VP3 (residues 342-579 of Mahoney, SEQ ID NO:16) shown as underlined; VP1 (residues 580-882 of Mahoney, SEQ ID NO:16) shown in italics. The VP0 is further cleaved in the mature poliovirus virion to VP2 (residues 70-341 of Mahoney, SEQ ID NO:16), shown as dotted-underlined; and VP4 (residues 1-69 of Mahoney, SEQ ID NO:16), shown as double-underlined.

FIG. 4: Thermostability of type 3 Leon particles. Reactivity of (A) virus and (B) empty capsid aliquots with MAb 520 and MAb 517 in ELISA after incubation at different temperatures for 10 minutes. MAb 520 is specific for D Antigen and MAb 517 is specific for C Antigen.

FIG. 5: Long-term stability of virus and empty capsid preparations compared to the IPV reference. Proportion of D antigen reactivity remaining after incubation at 37° C. relative to incubation at 4° C. Aliquots of IPV, virus and empty capsid samples were incubated at 37° C. and samples were removed at intervals and analysed by D Antigen ELISA; reactivity is expressed relative to samples incubated at 4° C. for the same period. (A) Type 1, (B) Type 2, (C) Type 3.

DETAILED DESCRIPTION OF THE INVENTION

Poliovirus and Poliovirus Like Particles

Figure 2:
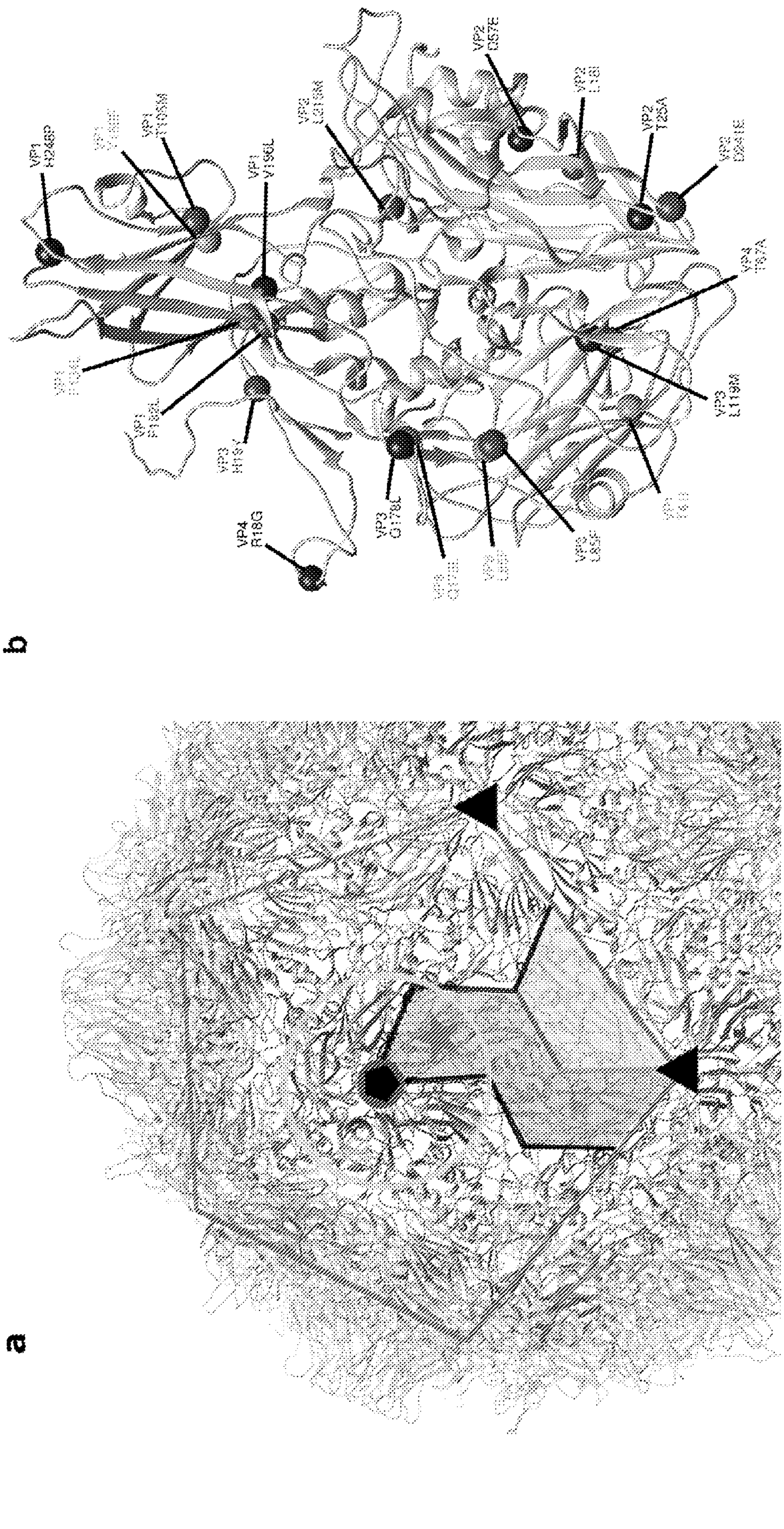
FIG. 2: Location of stabilising mutations in three poliovirus stereotypes. (a) A cartoon depiction of the type 1 (Mahoney strain) poliovirus capsid in grey focussing on the area surrounding an individual protomeric subunit (protein chains coloured VP1 blue, VP2 green and VP3 red). The capsid features described in Tables 6 and 7 are identified on the capsid as follows—yellow ring: canyon, cyan star: VP1 pocket, purple line: pentamer interface, black pentagon: five-fold axis, black triangle: three-fold axis, red circle VP3 beta-annulus, orange line: VP2/VP3 interface, black line: protomer interface and magenta line: VP1/VP2 interface. (b) an enlarged protomeric subunit in grey with the mutations for all three stereotypes shown color-coded as: blue: Mahoney-SC7 (type 1), green: MEF-SC5a (type 2) and red: Saukett-SC8 (type 3).

The poliovirus is a human enterovirus of the family Picornaviridae. The viral particle is approximately 30 nm in diameter and icosahedral in shape. The poliovirus genome is a single linear RNA molecule. This RNA molecule comprises a long, highly structured 5' end, which is does not code for a polypeptide product and contains six domains, I to VI. Several of these domains (including domain V) together comprise an Internal Ribosome Entry Site (IRES) which determines initiation of translation. The coding region of the poliovirus RNA is divided into two regions, one coding for structural proteins that make up the viral capsid, and the other coding for non-structural proteins such as viral proteases and a viral RNA dependent RNA polymerase. The 3' untranslated region is less complex than the 5' non-coding region.

The poliovirus RNA molecule is translated by the host cell as one long polypeptide which is then cleaved by viral proteases into individual viral proteins. The poliovirus capsid is encoded by the capsid coding region, P1. The P1 capsid precursor is further cleaved into the VP0, VP1 and VP3 proteins by a viral protease (3C or 3CD) with a final cleavage of VP0 into VP4 and VP2 occurring on RNA encapsidation by a mechanism that is not fully understood. The capsid of a complete poliovirus particle is icosahedral in shape, being formed of twelve pentamers. Each pentamer of a complete poliovirus particle consists of five protomers, with each protomer comprising a single copy of each of VP1, VP2, VP3 and VP4.

Prior to RNA encapsidation capsid proteins VP0, VP1 & VP3 are present within the infected cell in analogous protomer and pentamer subunits, as well as in icosahedral particles consisting of twelve pentamers, but containing no viral RNA. These particles are known as empty capsids. Empty capsids lack a number of inter-subunit interactions compared to infectious virus particles; these interactions are only formed after RNA encapsidation and cleavage of VP0 into VP2 and VP4 (the so-called maturation cleavage). These interactions play a major role in the thermostability of the infectious virus particle.

A complete poliovirus particle, also known as a poliovirus virion is the complete infective form of the poliovirus, comprising both the poliovirus capsid and the poliovirus RNA molecule. As defined herein, a poliovirus-like particle (VLP) is an empty poliovirus particle, i.e. a VLP comprises a poliovirus capsid, but lacks the poliovirus RNA molecule. A VLP of the invention may comprise or consist of a poliovirus capsid. Thus, the capsid of a VLP typically comprises twelve pentamers, each made of five protomers. Each protomer of a VLP typically comprises a single copy of each of VP0, VP1 and VP3. It should be noted that a VLP as defined herein cannot be derived from a complete poliovirus particle, for example by removal of the RNA.

As described herein, a VLP of the invention comprises a VP0, VP1 and VP3. Some of the stabilising modifications identified by the present inventors are referred to by their positions within the VP2 or VP4 of the mature poliovirus particle from which the VLPs of the invention were derived. In more detail, as described herein, the poliovirus VP0 is cleaved during virion assembly to produce VP2 and VP4. Thus, where reference is made herein to modifications at particular positions in VP2 and VP4, the positions of these modifications can readily be read onto the VP0 sequence in a straightforward manner. As a non-limiting example, 2025 in the Mahoney (type 1) strain is residue 25 of the Mahoney VP2 (SEQ ID NO: 2), which corresponds to residue 93 of Mahoney VP0 (SEQ ID NO: 5). Similarly, 4067 in the Saukett (type 3) strain is residue 67 of the Saukett VP4 (SEQ ID NO: 14), which corresponds to residue 67 of the Saukett VP0 (SEQ ID NO: 15). Thus, references herein to a residue within VP2 (e.g. 2025, 2057, 2067, 2197, 2139, 2215, 2016, 2018, 2124 and 2241) or VP4 (e.g. 4017, 4018, 4023, 4046, 4055, 4057, 4065 and 4067) could readily and interchangeably be referred to by the corresponding residue within the VP0 sequence of a VLP. This is clear from FIG. 1, which provides an alignment of various type 1, type 2 and type 3 poliovirus capsid precursor P1 polypeptide sequences, in which the VP0, VP2 and VP4 amino acid sequence are clearly indicated. For consistency with the conventional nomenclature for poliovirus, modifications that would be found within the mature VP2 and/or VP4 protein in a poliovirus virion are typically referred to herein by reference to their positions in VP2/VP4. However, as explained above, in the VLPs of the invention these modifications will in fact be found at corresponding positions within VP0.

Poliovirus particles express two distinct antigens. D antigen is associated mainly with infectious virus and C antigen with non-infectious particles in a different conformation, for example resulting from heating; wild-type empty capsids, outside the cell, are particularly prone to convert to C antigen specificity.

Empty poliovirus particles in a native ("D") conformation are produced by poliovirus and other picornaviruses seemingly as a necessary part of the assembly process, possibly to provide a reservoir of capsid subunits in a form that is resistant to cellular pathways that target unfolded or hydrophobic motifs for proteolytic degradation. Naturally occurring empty particles lack some of the intersubunit interactions present in mature virus particles and are dissociable into pentamer subunits, presumably so that they can then reassemble around the viral RNA during genome encapsidation. Hence, naturally occurring empty particles are extremely unstable and therefore unsuitable for vaccine production. Outside the cell these particles are easily converted at physiological temperature into a different, non-native antigenic conformation known as C-antigenic (or sometimes H-antigenic). The native D-antigenic form (sometimes known as N-antigenic) is responsible for inducing a protective immune response and the non-native C-antigenic form lacks protective immunogenicity.

To solve this problem, the present inventors have developed a method which allows the identification of modifications (typically mutations) within the poliovirus capsid which modulate capsid stability, particularly mutations which stabilise the native-antigenic poliovirus capsid.

Using this method, the present inventors have produced VLPs (i.e. empty viral particles) with the correct antigenic and immunogenic properties, but which comprise modifications in the poliovirus capsid which stabilise the capsid, and hence the VLPs. Thus, the VLPs of the invention typically: (i) are at least as stable as IPV; (ii) have the same antigenic structure as the native virus; and (iii) are at least as immunogenic as IPV.

The VLPs of the invention may be expressed by recombinant technology and may be used in the production of poliovirus vaccine without requiring infectious virus at any stage in vaccine production. Thus, the VLPs of the invention provide major advantages compared to the current IPV and OPV and production methods in terms of both safety and the properties of the vaccine product.

Poliovirus Serotypes

There are three known poliovirus serotypes: types 1, 2 and 3. Examples of wild-type polioviruses include Mahoney (type 1), MEF-1 (type 2) and Saukett (type 3). Live attenuated poliovirus strains were developed from wild-type strains by Sabin in the 1950s and are referred to as Sabin 1 (type 1), Sabin 2 (type 2) and Sabin 3 (type 3).

A VLP of the invention may be derived from any poliovirus serotype, i.e. serotype 1, 2 or 3. In addition, a VLP of the invention may be derived from a wild-type poliovirus or from a vaccine strain. Thus, a VLP of the invention may be derived from a type 1 wild-type strain (e.g. Mahoney), a type 1 vaccine strain (e.g. Sabin 1), a type 2 wild-type strain (e.g. MEF-1), a type 2 vaccine strain (e.g. Sabin 2), a type 3 wild-type strain (e.g. Saukett) or a type 3 vaccine strain (e.g. Sabin 3).

In the context of the present invention, a VLP may typically be considered to be derived from a particular poliovirus if the poliovirus capsid proteins, poliovirus polypeptide or corresponding poliovirus RNA molecule which encodes said poliovirus capsid protein(s) or poliovirus polypeptide of said poliovirus has been modified to comprise the one or more modifications disclosed herein. As a non-limiting example, a VLP of the invention is derived from Sabin 3 if it comprises the Sabin 3 capsid proteins (or is produced using the Sabin 3 polypeptide or the Sabin 3 RNA molecule) modified to include one or more of the modifications disclosed herein. For example, a VLP of the invention may be derived from a type 1 poliovirus, having: (a) a VP1 amino acid sequence corresponding to SEQ ID NO: 1, or a sequence which has at least 75%, at least 80%, at least 85%, at least 90%, at least 95%, at least 96%, at least 97%, at least 98%, at least 99% or more sequence identity with SEQ ID NO: 1; (b) a VP3 amino acid sequence corresponding to SEQ ID NO: 3, or a sequence which has at least 75%, at least 80%, at least 85%, at least 90%, at least 95%, at least 96%, at least 97%, at least 98%, at least 99% or more sequence identity with SEQ ID NO: 3; (c) a VP0 amino acid sequence corresponding to SEQ ID NO: 5, or a sequence which has at least 75%, at least 80%, at least 85%, at least 90%, at least 95%, at least 96%, at least 97%, at least 98%, at least 99% or more sequence identity with SEQ ID NO: 5; (d) a VP2 amino acid sequence corresponding to SEQ ID NO: 2, or a sequence which has at least 75%, at least 80%, at least 85%, at least 90%, at least 95%, at least 96%, at least 97%, at least 98%, at least 99% or more sequence identity with SEQ ID NO: 2; and/or (e) a VP4 amino acid sequence corresponding to SEQ ID NO: 4, or a sequence which has at least 75%, at least 80%, at least 85%, at least 90%, at least 95%, at least 96%, at least 97%, at least 98%, at least 99% or more sequence identity with SEQ ID NO: 4, or any combination thereof. A VLP of the invention may be derived from a type 1 poliovirus, having a P1 amino acid sequence corresponding to SEQ ID NO: 16 or 17, or a sequence which has at least 75%, at least 80%, at least 85%, at least 90%, at least 95%, at least 96%, at least 97%, at least 98%, at least 99% or more sequence identity with SEQ ID NO: 16 or 17. Typically a type 1 VLP of the invention has a VP1 amino acid sequence corresponding to SEQ ID NO: 1, or a sequence which has at least 75%, at least 80%, at least 85%, at least 90%, at least 95%, at least 96%, at least 97%, at least 98%, at least 99% or more sequence identity with SEQ ID NO: 1; a VP3 amino acid sequence corresponding to SEQ ID NO: 3, or a sequence which has at least 75%, at least 80%, at least 85%, at least 90%, at least 95%, at least 96%, at least 97%, at least 98%, at least 99% or more sequence identity with SEQ ID NO: 3; and a VP0 amino acid sequence corresponding to SEQ ID NO: 5, or a sequence which has at least 75%, at least 80%, at least 85%, at least 90%, at least 95%, at least 96%, at least 97%, at least 98%, at least 99% or more sequence identity with SEQ ID NO: 5. Preferably said VP1, VP3 and/or VP0 amino acid sequences have at least 95%, at least 96%, at least 97%, at least 98%, at least 99% or more sequence identity with the recited SEQ ID NO. Preferably a type 1 VLP of the invention has a VP1 amino acid sequence corresponding to SEQ ID NO: 1, or a sequence which has at least 75%, at least 80%, at least 85%, at least 90%, at least 95%, at least 96%, at least 97%, at least 98%, at least 99% or more sequence identity with SEQ ID NO: 1; a VP3 amino acid sequence corresponding to SEQ ID NO: 3, or a sequence which has at least 75%, at least 80%, at least 85%, at least 90%, at least 95%, at least 96%, at least 97%, at least 98%, at least 99% or more sequence identity with SEQ ID NO: 3; a VP2 amino acid sequence corresponding to SEQ ID NO: 2, or a sequence which has at least 75%, at least 80%, at least 85%, at least 90%, at least 95%, at least 96%, at least 97%, at least 98%, at least 99% or more sequence identity with SEQ ID NO: 2; and a VP4 amino acid sequence corresponding to SEQ ID NO: 4, or a sequence which has at least 75%, at least 80%, at least 85%, at least 90%, at least 95%, at least 96%, at least 97%, at least 98%, at least 99% or more sequence identity with SEQ ID NO: 4. Preferably said VP1, VP3, VP2 and/or VP4 amino acid sequences have at least 95%, at least 96%, at least 97%, at least 98%, at least 99% or more sequence identity with the recited SEQ ID NO. Thus, a type 1 VLP of the invention may have a P1, VP0, VP1, VP2, VP3 and/or VP4 (or any combination thereof) with an amino acid sequence as defined above, but having one or more stabilising modification as described herein.

A VLP of the invention may be derived from a type 2 poliovirus, having: (a) a VP1 amino acid sequence corresponding to SEQ ID NO: 6, or a sequence which has at least 75%, at least 80%, at least 85%, at least 90%, at least 95%, at least 96%, at least 97%, at least 98%, at least 99% or more sequence identity with SEQ ID NO: 6; (b) a VP3 amino acid sequence corresponding to SEQ ID NO: 8, or a sequence which has at least 75%, at least 80%, at least 85%, at least 90%, at least 95%, at least 96%, at least 97%, at least 98%, at least 99% or more sequence identity with SEQ ID NO: 8; (c) a VP0 amino acid sequence corresponding to SEQ ID NO: 10, or a sequence which has at least 75%, at least 80%, at least 85%, at least 90%, at least 95%, at least 96%, at least 97%, at least 98%, at least 99% or more sequence identity with SEQ ID NO: 10; (d) a VP2 amino acid sequence corresponding to SEQ ID NO: 7, or a sequence which has at least 75%, at least 80%, at least 85%, at least 90%, at least 95%, at least 96%, at least 97%, at least 98%, at least 99% or more sequence identity with SEQ ID NO: 7; and/or (e) a VP4 amino acid sequence corresponding to SEQ ID NO: 9, or a sequence which has at least 75%, at least 80%, at least 85%, at least 90%, at least 95%, at least 96%, at least 97%, at least 98%, at least 99% or more sequence identity with SEQ ID NO: 9, or any combination thereof. A VLP of the invention may be derived from a type 2 poliovirus, having a P1 amino acid sequence corresponding to SEQ ID NO: 18 or 19, or a sequence which has at least 75%, at least 80%, at least 85%, at least 90%, at least 95%, at least 96%, at least 97%, at least 98%, at least 99% or more sequence identity with SEQ ID NO: 18 or 19. Typically a type 2 VLP of the invention has a VP1 amino acid sequence corresponding to SEQ ID NO: 6, or a sequence which has at least 75%, at least 80%, at least 85%, at least 90%, at least 95%, at least 96%, at least 97%, at least 98%, at least 99% or more sequence identity with SEQ ID NO: 6; a VP3 amino acid sequence corresponding to SEQ ID NO: 8, or a sequence which has at least 75%, at least 80%, at least 85%, at least 90%, at least 95%, at least 96%, at least 97%, at least 98%, at least 99% or more sequence identity with SEQ ID NO: 8; and a VP0 amino acid sequence corresponding to SEQ ID NO: 10, or a sequence which has at least 75%, at least 80%, at least 85%, at least 90%, at least 95%, at least 96%, at least 97%, at least 98%, at least 99% or more sequence identity with SEQ ID NO: 10. Preferably said VP1, VP3 and/or VP0 amino acid sequences have at least 95%, at least 96%, at least 97%, at least 98%, at least 99% or more sequence identity with the recited SEQ ID NO. Preferably a type 2 VLP of the invention has a VP1 amino acid sequence corresponding to SEQ ID NO: 6, or a sequence which has at least 75%, at least 80%, at least 85%, at least 90%, at least 95%, at least 96%, at least 97%, at least 98%, at least 99% or more sequence identity with SEQ ID NO: 6; a VP3 amino acid sequence corresponding to SEQ ID NO: 8, or a sequence which has at least 75%, at least 80%, at least 85%, at least 90%, at least 95%, at least 96%, at least 97%, at least 98%, at least 99% or more sequence identity with SEQ ID NO: 8; a VP2 amino acid sequence corresponding to SEQ ID NO: 7, or a sequence which has at least 75%, at least 80%, at least 85%, at least 90%, at least 95%, at least 96%, at least 97%, at least 98%, at least 99% or more sequence identity with SEQ ID NO: 7; and a VP4 amino acid sequence corresponding to SEQ ID NO: 9, or a sequence which has at least 75%, at least 80%, at least 85%, at least 90%, at least 95%, at least 96%, at least 97%, at least 98%, at least 99% or more sequence identity with SEQ ID NO: 9. Preferably said VP1, VP3, VP2 and/or VP4 amino acid sequences have at least 95%, at least 96%, at least 97%, at least 98%, at least 99% or more sequence identity with the recited SEQ ID NO. Thus, a type 2 VLP of the invention may have a P1, VP0, VP1, VP2, VP3 and/or VP4 (or any combination thereof) with an amino acid sequence as defined above, but having one or more stabilising modification as described herein.

A VLP of the invention may be derived from a type 3 poliovirus, having: (a) a VP1 amino acid sequence corresponding to SEQ ID NO: 11, or a sequence which has at least 75%, at least 80%, at least 85%, at least 90%, at least 95%, at least 96%, at least 97%, at least 98%, at least 99% or more sequence identity with SEQ ID NO: 11; (b) a VP3 amino acid sequence corresponding to SEQ ID NO: 13, or a sequence which has at least 75%, at least 80%, at least 85%, at least 90%, at least 95%, at least 96%, at least 97%, at least 98%, at least 99% or more sequence identity with SEQ ID NO: 13; (c) a VP0 amino acid sequence corresponding to SEQ ID NO: 15, or a sequence which has at least 75%, at least 80%, at least 85%, at least 90%, at least 95%, at least 96%, at least 97%, at least 98%, at least 99% or more sequence identity with SEQ ID NO: 15; (d) a VP2 amino acid sequence corresponding to SEQ ID NO: 12, or a sequence which has at least 75%, at least 80%, at least 85%, at least 90%, at least 95%, at least 96%, at least 97%, at least 98%, at least 99% or more sequence identity with SEQ ID NO: 12; and/or (e) a VP4 amino acid sequence corresponding to SEQ ID NO: 14, or a sequence which has at least 75%, at least 80%, at least 85%, at least 90%, at least 95%, at least 96%, at least 97%, at least 98%, at least 99% or more sequence identity with SEQ ID NO: 14, or any combination thereof. A VLP of the invention may be derived from a type 3 poliovirus, having a P1 amino acid sequence corresponding to SEQ ID NO: 20 or 21, or a sequence which has at least 75%, at least 80%, at least 85%, at least 90%, at least 95%, at least 96%, at least 97%, at least 98%, at least 99% or more sequence identity with SEQ ID NO: 20 or 21. Typically a type 3 VLP of the invention has a VP1 amino acid sequence corresponding to SEQ ID NO: 11, or a sequence which has at least 75%, at least 80%, at least 85%, at least 90%, at least 95%, at least 96%, at least 97%, at least 98%, at least 99% or more sequence identity with SEQ ID NO: 11; a VP3 amino acid sequence corresponding to SEQ ID NO: 13, or a sequence which has at least 75%, at least 80%, at least 85%, at least 90%, at least 95%, at least 96%, at least 97%, at least 98%, at least 99% or more sequence identity with SEQ ID NO: 13; and a VP0 amino acid sequence corresponding to SEQ ID NO: 15, or a sequence which has at least 75%, at least 80%, at least 85%, at least 90%, at least 95%, at least 96%, at least 97%, at least 98%, at least 99% or more sequence identity with SEQ ID NO: 15. Preferably said VP1, VP3 and/or VP0 amino acid sequences have at least 95%, at least 96%, at least 97%, at least 98%, at least 99% or more sequence identity with the recited SEQ ID NO. Preferably a type 3 VLP of the invention has a VP1 amino acid sequence corresponding to SEQ ID NO: 11, or a sequence which has at least 75%, at least 80%, at least 85%, at least 90%, at least 95%, at least 96%, at least 97%, at least 98%, at least 99% or more sequence identity with SEQ ID NO: 11; a VP3 amino acid sequence corresponding to SEQ ID NO: 13, or a sequence which has at least 75%, at least 80%, at least 85%, at least 90%, at least 95%, at least 96%, at least 97%, at least 98%, at least 99% or more sequence identity with SEQ ID NO: 13; a VP2 amino acid sequence corresponding to SEQ ID NO: 12, or a sequence which has at least 75%, at least 80%, at least 85%, at least 90%, at least 95%, at least 96%, at least 97%, at least 98%, at least 99% or more sequence identity with SEQ ID NO: 12; and a VP4 amino acid sequence corresponding to SEQ ID NO: 14, or a sequence which has at least 75%, at least 80%, at least 85%, at least 90%, at least 95%, at least 96%, at least 97%, at least 98%, at least 99% or more sequence identity with SEQ ID NO: 14. Preferably said VP1, VP3, VP2 and/or VP4 amino acid sequences have at least 95%, at least 96%, at least 97%, at least 98%, at least 99% or more sequence identity with the recited SEQ ID NO. Thus, a type 3 VLP of the invention may have a P1, VP0, VP1, VP2, VP3 and/or VP4 (or any combination thereof) with an amino acid sequence as defined above, but having one or more stabilising modification as described herein.

Structure of the Poliovirus-Like Particle (VLP)

The present inventors are the first to provide a stabilised VLP suitable for use in a poliovirus vaccine. Said VLP has utility in poliovirus vaccines as it has the necessary stability and immunogenicity characteristics as defined herein. These characteristics are conferred by the presence of one or more modifications within the capsid of the VLP, relative to the poliovirus from which the VLP is derived.

Accordingly, the invention provides a VLP comprising at least one modification relative to the poliovirus particle from which the VLP is derived, wherein said at least one modification stabilises the VLP.

A VLP of the invention may comprise one or more, two or more, three or more, four or more, five or more, six or more, seven or more, eight or more, nine or more, ten or more, or more modifications relative to the poliovirus particle from which the VLP is derived, provided that said modifications (independently or in combination) stabilise the VLP relative to the poliovirus particle from which the VLP is derived. Preferably a VLP of the invention comprises at least three modifications relative to the poliovirus particle from which the VLP is derived, wherein said modifications stabilise the VLP.

Any and all combinations of modifications, particularly amino acid mutations/substitutions at the preferred amino acid residues described herein within any of the identified domains of the VLP is encompassed by the present invention, provided that the resulting VLP is stable and retains the necessary immunogenic properties as defined herein. In other words, reference to a VLP of the invention is a reference to a stable and immunogenic VLP.

The poliovirus empty capsid is made up of multiple copies of the VP0, VP1, and VP3 proteins, as described herein.

The multiple capsid proteins assemble to form a capsid with icosahedral symmetry, which comprises several distinct features/regions as follows:

- interfaces between the different capsid proteins, VP0, VP1 and VP3 (corresponding to VP2 and VP4, VP1 and VP3 in the mature poliovirus virion), e.g. interfaces between VP0 and VP1, VP0 and VP3 and/or VP1 and VP3 (i.e. interfaces between VP1 and VP2; VP1 and VP3; VP1 and VP4; VP2 and VP3; VP2 and VP4; and VP3 and VP4 in the mature poliovirus virion);
- interfaces between protomer subunits;
- interfaces between pentamer subunits;
- a pocket domain containing a hydrophobic molecule (e.g. fatty acid);
- an internal polypeptide network linking subunits; and
- a depression in the outer surface known as the canyon.

These domains are well-known in the field of poliovirus research, and indeed are common to all the Picornaviruses (see, for example Ehrenfeld, Domingo and Roos (2010) *The Picronaviruses*, Washington, DC: ASM Press, chapter 10, "Virion Structure" by Fry, E. E. and Stuart, D. I.; and Koch, F. and Koch, G. (1985) *The Molecular Biology of Poliovirus*, New York: Springer-Verlag Wien, chapter 3 "Composition and Structure of the Virion" and chapter 10 "Assembly of the Virion", both of which are herein incorporated by reference in their entirety). Further, these domains can be readily identified using commercially available software and published poliovirus crystal structures, including, but not limited to Protein Data Bank (PDB) ID No: 1HXS (Mahoney strain, deposited 16 Jan. 2001), PDB ID No: 1EAH (type 2 Lansing strain, deposited 22 Jul. 1997) and PDB ID No: 1PVC (Sabin 3 strain, deposited 30 Mar. 1995). PDB entries are freely available from the NCBI website (www.ncbi.nlm.nih.gov/structure). Thus, a reference to any one of the above domains may be interpreted as in the context of any known poliovirus crystal structure, including PDB ID Nos: 1HXS, LEAH and/or 1PVC. As a non-limiting example, a reference to a protomer interface, pentamer interface and/or pocket domain may be a reference to a protomer interface, pentamer interface and/or pocket domain as defined by any one of PDB ID Nos: 1HXS, LEAH and/or 1PVC.

A VLP of the invention may comprise one or more modification in one or more of these regions. A VLP of the invention may comprise one or more modification in any one, any two, any three, any four, any five, any six, any seven, any eight or more of these regions. Typically a VLP of the invention comprises one or more modification in a protomer interface and/or one or more modification in a pentamer interface, preferably one or more modification in a protomer interface and one or more modification in a pentamer interface, and optionally one or more modification in any of the other domains or combination thereof. As a non-limiting example, a VLP of the invention may comprise one or more modification in the pocket domain, the interface between one or more protomer subunits (also referred to herein as a protomer interface), the interface between one or more pentamer subunits (also referred to herein as a pentamer interface), the VP2/VP3 interface (as defined in the mature poliovirus virion, corresponding to the VP0/VP3 interface in a VLP, such the terms VP0/VP3 interface and VP2/VP3 interface may be used interchangeably herein), the internal network or the canyon.

Alternatively, a VLP of the invention may comprise one or more modification in any two, any three, any four, any five or all six of these domains. As a non-limiting example, a VLP of the invention may comprise one or more modification in a protomer interface, one or more modification in a pentamer interface, and optionally one or more modification in the pocket domain.

Typically, a VLP of the invention comprises at least three modifications, preferably at least four modifications, more preferably at least five modifications and even more preferably at least six modifications relative to the poliovirus from which the VLP is derived, and preferably comprises at least one modification in each of a protomer interface a pentamer interface, with optionally at least one modification in the pocket domain.

A VLP of the invention may comprise (a) a protomer interface; and (b) a pentamer interface; wherein each of (a) and (b) comprises at least one modification relative to the poliovirus particle from which the VLP is derived. For example, the VLP may comprise one, two, three, four, five or more modifications in the protomer interface and/or one, two, three, four, five or more modifications in the pentamer interface, provided that each of the protomer interface and pentamer interface comprises at least one modification (as defined herein), preferably at least one amino acid substitution. Typically said VLP comprises at least three modifications relative to the poliovirus particle from which the VLP is derived.

As a non-limiting example, a VLP of the invention may comprise (a) a pocket domain; (b) a protomer interface; and (c) a pentamer interface; wherein each of (a) to (c) comprises at least one modification relative to the poliovirus particle from which the VLP is derived. For example, the VLP may comprise one, two, three, four, five or more modifications in the pocket domain, one, two, three, four, five or more modifications in the protomer interface and/or one, two, three, four, five or more modifications in the pentamer interface, provided that each of the pocket domain, protomer interface and pentamer interface comprises at least one modification (as defined herein) preferably at least one amino acid substitution.

Particular amino acid residues in the capsid proteins of each of type 1, type 2 and type 3 polioviruses which may be modified to produce stabilised VLP have been identified by the present inventors and are described herein. The present invention encompasses any combination of modifications at any combination of the disclosed amino acid residues within the type 1, type 2 and type 3 poliovirus capsid proteins, provided the combination of modifications results in a VLP with the necessary properties (e.g. stability, antigenicity and/or immunogenicity) to make it suitable for use as a polio vaccine. As an example, the notation 1134 refers to residue 134 of VP1, or VP1-134). Similarly, the notation 1132 refers to residue 132 of VP1, also referred to as VP1-132.

Where reference is made to a given amino acid residue within a particular poliovirus serotype, the invention also encompasses modifications at corresponding positions within the other two serotypes. As a non-limiting example, residue 1134 in a type 1/2 serotype poliovirus corresponds to residue 1132 in a type 3 serotype poliovirus (there is a two-amino acid deletion in VP1 of type 3 poliovirus (residues 15-16) compared with types 1 and 2), such that a reference to a modification at a residue corresponding to residue 1134 of a type 2 poliovirus also encompasses a modification at residue 1132 of a type 3 poliovirus. There are two other insertions/deletions in VP1 sequences of the three serotypes so that the numbering of equivalent residues is as follows:

| Equivalent residues in VP1 sequences | | |
|---|---|---|
| Type 1 | Type 2 | Type 3 |
| 1-14 | 1-14 | 1-14 |
| 17-221 | 17-221 | 15-219 |
| 222-289 | 222-289 | 221-288 |
| 291-302 | 290-301 | 289-300 |

Thus, a reference to a mutation or modification at specific residue in a type 1 or 2 VLP encompasses not only said mutation in the type 1 or 2 VLP, but also the same mutation at the corresponding residue in a type 3 VLP (e.g. subtracting 2 from the position of in VP1 of a type 1 or 2 VLP between residues 17 and 221 will give the corresponding position in a type 3 VLP). Vice versa, a reference to a mutation or modification at specific residue in a type 3 VLP encompasses not only said mutation in the type 3 VLP, but also the same mutation at the corresponding residue in a type 1 or 2 VLP, which may not have the same number if it is in VP1 (the corresponding position can be derived from the Table above). Any mutation described herein in relation to any particular poliovirus type is therefore also disclosed in the context of the other poliovirus type. In particular, a mutation at a specific residue in a type 1 poliovirus/VLP is also disclosed in the context of a type 2 or type 3 poliovirus/VLP; a mutation at a specific residue in a type 2 poliovirus/VLP is also disclosed in the context of a type 1 or type 3 poliovirus/VLP; and a mutation at a specific residue in a type 3 poliovirus/VLP is also disclosed in the context of a type 1 or type 2 poliovirus/VLP.

A VLP of the invention is sufficiently stable to be suitable for use in a polio vaccine. The stability of a VLP may be measured relative to a control. Typically the control is a reference preparation of IPV which contains an unmodified form of the poliovirus from which the VLP is derived.

Typically the unmodified form of the poliovirus in the reference preparation has been treated with formaldehyde. As a non-limiting example, if a VLP of the invention is derived from Mahoney, it will typically be at least as stable as the type 1 component of IPV, i.e. formaldehyde-treated Mahoney virus. The VLP of the invention may be at least as stable as the control, at least 10%, at least 20%, at least 30%, at least 40%, at least 50%, at least 60%, at least 70%, at least 80%, at least 90%, at least 100% or more stable than the control.

The stability of a VLP may be measured using any appropriate technique. Standard techniques are known in the art, including, but not limited to retention of native D antigenic structure on heating (expressed as the temperature at which ELISA reactivity with D antigen-specific monoclonal antibodies (MAbs) is reduced by 50% on a 10 minute incubation) or retention of native D antigenic structure on long-term incubation at 37° C. (denoted as the length of time in days after which ELISA reactivity with D antigen-specific MAbs is reduced by 50%). For example, the temperature at which ELISA reactivity with D antigen-specific monoclonal antibodies (MAbs) is reduced by 50% on a 10 minute incubation for a VLP of the invention may be greater than 45° C., greater than 46° C., greater than 47° C., greater than 48° C., greater than 49° C., greater than 50° C., greater than 51° C., greater than 52° C., greater than 53° C., greater than 54° C., greater than 55° C., greater than 56° C., or more. Typically, the temperature at which ELISA reactivity with D antigen-specific monoclonal antibodies (MAbs) is reduced by 50% on a 10 minute incubation for a VLP of the invention is greater than 50° C., greater than 51° C., greater than 52° C., greater than 53° C., greater than 54° C., greater than 55° C., greater than 56° C., or more; preferably greater than 54° C., greater than 55° C., greater than 56° C., or more.

In a preferred embodiment, a VLP of the invention is stable enough not to require cold storage, which is advantageous in terms of supply/distribution. Accordingly, the stability of a VLP of the invention may be quantified in terms of D antigen loss when exposed to elevated temperatures (e.g. 37° C.) for prolonged periods. Typically a VLP of the invention retains at least 50% of its activity, at least 51%, at least 52%, at least 53%, at least 54%, at least 55%, at least 56%, at least 57%, at least 58%, at least 59%, at least 60%, at least 70%, at least 75%, at least 80%, at least 81%, at least 82%, at least 83%, at least 84%, at least 85%, at least 86%, at least 87%, at least 88%, at least 89%, at least 90% or more of its activity after storage at 37° C. for at least 50 days, at least 100 days, at least 150 days, at least 180 days or more (compared with the corresponding VLP stored at 4° C. for the same period). Preferably a VLP of the invention retains at least 80%, at least 81%, at least 82%, at least 83%, at least 84%, at least 85%, at least 86%, at least 87%, at least 88%, at least 89%, at least 90% or more of its activity after storage at 37° C. for at least 50 days (compared with the corresponding VLP stored at 4° C. for the same period), and/or at least 50%, at least 51%, at least 52%, at least 53%, at least 54%, at least 55%, at least 56%, at least 57%, at least 58%, at least 59%, at least 60% or more of its activity after storage at 37° C. for at least 180 days (compared with the corresponding VLP stored at 4° C. for the same period).

A VLP of the invention is sufficiently immunogenic to be suitable for use in a polio vaccine. The immunogenicity of a VLP may be measured relative to a control. Typically the control is reference preparation of IPV which contains an unmodified form of the poliovirus from which the VLP is derived or the current IPV of the relevant serotype. Typically the unmodified form of the poliovirus in the reference preparation has been treated with formaldehyde. As a non-limiting example, if a VLP of the invention is derived from Mahoney, it will typically be at least as immunogenic as the type 1 component of IPV i.e. formaldehyde-treated Mahoney virus. The VLP of the invention may be at least as immunogenic, and preferably at least 1.5 times, at least 2 times, at least 2.5 times, at least 3 times, at least 3.5 times, at least 4 times, at least 4.5 times, at least 5 times, at least 6 times, at least 7 times, at least 8 times, at least 9 times, at least 10 times or more immunogenic than the control. Preferably the VLP of the invention may be at least as immunogenic, and preferably at least 4 times, at least 4.5 times, at least 5 times, at least 6 times, at least 7 times, at least 8 times, at least 9 times, at least 10 times or more immunogenic than the control. The immunogenicity of a VLP may be measured using any appropriate technique. Standard techniques are known in the art, including, but not limited to C/D antigen ELISA and in vivo potency testing in rats (a relative potency of ≥1.0 signifies immunogenicity at least as good as that of an international reference preparation).

Modifications

As described herein, the term modification encompasses modifications at both the nucleic acid and amino acid level. Typically the modification refers to a modification at the amino acid level. Each amino acid modification may be independently selected from an amino acid substitution, an amino acid insertion, and an amino acid deletion. In preferred embodiments, said amino acid modification is an amino acid substitution, also referred to interchangeably herein as an amino acid mutation.

In an amino acid substitution, an amino acid residue that forms part of the poliovirus capsid protein amino acid sequence is replaced with a different amino acid residue. The replacement amino acid residue may be one of the 20 standard amino acids in the Table below.

| AMINO ACID | | | SIDE CHAIN |
|---|---|---|---|
| Aspartic acid | Asp | D | Charged (acidic) |
| Glutamic acid | Glu | E | Charged (acidic) |
| Arginine | Arg | R | Charged (basic) |
| Lysine | Lys | K | Charged (basic) |
| Histidine | His | H | Uncharged (polar) |
| Asparagine | Asn | N | Uncharged (polar) |
| Glutamine | Gln | Q | Uncharged (polar) |
| Serine | Ser | S | Uncharged (polar) |
| Threonine | Thr | T | Uncharged (polar) |
| Tyrosine | Tyr | Y | Uncharged (polar) |
| Methionine | Met | M | Uncharged (polar) |
| Tryptophan | Trp | W | Uncharged (polar) |
| Cysteine | Cys | C | Uncharged (polar) |
| Alanine | Ala | A | Uncharged (hydrophobic) |
| Glycine | Gly | G | Uncharged (hydrophobic) |
| Valine | Val | V | Uncharged (hydrophobic) |
| Leucine | Leu | L | Uncharged (hydrophobic) |
| Isoleucine | Ile | I | Uncharged (hydrophobic) |
| Proline | Pro | P | Uncharged (hydrophobic) |
| Phenylalanine | Phe | F | Uncharged (hydrophobic) |

The following amino acids are considered charged amino acids: aspartic acid (negative), glutamic acid (negative), arginine (positive), and lysine (positive).

The following amino acids are considered uncharged, polar (meaning they can participate in hydrogen bonding) amino acids: asparagine, glutamine, histidine, serine, threonine, tyrosine, cysteine, methionine, and tryptophan.

The following amino acids are considered uncharged, hydrophobic amino acids: alanine, valine, leucine, isoleucine, phenylalanine, proline, and glycine.

Alternatively, the replacement amino acid in an amino acid substitution may be a non-standard amino acid (an amino acid that is not part of the standard set of 20 described above). By way of example, the replacement amino acid may be a basic non-standard amino acid, e.g. L-Ornithine, L-2-amino-3-guanidinopropionic acid, or D-isomers of Lysine, Arginine and Ornithine). Methods for introducing non-standard amino acids into proteins are known in the art, and include recombinant protein synthesis using *E. coli* auxotrophic expression hosts.

In an amino acid insertion, an additional amino acid residue (one that is not normally present) is incorporated into the polypeptide amino acid sequence, thus increasing the total number of amino acid residues in said sequence. In an amino acid deletion, an amino acid residue is removed from the polypeptide amino acid sequence, thus reducing the total number of amino acid residues in said sequence.

Methods for modifying proteins by substitution, insertion or deletion of amino acid residues are known in the art. By way of example, amino acid modifications may be introduced by modification of a DNA sequence encoding the polypeptide. This can be achieved using standard molecular cloning techniques, for example by site-directed mutagenesis where short strands of DNA (oligonucleotides) coding for the desired amino acid(s) are used to replace the original coding sequence using a polymerase enzyme, or by inserting/deleting parts of the gene with various enzymes (e.g., ligases and restriction endonucleases). Alternatively a modified gene sequence can be chemically synthesised.

An each amino acid substation according to the present invention may independently be a conservative substitution, i.e. a substitution by any amino acid with the same class of side chain (e.g. acidic with acidic, basic with basic, polar with polar, hydrophobic with hydrophobic, as defined in the table above). Alternatively, each amino acid substation of the invention may independently be a non-conservative substitution, i.e. a substitution by any amino acid with a different class of side chain (e.g. acidic with basic, polar or hydrophobic; basic with acid, polar or hydrophobic; polar with acidic, basic or hydrophobic; or hydrophobic with acidic, basic or polar, as defined in the table above). As non-limiting examples, the at least one amino acid modification may be selected from: substitution of an acidic amino acid residue with a basic amino acid residue; substitution of an acidic amino acid residue with an uncharged amino acid residue; substitution of an uncharged amino acid residue with a basic amino acid residue; insertion of a basic amino acid residue; and deletion of an acidic amino acid residue.

In a preferred embodiment, the at least one amino acid modification is typically a substitution, which advantageously maintains the same number of amino acid residues in the polypeptide. For some amino acid residues, the preferred modification is a deletion. An example of a preferred modification which is a deletion is deletion of the leucine residue at position 1104 (i.e. residue 104 of VP1) in a type 2 VLP, or the corresponding position in a type 1 or type 3 VLP (see Table 2).

A VLP of the invention may comprise one or more, two or more, three or more, four or more, five or more, six or more, seven or more, eight or more, nine or more, ten or more, or more modifications at one or more of the positions listed in Table 1, 2 or 3 below, or any combination thereof, and preferably at least four modifications, more preferably at least five modifications and even more preferably at least six modifications at positions listed in Tables 1, 2 or 3 below. In particular, a VLP of the invention may comprise one or more, two or more, three or more, four or more, five or more, six or more, seven or more, eight or more, nine or more, ten or more, or more of the particular modifications listed in Table 1, 2 or 3 below, or any combination thereof, and preferably at least four modifications, more preferably at least five modifications and even more preferably at least six modifications at positions listed in Tables 1, 2 or 3 below. Alternatively or in addition, a VLP of the invention may comprise one or more additional stabilising modification, which may be any modification identified by a method of the invention as described herein.

A VLP of the invention typically comprises at least one (preferably one or two modifications in a protomer interface and/or at least one (preferably one or two) modifications in a pentamer interface, optionally with at least one (preferably one or two) modifications in the pocket domain. Said VLP may further comprise one or more additional modification at one or more of the positions listed in Table 1, 2 or 3 below, or any combination thereof, such as at least one (preferably one) modification in a VP2/VP3 interface and/or at least one (preferably one, two or three) modifications in an internal network and/or at least one (preferably one) modification in the canyon domain.

A type 1 VLP of the invention may comprise one or more, two or more, three or more, four or more, five or more, six or more, seven or more, eight or more, nine or more, ten or more, or more modifications at one or more of the positions listed in Table 1 below, relative to the poliovirus particle from which the VLP is derived. The particular mutation at any one of these positions may be as given in Table 1 below.

A type 1 VLP of the invention may comprise any combination of modifications at any combination of the disclosed amino acid positions as set out in Table 1 below, provided the combination of modifications results in a VLP with the necessary properties (e.g. stability, antigenicity and/or immunogenicity) to make it suitable for use as a polio vaccine. In some embodiments, a VLP may comprise at most two modifications in any particular region, regardless of the total number of modifications in said VLP. A type 1 VLP of the invention may comprise multiple modifications in the pentamer interface, for example at least one, at least two, at least three, at least four or more modifications in the pentamer interface, for example at any of the positions in the pentamer interface listed in Table 1 below, or any combination thereof, preferably any of the specific mutations in the pentamer interface listed in Table 1 below, or any combination thereof.

A type 1 VLP of the invention typically comprises at least one modification in a protomer interface and at least one modification in a pentamer interface, optionally with at least one modification in a pocket domain. Preferably a type 1 VLP of the invention comprises at least one (preferably one or two modifications in a protomer interface and/or at least one (preferably one or two) modifications in a pentamer interface, optionally with at least one (preferably one) modification in the pocket domain and/or at least one (preferably one) modification in a VP2/VP3 interface and/or at least one (preferably one) modification in an internal network. As a non-limiting example, a type 1 VLP of the invention may comprise six modifications relative to the poliovirus particle from which it is derived: two modifications in a protomer interface (e.g. at 3118 and 1248), two modifications in a pentamer interface (e.g. at 2025 and 2057), one modification at a VP2/VP3 interface (e.g. at 3119) and one modification in a internal network (e.g. at 4018). As a further example, a type one VLP of the invention may comprise these six modifications and in addition a seventh modification in a pocket domain (e.g. at 1196).

TABLE 1

The position of serotype 1 capsid stabilising modifications and particular stabilising mutations

| Region | Position of modification | Stabilising mutation |
|---|---|---|
| Protomer interface | 3108 | T3108A |
| | 3178 | Q3178L |
| | 1101 | K1101E |
| | 1168 | E1168K |
| | 1231 | A1231V, A1231T |
| | 1232 | A1232V |
| | 1236 | D1236Y |
| | 1247 | D1247Y |
| | 1248 | H1248P, H1248L |
| Pentamer interface | 2014 | L2014M |
| | 2025 | T2025A |
| | 2057 | D2057E |
| | 2067 | D2067N |
| | 2251 | L2251V |
| | 2252 | T2252S |
| | 1040 | E1040K |
| | 1041 | I1041V |
| | 1218 | K1218R |
| Hydrophobic pocket | 1196 | V1196L |
| Internal network: around 5-fold axis | 4017 | N4017T |
| | 4018 | R4018G |
| | 4023 | S4023Y |
| | 4046 | F4046L |
| | 4055 | E4055Q |
| | 1009 | M1009V |
| VP2/VP3 interface | 1295 | S1295P |
| | 2197 | I2197V |
| | 3119 | L3119M |
| VP1/VP2 interface | 2127 | V2127I |
| Canyon | 1090 | M1090L |
| | 1252 | K1252T |
| Other | 3059 | A3059D |
| | 2159 | G2159S |
| | 2168 | S2168A |
| | 2228 | G2228V |

A type 2 VLP of the invention may comprise one or more, two or more, three or more, four or more, five or more, six or more, seven or more, eight or more, nine or more, ten or more, or more modifications at one or more of the positions listed in Table 2 below, relative to the poliovirus particle from which the VLP is derived. The particular mutation at any one of these positions may be as given in Table 2 below.

A type 2 VLP of the invention may comprise any combination of modifications at any combination of the disclosed amino acid positions as set out in Table 2 below, provided the combination of modifications results in a VLP with the necessary properties (e.g. stability, antigenicity and/or immunogenicity) to make it suitable for use as a polio vaccine. In some embodiments, a VLP may comprise at most two modifications in any particular region, regardless of the total number of modifications in said VLP. A type 2 VLP of the invention may comprise multiple modifications in the pocket domain, for example at least one, at least two, at least three, at least four or more modifications in the pocket domain, for example at any of the positions in the pocket domain listed in Table 2 below, or any combination thereof, preferably any of the specific mutations in the pocket domain listed in Table 2 below, or any combination thereof.

A type 2 VLP of the invention typically comprises at least one modification in a protomer interface and at least one modification in a pentamer interface. Preferably a type 2 VLP of the invention comprises at least one (preferably one) modification in a protomer interface and/or at least one (preferably one or two) modifications in a pentamer interface, optionally with at least one (preferably one or two) modifications in the pocket domain, and/or at least one (preferably one) modification in the internal network. As a non-limiting example, a type 2 VLP of the invention may comprise five modifications relative to the poliovirus particle from which it is derived: one modification in a protomer interface (e.g. at 3178), two modifications in a pentamer interface (e.g. at 3085 and 1041), and two modifications in a pocket domain (e.g. at 1134 and 1159). As another non-limiting example, a type 2 VLP of the invention may comprise six modifications relative to the poliovirus particle from which it is derived: two modifications in a protomer interface (e.g. at 3178 and 1107), one modification in a pentamer interface (e.g. at 2057), two modifications in a pocket domain (e.g. at 1134 and 1183) and one modification in the internal network (e.g. at 4057).

TABLE 2

The position of serotype 2 capsid stabilising modifications and particular stabilising mutations

| Region | Position of modification | Stabilising mutation |
|---|---|---|
| Protomer interface | 2139 | S2139L |
| | 3108 | T3108A |
| | 3141 | A3141G |
| | 3175 | T3175A |
| | 3178 | Q3178L |
| | 3180 | I3180T |
| | 3184 | F3184Y |
| | 3229 | T3229P |
| | 1030 | T1030S |
| | 1041 | T1041I |
| | 1067 | I1067L |
| | 1104 | 1104L deletion |
| | 1107 | V1107I |
| | 1160 | I1160V |
| | 1179 | S1179C |
| | 1199 | V1199M |
| | 1222 | S1222P |
| | 1223 | T1223S |
| | 1231 | A1231V |
| | 1232 | A1232V |
| | 1234 | L1234M |
| Pentamer interface | 2013 | V2013L |
| | 2014 | I2014M |
| | 2057 | D2057E, D2057A, D2057N |
| | 2246 | I2246L |
| | 2251 | T2251S |
| | 3073 | N3073H |
| | 3085 | L3085F |
| | 3141 | A3141G |
| | 1039 | K1039R |
| Hydrophobic Pocket | 1134 | F1134L |
| | 1159 | Y1159F |
| | 1183 | V1183L |
| | 1194 | I1194V |
| Internal network: 3-fold axis | 4055 | E4055A, E4055Q |
| | 4057 | I4057L, I4057V |
| | 2033 | V2033I |
| | 3161 | Q3161E |
| Internal network: 5-fold axis | 1021 | L1021P |
| VP1/2/3 interface | 2191 | I2191V |
| Canyon | 2140 | M2140T |
| Other | 2161 | T2161S |
| | 3094 | R3094K |
| | 1100 | R1100C |

A type 3 VLP of the invention may comprise one or more, two or more, three or more, four or more, five or more, six or more, seven or more, eight or more, nine or more, ten or more, or more modifications at one or more of the positions listed in Table 3 below, relative to the poliovirus particle from which the VLP is derived. The particular mutation at any one of these positions may be as given in Table 3 below.

A type 3 VLP of the invention may comprise any combination of modifications at any combination of the disclosed amino acid positions as set out in Table 3 below, provided the combination of modifications results in a VLP with the necessary properties (e.g. stability, antigenicity and/or immunogenicity) to make it suitable for use as a polio vaccine. In some embodiments, a VLP may comprise at most two modifications in any particular region, regardless of the total number of modifications in said VLP. A type 3 VLP of the invention typically comprises at least one modification in a protomer interface and at least one modification in a pentamer interface, optionally with at least one modification in a pocket domain. Preferably a type 3 VLP of the invention comprises at least one (preferably one or two) modifications in a protomer interface and/or at least one (preferably one or two) modifications in a pentamer interface, optionally with at least one (preferably one) modification in a pocket domain and/or at least one (preferably one) modification in a VP2/VP3 interface and/or at least one (preferably one, two or three) modifications in an internal network and/or at least one (preferably one) modification in a canyon domain. As a non-limiting example, a type 3 VLP of the invention may comprise nine modifications relative to the poliovirus particle from which it is derived: two modifications in a protomer interface (e.g. at 2215 and 3091), two modifications in a pentamer interface (e.g. at 2018 and 3085), one modification in a pocket domain (e.g. at 1132), one modification at a VP2/VP3 interface (e.g. at 2241), two modifications in an internal network (e.g. at 4067 and) and one modification in a canyon domain (e.g. at 1105). In a further example, a type 3 VLP of the invention may comprise these nine modifications and in addition a further (tenth) modification in the internal network (e.g. at 1054).

TABLE 3

The position of serotype 3 capsid stabilising modifications and particular stabilising mutations

| Region | Position of modification | Stabilising mutation |
|---|---|---|
| Protomer interface | 2215 | L2215M |
| | 3091 | F3091S |
| | 3178 | Q3178L |
| | 3190 | I3190V |
| | 1075 | I1075V |
| | 1181 | I1181L |
| | 1199 | L1199I |
| | 1155 | I1155M |
| Pentamer interface | 2016 | L2016I |
| | 2018 | L2018I |
| | 3085 | L3085F |
| | 3190 | I3190V |
| | 1034 | A1034V |
| Drug-binding pocket | 1132 | F1132L |
| | 1260 | M1260I |
| Internal network: 3-fold axis | 4055 | E4055Q |
| | 4067 | T4067A |
| | 2124 | M2124I |
| | 1054 | A1054V, A1054T |
| Internal network: around 5-fold axis | 3019 | H3019Y |
| | 1265 | V1265I |
| | 1075 | I1075V |
| external (3-fold) (VP2/VP3 interface) | 2241 | D2241E |
| external (protomer near interface) | 2269 | K2269R |
| canyon | 1105 | T1105M |

As described herein, a VLP of the invention preferably comprises at least three modifications relative to the poliovirus particle from which the VLP is derived, wherein there is at least one modification in each of (a) a protomer interface; and (b) a pentamer interface. As a non-limiting example a VLP of the invention may comprise (a) a pocket domain; (b) a protomer interface; and (c) a pentamer interface; wherein each of (a) to (c) comprises at least one modification relative to the poliovirus particle from which the VLP is derived. Said modifications may be any combination of modifications identified herein, particularly in any one of Tables 1 to 3. More preferably, a VLP of the invention comprises at least four, even more preferably at least five and even more preferably at least six modifications relative to the poliovirus particle from which it is derived; said modifications including at least one modification in a protomer interface and at least one modification in a pentamer interface, and optionally at least one modification in a pocket domain. Again, said modifications may be any combination of modifications identified herein, particularly in any one of Tables 1 to 3.

For example, the protomer interface may comprise a modification at one or more of amino acid residues 3108 (type 1 or 2), 3178 (type 1, 2 or 3), 1101 (type 1), 1168 (type 1), 1231 (type 1 or 2), 1232 (type 1 or 2), 1236 (type 1), 1247 (type 1), 1248 (type 1), 2139 (type 2), 3141 (type 2), 3175 (type 2), 3180 (type 2), 3184 (type 2), 3229 (type 2), 1030 (type 2), 1041 (type 2), 1067 (type 2), 1104 (type 2), 1107 (type 2), 1160 (type 2), 1179 (type 2), 1199 (type 2), 1222 (type 2), 1223 (type 2), 1234 (type 2), 2215 (type 3), 3091 (type 3), 3190 (type 3), 1075 (type 3), 1181 (type 3), 1199 (type 3) and/or 1155, or amino acid residues corresponding thereto. Preferably, the protomer interface may comprise a modification at one or more of amino acid residues 1248, i.e. residue 248 of VP1 (type 1), 2215, i.e. residue 215 of VP2 (type 3), 3178, i.e. residue 178 of VP3 (types 1 and 2), 1107, i.e. residue 107 of VP1 (type 2) and/or 3091, i.e. residue 91 of VP3 (type 3), or amino acid residues corresponding thereto.

For example, the pentamer interface may comprise a modification at one or more of amino acid residues 2014 (type 1 or 2), 2025 (type 1), 2057 (type 1), 2067 (type 1), 2251 (type 1 or 2), 2252 (type 1), 1040 (type 1), 1041 (type 1), 2013 (type 2), 2057 (type 2), 2246 (type 2), 3073 (type 2), 3085 (type 2 or 3), 3141 (type 2), 1039 (type 2), 2016 (type 3), 2018 (type 3), 3190 (type 3) and/or 1034 (type 3), or amino acid residues corresponding thereto. Preferably, the pentamer interface may comprise a modification at one or more of amino acid residues 1041, i.e. residue 41 of VP1 (type 2), 2018, i.e. residue 18 of VP2 (type 3), 2025, i.e. residue 25 of VP2 (type 1), 2057, i.e. residue 57 of VP2 (types 1 and 2), 3085, i.e. residue 85 of VP3 (types 2 and 3), or amino acid residues corresponding thereto.

The present invention encompasses VLPs comprising modifications at any of the above amino acid residues, provided that there is at least one modification, preferably at least one mutation (amino acid substitution) in each of the protomer interface and pentamer interface.

In embodiments wherein the pocket domain comprises one or modification, said one or more modification may comprise a modification at one or more of amino acid residues 1196 (type 1), 1134 (type 2), 1159 (type 2), 1183 (type 2), 1194 (type 2), 1132 (type 3) and/or 1260 (type 3), or amino acid residues corresponding thereto. Preferably in such embodiments, the pocket domain comprises a modification at one or more of amino acid residues 1132, i.e. residue 132 of VP1 (type 3), 1134, i.e. residue 134 of VP1 (type 2), 1159, i.e. residue 159 of VP1 (type 2), residue 1183, i.e. residue 183 of VP1 (type 2) and/or 1196, i.e. residue 196 of VP1 (type 1), or amino acid residues corresponding thereto.

In a preferred embodiment the VLP is derived from a type 1 poliovirus, wherein: (a) the protomer interface comprises a mutation at one or both of residues 3178 (i.e. residue 178 of VP3) and 1248 (i.e. residue 248 of VP1) or residues corresponding thereto; and/or (b) the pentamer interface comprises a mutation at one or both of residues 2025 (i.e. residue 25 of VP2) and 2057 (i.e. residue 57 of VP2) or residues corresponding thereto. In a particularly preferred embodiment, the protomer interface comprises one or both of the mutations Q3178L and H1248P; and/or the pentamer interface comprises one or both of the mutations T2025A and D2057E. In embodiments wherein the VLP is derived from a type 1 poliovirus and the pocket domain also comprises one or more modification, said modification preferably comprises a mutation at residue 1196 (i.e. residue 196 of VP1) or a residue corresponding thereto; more preferably the pocket domain comprises the mutation V1196L.

In another preferred embodiment, the VLP is derived from a type 2 poliovirus, wherein: (a) the protomer interface comprises a mutation at one or both of residues 3178 (i.e. residue 178 of VP3) and 1107 (i.e. residue 107 of VP1) or residues corresponding thereto; and/or (b) the pentamer interface comprises a mutation at one or more of residues 3085 (i.e. residue 85 of VP3), 1041 (i.e. residue 41 of VP1) and 2057 (i.e. residue 57 of VP2) or residues corresponding thereto. In a particularly preferred embodiment, the protomer interface comprises one or both of the mutations Q3178L and V110I; and/or the pentamer interface comprises one or more of the mutations L3085F, T1041I and D2057A. In embodiments wherein the VLP is derived from a type 2 poliovirus and the pocket domain also comprises one or more modification, said modification preferably comprises a mutation at one or more of residues 1134 (i.e. residue 134 of VP1), 1159 (i.e. residue 159 of VP1) and 1183 (i.e. residue 183 of VP1) or residues corresponding thereto; more preferably the pocket domain comprises one or more of the mutations F1134L, Y1159F and V1183L. In a particularly preferred embodiment, the protomer interface comprises a modification at residue 3178 (e.g. Q3178L), and/or the pentamer interface comprises modifications at both residues 1041 (e.g. T1041I) and 3085 (e.g. L3085F), and optionally the pocket domain also comprises modifications at both residues 1134 (e.g. F1134L) and 1159 (e.g. Y1159F). In another particularly preferred embodiment, the promoter interface comprises a modification at both residues 3178 (e.g. Q3178L) and 1107 (e.g. V1107I), and/or the pentamer interface comprises a modification at residue 2057 (e.g. D2057A), and optionally the pocket domain also comprises modifications at both residues 1134 (e.g. F1134L) and 1183 (e.g. V1183L).

In another preferred embodiment, the VLP is derived from a type 3 poliovirus, wherein: (a) the protomer interface comprises a mutation at one or both of residues 2215 (i.e. residue 215 of VP2) and 3091 (i.e. residue 91 of VP3) or residues corresponding thereto; and/or (c) the pentamer interface comprises a mutation at one or both of residues 2018 (i.e. residue 18 of VP2) and 3085 (i.e. residue 85 of VP3) or residues corresponding thereto. In a particularly preferred embodiment, the protomer interface comprises one or both of the mutations L2215M and F3091S; and/or the pentamer interface comprises one or both of the mutations L20181 and L3085F. In embodiments wherein the VLP is derived from a type 3 poliovirus and the pocket domain also comprises one or more modification, said modification preferably comprises a mutation at residue 1132 (i.e. residue 132 of VP1) or a residue corresponding thereto; more preferably the pocket domain comprises the mutation F1132L. In the case of a stabilising mutation at residue 3091 (i.e. residue 91 of VP3), the stabilising mutation may exist in the type 3 poliovirus from which the VLP is derived, or may be introduced to the VLP according to the methods of the present invention. For example, the type 3 polioviruses Leon and Saukett comprise a serine at residue 3091, whereas Sabin 3 poliovirus has a phenylalanine at this position. The 3091F makes the Sabin 3 poliovirus temperature sensitive, i.e. is destabilising in its effect, whereas 3091S is stabilising. Therefore, is a VLP of the invention is generated from a strain which comprises 3091F (e.g. Sabin 3), a stabilising mutation (e.g. F3091S) may be introduced. In the alternative, starting from Leon or Saukett, the stabilising residue 3091S is already present. Where reference is made herein to a stabilising mutation at residue 3091, this encompasses VLPs wherein either the stabilising residue is present in the original poliovirus strain, or wherein the mutation is introduced according to the present invention. The same also applies for other positions which may comprise stabilising amino acids in some poliovirus (type 1, 2 or 3) strains, but destabilising mutations in others. In each case, where reference is made herein to a stabilising mutation at a given residue, this encompasses VLPs wherein either the stabilising residue is present in the original poliovirus strain, or wherein the mutation is introduced according to the present invention. As a further non-limiting example, Saukett type 3 poliovirus comprises a stabilising valine residue at position 1054, whereas Leon and Sabin 3 type 3 poliovirus do not. In this example, where a type 3 VLP of the invention comprises a stabilising mutation at position 1054, this encompasses VLPs derived from Saukett, which would already encompass the stabilising 1054V, and also VLPs derived from Leon or Sabin 3, into which the stabilising mutation A1054V is introduced.

In addition to the particular amino acid residues described above, a VLP of the invention may comprise one or more additional modification within one or more of the protomer interface, the pentamer interface and/or the pocket domain.

Furthermore, as well as comprising at least one modification within each of the protomer interface and the pentamer interface, a VLP of the invention may comprise at least one further modification in one or more additional structural domain. Typically said one or more additional structural domain is selected from a pocket domain, a VP2/VP3 interface, an internal network and/or a canyon, as described herein, but may comprise a modification within an external fold, VP1/VP2 interface or other domain defined herein. When the VLP comprises one or more further modification in an internal network, said internal network may comprise interactions between polypeptide chains derived from different capsid proteins, near the three-fold axis, and/or a beta annulus (tube-like structure) below the five-fold axis, and said at least one further modification may be located at or in close proximity to said three-fold axis, five-fold axis and/or tube below the five-fold axis.

In aspects of the invention wherein the VLP is derived from a type 1 poliovirus, at said least one further modification in one or more additional structural domain may be selected from: (a) a mutation at residue 3119 (i.e. residue 119 of VP3) or a residue corresponding thereto in the VP2/VP3 interface; and/or (b) a mutation at residue 4018 (i.e. residue 18 of VP4) or a residue corresponding thereto in the internal network; and/or (c) a mutation at residue 1196 (i.e. residue 196 of VP1) or a residue corresponding thereto in the pocket domain. In a preferred embodiment, the VP2/VP3 interface comprises the mutation L3119M; and/or the internal network comprises the mutation R4018G; and/or the pocket domain comprises the mutation V1196L.

In aspects of the invention wherein the VLP is derived from a type 2 poliovirus, at said least one further modification in one or more additional structural domain may be a mutation at residue 4057 (i.e. residue 57 of VP4) or a residue corresponding thereto in the internal network. In a preferred embodiment, the internal network comprises the mutation I4057V.

In aspects of the invention wherein the VLP is derived from a type 3 poliovirus, at said least one further modification in one or more additional structural domain may be selected from: (a) a mutation at residue 2241 (i.e. residue 241 of VP2) or a residue corresponding thereto in the VP2/VP3 interface; (b) a mutation at one or more of residues 1054 (i.e. residue 54 of VP1), 4067 (i.e. residue 67 of VP4) and 3019 (i.e. residue 19 of VP3) or residues corresponding thereto in the internal network comprises; and/or (c) a mutation at residue 1105 (i.e. residue 105 of VP1) or a residue corresponding thereto in the canyon; and/or (d) a mutation at residue 1132 (i.e. residue 132 of VP1) or a residue corresponding thereto in the pocket domain. In a preferred embodiment, the VP2/VP3 interface comprises the mutation D2241E; the internal network comprises one or more of the mutations A1054V, T4067A and H3019Y; and/or the canyon comprises the mutation T1105M; and/or the pocket domain comprises the mutation F1132L.

Typically the above-described modifications in the VP2/VP3 interface, internal network, canyon and/or pocket domain are in addition to the modifications in the protomer interface and/or pentamer interface as described herein. In preferred embodiments, a VLP of the invention comprises at least one modification at the preferred amino acid residues within the protomer interface and/or pentamer interface, or combinations thereof as described herein and at least one further modification at one of the preferred amino acid residues within the VP2/VP3 interface, internal network, canyon and/or pocket domain as described herein. In particularly preferred embodiments, a VLP of the invention comprises at least one of the preferred amino acid mutations at the preferred amino acid residues within the protomer interface and/or pentamer interface, or combinations thereof as described herein and at least one further preferred amino acid mutation at one of the preferred amino acid residues within the VP2/VP3 interface, internal network, canyon and/or pocket domain as described herein. Any and all combinations of modifications, particularly amino acid mutations/substitutions at the preferred amino acid residues described herein within any of the identified domains of the VLP is encompassed by the present invention. As a non-limiting example, a VLP the invention may be derived from a type 1 poliovirus and comprise modifications at (i) residues 3178 and 1248 in the protomer interface, (ii) residues 2025 and 2057 in the pentamer interface, and also optionally (iii) residues 1196 in the pocket domain, (iv) residues 3119 in the VP2/VP3 interface, and (v) residues 4018 in the internal network, and in particular (i) the mutations Q3178L and H1248P in the protomer interface, (ii) the mutations T2025A and D2057E in the pentamer interface, and also optionally (iii) the mutation V1196L in the pocket domain, (iv) the mutation L3119M in the VP2/VP3 interface, and (v) the mutation R4018G in the internal network. In a preferred embodiment, a VLP of the invention may be derived from a type 1 poliovirus and comprise (i) Q3178L and H1248P in the protomer interface, (ii) the mutations T2025A and D2057E in the pentamer interface, (iii) the mutation L3119M in the VP2/VP3 interface, (iv) the mutation R4018G in the internal network, and optionally (v) the mutation V1196L in the pocket domain.

Other non-limiting examples of VLPs derived from a type 1 poliovirus according to the present invention may have the following mutations or combinations of mutations: (i) a mutation in the internal network (e.g. at residue 4018, preferably R4018G) and a mutation in the pentamer interface (e.g. at residue 2025, preferably T2025A or at residue 2057, preferably D2057E); (ii) a mutation in the internal network (e.g. at residue 4018, preferably R4018G) and two mutations in the pentamer interface (e.g. at residues 2025 and 2057, preferably T2025A and D2057E); (iii) a mutation in the internal network (e.g. at residue 3119, preferably L3119M) and three mutations in the protomer interface (e.g. at residue 3178, preferably Q3178L, at residue 1231, preferably A1231V and at residue 1248, preferably H1258P); (iv) a mutation in the internal network (e.g. at residue 4018, preferably R4018G), two mutations in the pentamer interface (e.g. at residues 2025 and 2057, preferably T2025A and D2057E) and two mutations in the protomer interface (e.g. at residue 3178, preferably Q3178L and at residue 1248, preferably H1258P); (v) a mutation in the internal network (e.g. at residue 4018, preferably R4018G), two mutations in the pentamer interface (e.g. at residues 2025 and 2057, preferably T2025A and D2057E), two mutations in the protomer interface (e.g. at residue 3178, preferably Q3178L and at residue 1248, preferably H1258P) and a mutation in a pocket domain (e.g. at residue 1196, preferably V1196L); (vi) a mutation in the internal network (e.g. at residue 4018, preferably R4018G), two mutations in the pentamer interface (e.g. at residues 2025 and 2057, preferably T2025A and D2057E), and three mutations in the protomer interface (e.g. at residue 3178, preferably Q3178L, at residue 1231, preferable A1231V and at residue 1248, preferably H1258P); (vii) a mutation in the internal network (e.g. at residue 4018, preferably R4018G), two mutations in the pentamer interface (e.g. at residues 2025 and 2057, preferably T2025A and D2057E), two mutations in the protomer interface (e.g. at residue 3178, preferably Q3178L and at residue 1248, preferably H1258P) and a mutation in an internal network (e.g. at residue 3119, preferably L3119M); (viii) two mutations in the internal network (e.g. at residue 4018, preferably R4018G and at residue 3119, preferable L3119M), a mutation in the pentamer interface (e.g. at residues 2025, preferably T2025A or at residue 2057, preferably D2057E), three mutations in the protomer interface (e.g. at residue 3178, preferably Q3178L, at residue 1231, preferably A1231V and at residue 1248, preferably H1258P); (ix) two mutations in the internal network (e.g. at residue 4018, preferably R4018G and at residue 3119, preferably L3119M), two mutations in the pentamer interface (e.g. at residues 2025 and 2057, preferably T2025A and D2057E), two mutations in the protomer interface (e.g. at residue 3178, preferably Q3178L and at residue 1248, preferably H1258P) and a mutation in a pocket domain (e.g. at residue 1196, preferably V1196L); (x) two mutations in the internal network (e.g. at residue 4018, preferably R4018G and at residue 3119, preferably L3119M), two mutations in the pentamer interface (e.g. at residues 2025 and 2057, preferably T2025A and D2057E), and three mutations in the protomer interface (e.g. at residue 3178, preferably Q3178L, at residue 1231, preferably A1231V, and at residue 1248, preferably H1258P); (xi) two mutations in the internal network (e.g. at residue 4018, preferably R4018G and at residue 3119, preferably L3119M), a mutation in the pentamer interface (e.g. at residue 2025, preferably T2025A or at residue 2057, preferably D2057E), three mutations in the protomer interface (e.g. at residue 3178, preferably Q3178L, at residue 1231, preferably A1231V and at residue 1248, preferably H1258P) and a mutation in a pocket domain (e.g. at residue 1196, preferably V1196L); and (xii) two mutations in the internal network (e.g. at residue 4018, preferably R4018G and at residue 3119, preferably L3119M), two mutations in the pentamer interface (e.g. at residues 2025 and 2057, preferably T2025A and D2057E), three mutations in the protomer interface (e.g. at residue 3178, preferably Q3178L, at residue 1231, preferably A1231V, and at residue 1248, preferably H1258P) and a mutation in a pocket domain (e.g. at residue 1196, preferably V1196L).

As another non-limiting example, a VLP of the invention may be derived from a type 2 poliovirus and comprise modifications at (i) residue 3178 in the protomer interface, and (ii) residues 3085 and 1041 in the pentamer interface, and optionally (iii) residues 1134 and 1159 in the pocket domain, and in particular (i) the mutation Q3178L in the protomer interface, and (ii) the mutations L3085F and T1041I in the pentamer interface, and optionally (iii) the mutations F1134L and Y1159F in the pocket domain. Alternatively, a VLP of the invention may be derived from a type 2 poliovirus and comprise modifications at (i) residues 3178 and 1107 in the protomer interface, and (ii) residue 2057 in the pentamer interface, and optionally (iii) residues 1134 and 1183 in the pocket domain and (iv) residue 4057 in the internal network, and in particular (i) the mutations Q3178L and V1107I in the protomer interface, and (ii) the mutation D2057A in the pentamer interface, and optionally (iii) the mutations F1134L and V1183L in the pocket domain and (iv) the mutation I4057V in the internal network.

Other non-limiting examples of VLPs derived from a type 2 poliovirus according to the present invention may have the following mutations or combinations of mutations: (i) two mutations in a pocket domain (e.g. at any two of residues 1134, preferably F1134L, 1159, preferably Y1159F, 1183, preferably V1183L and 1194 preferably I1194V, and preferably at residues 1134 and 1159 or residues 1134 and 1194); (ii) three mutations in a pocket domain (e.g. at any three of residues 1134, preferably F1134L, 1159, preferably Y1159F, 1183, preferably V1183L and 1194 preferably I1194V, and preferably at residues 1134, 1159 and 1194); (iii) two mutations in the pentamer interface (e.g. at residues 3085, preferably L3085F and at residue 1041, preferably T1041I) and a mutation in the protomer interface (e.g. at residue 3178, preferably Q3178L); (iv) a mutation in the pentamer interface (e.g. at residue 1041, preferably T1041), a mutation in the protomer interface (e.g. at residue 3178, preferably Q3178L) and a mutation in a pocket domain (e.g. at residue 1134, preferably F1134L); (v) two mutations in the pentamer interface (e.g. at residues 3085, preferably L3085F and at residue 1041, preferably T1041I), a mutation in the protomer interface (e.g. at residue 3178, preferably Q3178L) and a mutation in a pocket domain (e.g. at residue 1134, preferably F1134L); (vi) a mutations in the pentamer interface (e.g. at residue 1041, preferably T1041I), a mutation in the protomer interface (e.g. at residue 3178, preferably Q3178L) and two mutations in a pocket domain (e.g. at residue 1134, preferably F1134L and at residue 1159, preferably Y1159F); (vii) two mutations in the pentamer interface (e.g. at residues 3085, preferably L3085F and at residue 1041, preferably T1041I), a mutation in the protomer interface (e.g. at residue 3178, preferably Q3178L) and two mutations in a pocket domain (e.g. at residue 1134, preferably F1134L and at residue 1159, preferable Y1159F); (viii) a mutations in the pentamer interface (e.g. at residue 1041, preferably T1041I), a mutation in the protomer interface (e.g. at residue 3178, preferably Q3178L) and three mutations in a pocket domain (e.g. at residue 1134, preferably F1134L, at residue 1159, preferably Y1159F and at residue 1194, preferably I1194V); (ix) two mutations in the pentamer interface (e.g. at residues 3085, preferably L3085F and at residue 1041, preferably T1041I), a mutation in the protomer interface (e.g. at residue 3178, preferably Q3178L) and three mutations in a pocket domain (e.g. at residue 1134, preferably F1134L, at residue 1159, preferably Y1159F and at residue 1194, preferably I1194V); and (x) a mutation in the pentamer interface (e.g. at residues 2057, preferably D2057A, two mutations in the protomer interface (e.g. at residue 3178, preferably Q3178L and at residue 1107, preferably V1107I), two mutations in a pocket domain (e.g. at residue 1134, preferably F1134L and at residue 1183, preferably V1183L) and a mutation in an internal network (e.g. at residue 4057, preferably I4057V).

In a further non-limiting example, a VLP of the invention may be derived from a type 3 poliovirus and comprise modifications at (i) residues 2215 and 3091 in the protomer interface, (ii) residues 2018 and 3085 in the pentamer interface, and optionally (iii) residues 1132 in the pocket domain, (iv) residues 2241 in the VP2/VP3 interface, (v) residues 4067, 3019 and 1054 in the internal network, and (vi) residues 1105 in the canyon, and in particular (i) the mutations L2215M and F3091S in the protomer interface, (ii) the mutations L20181 and L3085F in the pentamer interface, and optionally (iii) the mutation F1132L in the pocket domain, (iv) the mutation D2241E in the VP2/VP3 interface, (v) the mutations T4067A, H3019Y and A1054V in the internal network, and (vi) the mutation T1105M in the canyon. In a preferred embodiment, a VLP of the invention may be derived from a type 3 poliovirus and comprise (i) the mutations L2215M and F3091S in the protomer interface, (ii) the mutations L20181 and L3085F in the pentamer interface, (iii) the mutation F1132L in the pocket domain, (iv) the mutation D2241E in the VP2/VP3 interface, (v) the mutations T4067A, H3019Y and optionally A1054V in the internal network, and (vi) the mutation T1105M in the canyon.

Another non-limiting example of a VLP derived from a type 3 poliovirus according to the present invention may have the following combinations of mutations: (i) two mutations in the pentamer interface (e.g. at residue 2018, preferably L20181 and at residue 3085, preferably L3085F), a mutation in the protomer interface (e.g. at residue 2215, preferably L2215M), two mutations in the internal network (e.g. at residue 4067, preferably T4067A and at residue 3019, preferably H3019Y), a mutation in the VP2/VP3 interface (e.g. at residue 2241, preferably D2241E), a mutation in a pocket domain (e.g. at residue 1132, preferably F1132L) and a mutation in a canyon domain (e.g. at residue 1105, preferably T1105M).

In addition to the particular amino acid residues described above, a VLP of the invention may comprise one or more additional modification within one or more of the VP2/VP3 interface, the internal network, the canyon and/or the pocket domain. Typically said one or more additional modification is identified using a method of the invention as described herein.

Polynucleotides of the Invention

The present invention also provides a polynucleotide that encodes the VLP of the invention. The term polynucleotide encompasses both DNA and RNA sequences, although typically the polynucleotide comprises a DNA sequence.

A polynucleotide of the invention thus typically encodes a capsid precursor (P1) for the modified capsid of the VLP of the invention, together with a suitable protease. Examples of suitable proteases include 3C and 3CD from poliovirus or another enterovirus. The level of protease expression is controlled to ensure adequate expression (to allow full processing of the P1 precursor into the mature VP0, VP1 and VP3 proteins), whilst minimising cell toxicity due to bystander cleavage of host cell proteins. Such control may be readily practised by conventional methods. A polynucleotide of the invention may be used for recombinant expression of a VLP of the invention, or as a DNA/RNA vaccine.

The invention further provides an expression vector comprising a polynucleotide of the invention. Typically in the expression vector the polynucleotide of the invention is operably linked to a suitable promoter. The polynucleotide may also be linked to a suitable terminator sequence. Suitable promoter and terminator sequences are well known in the art.

The choice of promoter depends in this case on the expression systems used for expression. In general, constitutive promoters are preferred, but inducible promoters may likewise be used. The construct produced in this manner includes at least one part of a vector, in particular regulatory elements. The vector is preferably capable of expressing the nucleic acid in a given host cell. Any appropriate host cell may be used, such as mammalian, insect, yeast, and/or plant host cells. In addition, cell-free protein synthesis may be used. Such expression systems and host cells are standard in the art.

Virus-free expression in mammalian cells would be the nearest system to the natural environment in which VLPs are processed and assembled during normal virus growth. One exemplary mammalian expression for poliovirus VLPs is the vaccinia virus expression system (Ankara strain—MVA). This system allows high levels of recombinant protein expression, with the advantage of maintaining authentic post-translational modification of the expressed products in the most authentic environment; the mammalian cell.

The VLPs of the invention, and polynucleotides encoding said VLPs may be expressed in insect cells using baculovirus vectors. Human vaccine production in insect cells via a baculovirus vector has the advantage of precedence since a commercially available human papilloma vaccine now in use is produced in this way. Non-limiting examples of suitable insect cell lines include Sf9, T. Ni and Ao38.

The VLPs of the invention, and polynucleotides encoding said VLPs may be expressed in yeast. The potential advantages of high yields and low cost of production make yeast expression systems attractive. Yeast expression technology using either *Saccharomyces* or *Pichia* is possible using standard techniques.

The VLPs of the invention, and polynucleotides encoding said VLPs may be expressed in plant cells. Plants have a number of potential advantages: they are robust, inexpensive to grow and any product derived from them carries a low risk of contamination with endotoxins or mammalian pathogens. Again, methods and techniques are known in the art.

Alternatively, a cell-free protein synthesis system may be used. Such systems have distinct advantages over traditional in vivo methods for protein production. The absence of the requirement to maintain cell viability allows for the optimization of the protein synthetic capacity of the cell-free extract to produce proteins. In addition, the lack of a cellular membrane allows for the direct addition of non-natural factors which can be used to manipulate transcription, translation and folding, and provide precise modulation of the protein expression process. Exemplary cell-free systems derived from *E. coli* are known in the art. Co-expression of mammalian N-myristyl transferase within bacterial cells may be required to achieve the correct modification of the viral precursor protein to facilitate proper folding and capsid assembly.

The nucleic acid molecules of the invention may be made using any suitable process known in the art. Thus, the nucleic acid molecules may be made using chemical synthesis techniques. Alternatively, the nucleic acid molecules of the invention may be made using molecular biology techniques.

The expression vector of the present invention is preferably designed in silico, and then synthesised by conventional polynucleotide synthesis techniques.

The polynucleotide sequence information is optionally modified for codon-biasing according to the ultimate host cell (e.g. a plant cell, insect cell, yeast cell, mammalian cell, *E. coli*) expression system that is to be employed.

The present invention also provides polypeptides encoded by polynucleotide sequences as described above.

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

Method of Identifying Modifications which Modulate Poliovirus Capsid Stability

The present inventors have devised an innovative method for identifying stabilising modifications, particularly stabilising mutations within the poliovirus capsid. In particular, the inventors approach begins with the selection of a poliovirus strain which has an assembly defect. One non-limiting example of such a starting strain is Sabin 3, which comprises a mutation at residue 91 of VP3 (i.e. a mutation at 3091). In the wild-type Leon strain this position is a serine, whereas in the Sabin 3 strain the residue is a phenylalanine. This mutation makes Sabin 3 assembly temperature sensitive (ts) by inhibiting the assembly of capsid assembly intermediates, the higher the temperature the greater the inhibition. The present inventors surprisingly found that mutations which overcome this temperature sensitivity, when introduced into wild-type capsid proteins, stabilise VLPs.

Thus, the present invention further provides a method of identifying one or more modifications within a poliovirus capsid which modulate (typically increase) the stability of said poliovirus capsid. Said method comprises the steps of: (a) introducing a destabilising mutation (such as S3091F) into the capsid of a poliovirus strain; (b) growing said poliovirus strain at semi-permissive temperatures; and (c) screening the resulting (non-temperature-sensitive) polioviruses to identify one or more modification the reverse the effect of the destabilising mutation. In some embodiments, the poliovirus strain used in said method is a poliovirus strain which already has an assembly defect. In such embodiments, step (a) of the method is not required and the invention provides a method in which this step is omitted. This strain may be an existing (vaccine or naturally occurring) strain. A non-limiting example of a suitable starting poliovirus strain is Sabin 3. Otherwise the assembly defect may be introduced into a strain desired as the starting point for the method (step (a)). A non-limiting example of a suitable starting poliovirus strain of this type is Mahoney and a suitable assembly defect would be that resulting from a serine to phenylalanine substitution at residue 91 of VP3 (S3091F). Thus, the method developed by the present inventors is unique: it relies of the introduction of a destabilising mutation to a poliovirus test strain (or use of an existing strain with such a mutation) and growing said test strain at semi-permissive temperatures to generate viruses with re-stabilising mutations. Typically said method involves deep sequencing (i.e. without purification) of the resulting stabilised poliovirus strains to identify the stabilising mutations.

As described herein, these stabilising mutations can then be introduced into the P1 region of the poliovirus genome in different combinations and recombinant expression would then allow the production of stable VLPs for use as vaccines without the need for live virus. Accordingly, the method of the invention may further comprise the step of introducing one or modification identified in step (c) into a wild-type poliovirus and verifying that said one or modification increases the stability of the poliovirus capsid.

The method may involve the introduction of any suitable destabilising mutation to a poliovirus test strain, or the use of an existing test strain with any suitable destabilising mutations. Suitable destabilising mutations may be selected, for example, by growing poliovirus under conditions of low/reduced temperature (typically below 33° C.), growing on cells which express a mutant poliovirus receptor (PVR) or pseudoreversion of stabilised mutants. Typically, the phenotypic effects of a suitable destabilising mutation include increased temperature-sensitivity for growth, and/or reduced "cold" sensitivity (i.e. at temperatures below 33° C.) and/or enlarged range of receptor usage, and increased viability. In some embodiments, a combination of destabilising mutations may be used.

Non-limiting examples of destabilising mutations suitable for use in the methods of the present invention include:

TABLE 4

Exemplary destabilising mutations

| Region | Position of modification | Destabilising mutation |
|---|---|---|
| Protomer interface | 3026 | P3026S |
| | 3091 | S3091F |
| | 3228 | T3228A |
| | 3232 | S3232L |
| | 1114§ | V1114A§ |
| | 1171 | Y1171H |
| | 1172§ | T1172A§ |
| | 1248# | N1248S# |
| Pentamer interface | 4065 | A4065T, A4065S |
| | 2068 | T2068N |
| | 3130 | I3130V |
| | 1041* | I1041T* |
| Internal network: 3-fold axis | 4057 | L4057I |
| | 4063 | K4063R |
| | 2029 | A2029T |
| | 2030 | N2030S |
| | 2033 | V2033L |
| | 2124 | V2124M |
| | 2208 | V2208I |
| | 1042§ | L1042I§ |
| | 1049§ | A1049T§ |
| | 1051§ | N1051S§ |
| | 1052§ | P1052S, P1052L§ |
| | 1054§ | V1054A§ |
| Internal network: 5-fold axis | 4006 | S4006T |
| | 4048 | N4038S |

TABLE 4-continued

Exemplary destabilising mutations

| Region | Position of modification | Destabilising mutation |
|---|---|---|
| VP2/VP3 interface | 2200 | R2200K |
| | 2157 | Y2157F |
| VP2/VP1 interface (same protomer) | 2184 | V2184A |
| | 2192 | Y2192C |
| | 2191 | V2191I |
| Junction of VP1/2/3 | 2186 | L2186M |
| Canyon | 1105§ | M1105T, M1105V§ |
| Other | 2136 | S2136G |
| | 1122§ | F1122L§ |

*destabilising mutation identified in type 2 poliovirus. The corresponding position in type 3 is 1039.
§destabilising mutations identified in type 3 poliovirus. For the corresponding position in type 1/2 add two to the positions listed in Table 4 above.
#destabilising mutation identified in type 3 poliovirus. For the corresponding position in type 1/2 add one to the position listed in Table 4 above.

The method may be conducted at any temperature which is semi-permissive for growth of the chosen poliovirus strain. In this context, a "semi-permissive" temperature may be defined as any temperature which allows all replication steps except capsid assembly. For example, a semi-permissive temperature may be in the range of from about 38° C. to about 40° C.

Typically said method is used to identify modifications which increase the stability of the poliovirus capsid if the growth of the poliovirus strain at semi-permissive temperatures is reduced without the modification. Other effects of the stabilising modifications may include increased "cold" sensitivity (i.e. increased sensitivity when grown at temperatures below 33° C.). Stabilising mutations may be screened for using plaque assays or by other methods such as deep sequencing/next generation sequencing.

The present invention also encompasses other methods of identifying candidate modifications which modulate the stability of a poliovirus capsid. For example, stabilising mutants identified by the above method can be introduced into wild-type strains in different combinations. When said combinations of mutants stabilises the viral capsid beyond what is optimal for assembly or uncoating, viral growth at temperatures that are fully-permissive for all steps of wild-type replication is typically reduced. When these viruses are grown at fully permissive temperatures, new faster-growing poliovirus variants arise. These faster-growing variants typically have either lost one or more of the originally acquired stabilising mutations, and/or have acquired new destabilising mutations at other residues within the capsid proteins. The positions of these destabilising mutations can be targeted in other viruses to produce stabilising mutations using the techniques disclosed herein.

Other approaches to the identification of candidate capsid stabilising mutations including prediction of stabilising interactions from the atomic structure and selecting for thermostable virus mutants by limited exposure to high temperatures and may be used according to the present invention.

Methods of Production

The invention further provides a method of producing a VLP of the invention, said method involving: (a) introducing an infectious RNA transcript encoding the VLP into a host mammalian cell; or (b) recombinantly producing poliovirus capsid derived polypeptides comprising one or more modification (preferably the one or more mutation) identified by the identification method described herein and assembling said polypeptides to form a VLP.

Typically said method (b) comprises the step of expressing a polynucleotide of the invention, along with an appropriate protease, in a cell, wherein the capsid derived polypeptides will be expressed and, after cleavage, autoassemble into VLPs and recovering the expressed VLPs. The method typically further comprises a step of introducing the polynucleotide of the invention into the cell. For example, the polynucleotide of the invention may be introduced into the cell in the form of an expression vector as described herein.

For example, said method for producing a VLP of the invention may the comprise expressing a polynucleotide (as described above) in a suitable host cell, lysing the host cell to provide a host cell homogenate containing the VLP, and isolating the VLP.

The polynucleotide provided/introduced to the cell may be DNA, RNA or mixtures thereof. The polynucleotide may furthermore be modified with regard to its nuclease resistance, such as e.g. by inserting phosphorthioate bonds. The nucleic acid may be produced from a starting nucleic acid, the latter being accessible e.g. by cloning from genomic or cDNA-databases. Moreover, the nucleic acid may be produced directly by solid phase synthesis. Suitable methods are known to the person skilled in the art. If one assumes a starting nucleic acid, a specific modification, e.g. by locality-specific mutagenesis, may be brought about, resulting in at least one addition, insertion, deletion and/or substitution on the amino acid level. The nucleic acid is then linked operatively to a suitable promoter as described herein.

Typically a VLP of the invention is generated by recombinant means. In particular, stabilising mutations can be identified by the methods described herein. The DNA from a stabilised poliovirus generated by said methods can be cloned and transcribed to form RNA. This RNA can be introduced into a suitable expression cell using standard cell culture techniques and used to generate empty, non-infection VLPs in a single-round production method.

The VLP of the invention from the cell is typically purified and/or concentrated after recovery from the cell. Any suitable method(s) may be used for the recovery, purification and/or concentration of the polypeptide of the invention. Standard techniques for recovery, purification and/or concentration are known in the art, for example chromatography methods and/or electrophoresis.

Cells

The VLP of the present invention may be produced by a suitable cell (also known as host cells), such as e.g. *Escherichia coli, Saccharomyces cerevisiae, Pichia pastoris* or *Bacillus megaterium*, which multiplies a recombinant expression vector, the vector coding for a VLP of the invention.

Accordingly, the invention further provides cells, which produce a VLP of the invention. Typically the cells of the invention contain a polynucleotide or expression vector of the invention and are suitable for expressing the polynucleotide or vector. Numerous prokaryotic and eukaryotic expression systems are known in the state of the art, the cells being selected, for example, from prokaryotic cells such as *E. coli* or *B. megaterium*, from eukaryotic cells such as *S. cerevisiae* and *P. pastoris*. Higher eukaryotic cells, such as insect cells, plant cells or mammal cells, may be used as well.

Compositions and Therapeutic/Cosmetic Indications

The invention also provides a pharmaceutical composition comprising a VLP of the invention. The composition, which is typically a pharmaceutical composition, may optionally comprise a pharmaceutically acceptable excipient, diluent, carrier, propellant, salt and/or additive. Typically the composition of the invention is suitable for vaccinating against poliovirus. The composition is particularly suitable for subcutaneous, intramuscular, implant and/or topical administration. Intramuscular administration is preferred. Compositions suitable for injection may be in the form of solutions, suspensions or emulsions, or dry powders which are dissolved or suspended in a suitable vehicle prior to use.

The dosage ranges for administration of the VLP of the present invention are those to produce the desired therapeutic effect. It will be appreciated that the dosage range required depends on the precise nature of the VLP or composition, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable dosages may be in the same range as those of current IPV in terms of D-antigen units per human dose (40, 8 and 32 for types 1, 2 and 3) or may be lower if VLPs prove more immunogenic than IPV in humans, as they appear to be in animals.

Fluid dosage forms are typically prepared utilising the VLP and a pyrogen-free sterile vehicle. The VLP, depending on the vehicle and concentration used, can be either dissolved or suspended in the vehicle. In preparing solutions the VLP can be dissolved in the vehicle, the solution being made isotonic if necessary by addition of sodium chloride and sterilised by filtration through a sterile filter using aseptic techniques before filling into suitable sterile vials or ampoules and sealing. Advantageously additives such as buffering, solubilising, stabilising, preservative or bactericidal, suspending or emulsifying agents and or local anaesthetic agents may be dissolved in the vehicle.

Dry powders, which are dissolved or suspended in a suitable vehicle prior to use, may be prepared by filling pre-sterilised ingredients into a sterile container using aseptic technique in a sterile area. Alternatively the ingredients may be dissolved into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

A suspending agent, for example, polyvinylpyrrolidone may be included in the composition(s) to facilitate uniform distribution of the components.

Administration in accordance with the present invention may take advantage of a variety of delivery technologies including microparticle encapsulation, viral delivery systems or high-pressure aerosol impingement.

The invention further provides a VLP, composition or vaccine as described herein for use in a method of vaccinating against poliovirus. The invention further provides the use of a VLP and/or composition as described herein in the manufacture of a medicament for use in a method of vaccinating against poliovirus The invention further provides a method of vaccinating a subject against poliovirus, the method comprising administering to a subject in need thereof an effective amount of a VLP, composition or vaccine.

Vaccines

The poliovirus-like particles (VLPs) of the invention may be used on a small scale for example as an antigen in serology assays (e.g. as part of seroprevalence studies or other surveillance activities) or on a massive scale in vaccine production. As the VLPs of the invention are non-infectious (lacking the poliovirus genome), and production via recombinant expression would not require live virus, containment both prior to eradication of poliovirus and, post-eradication (at category BSL3-polio as required by current WHO guidance for viable strains infectious for humans) would not be needed.

The VLPs of the invention may be produced by any appropriate method (as described herein), typically using recombinant techniques. As the VLPs of the invention are non-infectious, inactivation is not required prior to use as a vaccine.

A VLP of the invention may be combined with a pharmaceutically acceptable carrier or diluent. Any carrier or diluent conventionally used in inactivated virus preparations or other poliovirus vaccines, for example IPV preparations, may be employed. The VLP preparation may comprise VLP comprising type 1, type 2 and/or type 3 capsid proteins.

The VLP of the invention can therefore be used to vaccinate against poliomyelitis in a human patient. Accordingly, the invention provides a method of vaccinating a subject against poliovirus, the method comprising administering to a subject in need thereof an effective amount of a VLP of the invention. An effective amount is an amount sufficient to elicit a protective immune response against poliovirus. For this purpose, they may be administered by any suitable route, such as parenterally. Parenteral administration may be by subcutaneous, intradermal or intramuscular injection. The VLP of the invention may be administered with an adjuvant.

A dose corresponding to the amount administered for a conventional IPV, such as 8 to 40 units of D antigen, may be administered.

The dose of the VLP of the invention may be adjusted to achieve the required degree of immunogenicity. For example, when a capsid protein is derived from Sabin 2 or Sabin 3 a higher dose may be used than when the capsid protein is derived from Sabin 1, MEF, Mahoney or Saukett. For example, a dose of from about 16 to about 80 units of D antigen, such as about 30 units of D antigen (for example, 32 units of D antigen) or about 60 units of D antigen (for example, 64 units of D antigen) may be used. Lower doses may be used if the vaccine is administered with an appropriate adjuvant.

The present invention provides a vaccine comprising one or more VLPs of the invention and a pharmaceutically acceptable carrier or diluent. The vaccine may further comprise an adjuvant. The vaccine may comprise one or more different intertypic recombinant VLPs of the invention. For example, the vaccine may comprise a mixture of VLPs comprising structural proteins from type 1 and type 2, type 1 and type 3, type 2 and type 3 or type 1, type 2 and type 3 poliovirus strains. Typically the type 1 capsid proteins will be from Sabin 1 or Mahoney, preferably Mahoney, the type 2 capsid protein, from Sabin 2 or MEF, preferably MEF and the type 3 capsid proteins from Sabin 3 or Saukett, preferably Saukett.

In view of the different relative immunogenicities of the type 1, type 2 and type 3 polioviruses of the invention, the vaccine may comprise different amounts of VLPs containing type 1, type 2 and/or type 3 capsid proteins. For example, a type 1:type 2:type 3 ratio of x:y:z may be used where $x<y<z$. In one specific example, the ratio may be 40:8:32 units of D antigen.

The VLP of the invention may be administered as a stand-alone poliovaccine or in a combination vaccine containing other components, such as DTP (diphtheria, pertussis, tetanus), Hib (*Haemophilus* influenza type B) or Hepatitis B.

The present invention also provides: the use of a VLP according to the invention in the manufacture of a medicament for use in a method of vaccinating against poliovirus; and a VLP according to the invention for use in a method of vaccinating against poliovirus.

The present inventors are the first to appreciate that a stabilised VLP has the necessary stability and immunogenicity for utility in a poliovirus vaccine, as demonstrated in the Examples herein. Accordingly, the present invention provides a method of generating a poliovirus vaccine comprising providing a stabilised VLP. Typically said method comprises the step of identifying one or more capsid stabilising modifications, introducing said one or more stabilising modifications into a VLP and producing VLPs with the one or more stabilising modifications. The method of identifying said one or more stabilising modification and/or the method of producing said VLPs may be as described herein. The one or more capsid stabilising modification may be any modification/mutation as described herein, or any combination thereof.

The present invention provides a vector that expresses a VLP of the invention. Typically the vector is present in the form of a vaccine formulation.

The vector may be a viral vector. Such a viral vector may be an adenovirus (of a human serotype such as AdHu5, a simian serotype such as ChAd63, ChAdOX1 or ChAdOX2, or another form) or poxvirus vector (such as a modified vaccinia Ankara (MVA)). ChAdOX1 and ChAdOX2 are disclosed in WO2012/172277. ChAdOX2 is a BAC-derived and E4 modified AdC68-based viral vector.

Viral vectors are usually non-replicating or replication impaired vectors, which means that the viral vector cannot replicate to any significant extent in normal cells (e.g. normal human cells), as measured by conventional means—e.g. via measuring DNA synthesis and/or viral titre. Non-replicating or replication impaired vectors may have become so naturally (i.e. they have been isolated as such from nature) or artificially (e.g. by breeding in vitro or by genetic manipulation). There will generally be at least one cell-type in which the replication-impaired viral vector can be grown—for example, modified vaccinia Ankara (MVA) can be grown in CEF cells. In one embodiment, the vector is selected from a human or simian adenovirus or a poxvirus vector.

Typically, the viral vector is incapable of causing a significant infection in an animal subject, typically in a mammalian subject such as a human or other primate.

The invention further provides a nucleic acid vaccine which encodes a VLP of the invention. Such a vaccine may comprise DNA or RNA encoding a VLP of the invention.

For example a DNA vector or vaccine that expresses a VLP of the invention may be a plasmid-based DNA vaccine. In one embodiment the DNA vector is capable of expression in a mammalian cell expression system, such as an immunised cell.

The vector may be a RNA vector, such as a self-amplifying RNA vaccine (Geall, A. J. et al., Proc Natl Acad Sci USA 2012; 109(36) pp. 14604-9; incorporated herein by reference).

A nucleic acid vaccine of the invention typically comprises a nucleic acid (DNA or RNA) encoding a P1 capsid precursor polynucleotide for a VLP, together with a viral protease which is capable of cleaving said P1 capsid precursor into VP1, VP3 and VP3 capsid proteins for VLP assembly. Examples of suitable viral proteases include 3C and 3CD. The nucleic acid in said nucleic acid vaccine is typically operably linked to a suitable promoter. Examples of suitable promoters are readily available in the art.

Key to SEQ ID NOs

Human poliovirus type 1 Mahoney (complete genome) GenBank Accession No: V01149 (version V01149.1, deposited 10 Feb. 2003)

Human poliovirus type 2 strain MEF-1 (polyprotein gene, complete cds) GenBank Accession No: AY238473 (version AY238473.1, deposited 23 Sep. 2004)

Human poliovirus type 3 Saukett (H capsid protein (VP4, VP2, VP3, and VP1) RNA, 5' end) GenBank Accession No: L23848 (version L23848.1, deposited 11 Jul. 1994)

```
Mahoney VP1
                                                          SEQ ID NO: 1
GLGQMLESMIDNTVRETVGAATSRDALPNTEASGPTHSKEIPALTAVETGATNPLVPSDTVQTRHVVQ

HRSRSESSIESFFARGACVTIMTVDNPASTTNKDKLFAVWKITYKDTVQLRRKLEFFTYSRFDMELTF

VVTANFTETNNGHALNQVYQIMYVPPGAPVPEKWDDYTWQTSSNPSIFYTYGTAPARISVPYVGISNA

YSHFYDGFSKVPLKDQSAALGDSLYGAASLNDFGILAVRVVNDHNPTKVTSKIRVYLKPKHIRVWCPR

PPRQLAYYGPGVDYKDGTLTPLSTKDLTTY

Mahoney VP2
                                                          SEQ ID NO: 2
SPNIEACGYSDRVLQLTLGNSTITTQEAANSVVAYGRWPEYLRDSEANPVDQPTEPDVAACRFYTLDT

VSWTKESRGWWWKLPDALRDMGLFGQNMYYHYLGRSGYTVHVQCNASKFHQGALGVFAVPEMCLAGDS

NTTTMHTSYQNANPGEKGGTFTGTFTPDNNQTSPARSSARWITSLEMARCWGMPLCSAQIINLRTNNC

ATLVLPYVNSLSLDSMVKHNNWGIAILPLAPLNFVSESSPEIPITLTIAPMCCEFNGLRNITLPRLQ

Mahoney VP3
                                                          SEQ ID NO: 3
GLPVMNTPGSNQYLTADNFQSPCALPEFDVTPPIDIPGEVKNMMLAEIDTMIPFDLSATKKNTMEMYR

VRLSDKPHTAASILCLSLSPASDPRLSHTMLGEILNYYTHWAGSLKFTFLFCGSMMATGKLLVSYAPP

GADPPKKRKEAMLGTHVIWDIGLQSSCTMVVPWISNSTYRQTIDDSFTEGGYISVFYQTRIVVPLSTP

REMDILGFVSACNDFSVRLLRDTTHIEQKALAQ

Mahoney VP4
                                                          SEQ ID NO: 4
GAQVSSQKVGAHENSNRAYGGSTINYTTINYYRDSASNAASKQDFSQDPSKFTEPIKDVLIKTAPMLN

Mahoney VP0
                                                          SEQ ID NO: 5
GAQVSSQKVGAHENSNRAYGGSTINYTTINYYRDSASNAASKQDFSQDPSKFTEPIKDVLIKTAPMLN

SPNIEACGYSDRVLQLTLGNSTITTQEAANSVVAYGRWPEYLRDSEANPVDQPTEPDVAACRFYTLDT

VSWTKESRGWWWKLPDALRDMGLFGQNMYYHYLGRSGYTVHVQCNASKFHQGALGVFAVPEMCLAGDS

NTTTMHTSYQNANPGEKGGTFTGTFTPDNNQTSPARSSARWITSLEMARCWGMPLCSAQIINLRTNNC

ATLVLPYVNSLSLDSMVKHNNWGIAILPLAPLNFVSESSPEIPITLTIAPMCCEFNGLRNITLPRLQ

MEF VP1
                                                          SEQ ID NO: 6
GLGDLIEGVVEGVTRNALTPLTPANNLPDTQSSGPAHSKETPALTAVETGATNPLVPSDTVQTRHVIQ

KRTRSESTVESFFARGACVAIIEVDNDAPTKRASKLFSVWKITYKDTVQLRRKLEFFTYSRFDMEFTF

VVTSNYTDANNGHALNQVYQIMYIPPGAPIPGKWNDYTWQTSSNPSVFYTYGAPPARISVPYVGIANA

YSHFYDGFAKVPLAGQASTEGDSLYGAASLNDFGSLAVRVVNDHNPTKLTSKIRVYMKPKHVRVWCPR

PPRAVPYYGPGVDYKDGLAPLPEKGLTTY

MEF VP2
                                                          SEQ ID NO: 7
SPNIEACGYSDRVMQLTLGNSTITTQEAANSVVAYGRWPEYIKDSEANPVDQPTEPDVAACRFYTLDT

VTWRKESRGWWWKLPDALKDMGLFGQNMFYHYLGRAGYTVHVQCNASKFHQGALGVFAVPEMCLAGDS
```

-continued

TTHMFTKYENANPGEKGGEFKGSFTLDTNATNPARNFCPVDYLFGSGVLAGNAFVYPHQIINLRTNNC

ATLVLPYVNSLSIDSMTKHNNWGIAILPLAPLDFATESSTEIPITLTIAPMCCEFNGLRNITVPRTQ

MEF VP3

SEQ ID NO: 8

GLPVLNTPGSNQYLTADNYQSPCAIPEFDVTPPIDIPGEVRNMMELAEIDTMIPLNLTNQRKNTMDMY

RVELNDAAHSDTPILCLSLSPASDPRLAHTMLGEILNYYTHWAGSLKFTFLFCGSMMATGKLLVSYAP

PGAEAPKSRKEAMLGTHVIWDIGLQSSCTMVVPWISNTTYRQTINDSFTEGGYISMFYQTRVVVPLST

PRKMDILGFVSACNDFSVRLLRDTTHISQEAMPQ

MEF VP4

SEQ ID NO: 9

MGAQVSSQKVGAHENSNRAYGGSTINYTTINYYRDSASNAASKQDFAQDPSKFTEPIKDVLIKTAPTL

N

MEF VP0

SEQ ID NO: 10

SPNIEACGYSDRVMQLTLGNSTITTQEAANSVVAYGRWPEYIKDSEANPVDQPTEPDVAACRFYTLDT

VTWRKESRGWWWKLPDALKDMGLFGQNMFYHYLGRAGYTVHVQCNASKFHQGALGVFAVPEMCLAGDS

TTHMFTKYENANPGEKGGEEKGSFTLDTNATNPARNFCPVDYLFGSGVLAGNAFVYPHQIINLRTNNC

ATLVLPYVNSLSIDSMTKHNNWGIAILPLAPLDFATESSTEIPITLTIAPMCCEFNGLRNITVPRTQ

Saukett VP1

SEQ ID NO: 11

GIEDLITEVAQGALTLSLPKQQDSLPDTKASGPAHSKEVPALTAVETGATNPLVPSDTVQTRHVIQRR

SRSESTIESFFARGACVAIIEVDNEEPTTRAQKLFATWRITYKDTVQLRRKLEFFTYSRFDMEFTFVV

TANFTNTNNGHALNQVYQIMYIPPGAPTPKSWDDYTWQTSSNPSIFYTYGAAPARISVPYVGLANAYS

HFYDGFAKVPLKTDANDQIGDSLYSAMTVDDFGVLAIRVVNDHNPTKVTSKVRIYMKPKHVRVWCPRP

PRAVPYYGPGVDYKDNLNPLSEKGLTTY

Saukett VP2

SEQ ID NO: 12

SPNVEACGYSDRVLQLTLGNSTITTQEAANSVVAYGRWPEFIRDDEANPVDQPTEPDVATCRFYTLDT

VMWGKESKGWWWKLPDALRDMGLFGQNMYYHYLGRSGYTVHVQCNASKFHQGALGVFAIPEYCLAGDS

DKQRYTSYANANPGEKGGKFYSQFNRDTAVTSPKREFCPVDYLLGCGVLLGNAFVYPHQIINLRTNNS

ATIVLPYVNALAIDSMVKHNNWGIAILPLSPLDFAQDSSVEIPITVTIAPMCSEFNGLRNVTAPKFQ

Saukett VP3

SEQ ID NO: 13

GLPVLNTPGSNQYLTSDNHQSPCAIPEFDVTPPIDIPGEVKNMMELAEIDTMIPLNLENTKRNTMDMY

RVTLSDSADLSQPILCLSLSPASDPRLSHTMLGEVLNYYTHWAGSLKFTFLFCGSMMATGKILVAYAP

PGAQPPTSRKEAMLGTHVIWDLGLQSSCTMVVPWISNVTYRQTTQDSFTEGGYISMFYQTRIVVPLST

PKSMSMLGFVSACNDFSVRLLRDTTHISQSALPQ

Saukett VP4

SEQ ID NO: 14

MGAQVSSQKVGAHENSNRAYGGSTINYTTINYYKDSASNAASKQDYSQDPSKFTEPLKDVLIKTAPTL

N

Saukett VP0

SEQ ID NO: 15

MGAQVSSQKVGAHENSNRAYGGSTINYTTINYYKDSASNAASKQDYSQDPSKFTEPLKDVLIKTAPTL

NSPNVEACGYSDRVLQLTLGNSTITTQEAANSVVAYGRWPEFIRDDEANPVDQPTEPDVATCRFYTLD

TVMWGKESKGWWWKLPDALRDMGLFGQNMYYHYLGRSGYTVHVQCNASKFHQGALGVFAIPEYCLAGD

SDKQRYTSYANANPGEKGGKFYSQFNRDTAVTSPKREFCPVDYLLGCGVLLGNAFVYPHQIINLRTNN

SATIVLPYVNALAIDSMVKHNNWGIAILPLSPLDFAQDSSVEIPITVTIAPMCSEFNGLRNVTAPKFQ

-continued

Mahoney P1

SEQ ID NO: 16

MGAQVSSQKVGAHENSNRAYGGSTINYTTINYYRDSASNAASKQDFSQDPSKFTEPIKDVLIKTAPML

NSPNIEACGYSDRVLQLTLGNSTITTQEAANSVVAYGRWPEYLRDSEANPVDQPTEPDVAACRFYTLD

TVSWTKESRGWWWKLPDALRDMGLFGQNMYYHYLGRSGYTVHVQCNASKFHQGALGVFAVPEMCLAGD

SNTTTMHTSYQNANPGEKGGTFTGTFTPDNNQTSPARRFCPVDYLLGNGTLLGNAFVFPHQIINLRTN

NCATLVLPYVNSLSIDSMVKHNNWGIAILPLAPLNFASESSPEIPITLTIAPMCCEFNGLRNITLPRL

QGLPVMNTPGSNQYLTADNFQSPCALPEFDVTPPIDIPGEVKNMMELAEIDTMIPFDLSATKKNTMEM

YRVRLSDKPHTDDPILCLSLSPASDPRLSHTMLGEILNYYTHWAGSLKFTFLFCGSMMATGKLLVSYA

PPGADPPKKRKEAMLGTHVIWDIGLQSSCTMVVPWISNTTYRQTIDDSFTEGGYISVFYQTRIVVPLS

TPREMDILGFVSACNDFSVRLLRDTTHIEQKALAQGLGQMLESMIDNTVRETVGAATSRDALPNTEAS

GPTHSKEIPALTAVETGATNPLVPSDTVQTRHVVQHRSRSESSIESFFARGACVTIMTVDNPASTTNK

DKLFAVWKITYKDTVQLRRKLEFFTYSRFDMELTFVVTANFTETNNGHALNQVYQIMYVPPGAPVPEK

WDDYTWQTSSNPSIFYTYGTAPARISVPYVGISNAYSHFYDGFSKVPLKDQSAALGDSLYGAASLNDF

GILAVRVVNDHNPTKVTSKIRVYLKPKHIRVWCPRPPRAVAYYGPGVDYKDGTLTPLSTKDLTTY

Sabin 1 P1

SEQ ID NO: 17

MGAQVSSQKVGAHENSNRAYGGSTINYTTINYYRDSASNAASKQDFSQDPSKFTEPIKDVLIKTSPML

NSPNIEACGYSDRVLQLTLGNSTITTQEAANSVVAYGRWPEYLRDSEANPVDQPTEPDVAACRFYTLD

TVSWTKESRGWWWKLPDALRDMGLFGQNMYYHYLGRSGYTVHVQCNASKFHQGALGVFAVPEMCLAGD

SNTTTMHTSYQNANPGEKGGTFTGTFTPDDNQTSPARRFCPVDYLFGNGTLLGNAFVFPHQIINLRTN

NCATLVLPYVNSLSIDSMVKHNNWGIAILPLAPLNFASESSPEIPITLTIAPMCCEFNGLRNITLPRL

QGLPVMNTPGSNQYLTADNFQSPCALPEFDVTPPIDIPGEVKNMMELAEIDTMIPFDLSAKKKNTMEM

YRVRLSDKPHTDDPILCLSLSPASDPRLSHTMLGEILNYYTHWAGSLKFTFLFCGSMMATGKLLVSYA

PPGADPPKKRKEAMLGTHVIWDIGLQSSCTMVVPWISNTTYRQTIDDSFTEGGYISVFYQTRIVVPLS

TPREMDILGFVSACNDFSVRLMRDTTHIEQKALAQGLGQMLESMIDNTVRETVGAATSRDALPNTEAS

GPAHSKEIPALTAVETGATNPLVPSDTVQTRHVVQHRSRSESSIESFFARGACVAIITVDNSASTKNK

DKLFAVWKITYKDTVQLRRKLEFFTYSRFDMEFTFVVTANFTETNNGHALNQVYQIMYVPPGAPVPEK

WDDYTWQTSSNPSIFYTYGTAPARISVPYVGISNAYSHFYDGFSKVPLKDQSAALGDSLYGAASLNDF

GILAVRVVNDHNPTKVTSKIRVYLKPKHIRVWCPRPPRAVAYYGPGVDYKDGTLTPLSTKDLTTY

MEF P1

SEQ ID NO: 18

MGAQVSSQKVGAHENSNRAYGGSTINYTTINYYRDSASNAASKQDFAQDPSKFTEPIKDVLIKTAPML

NSPNIEACGYSDRVMQLTLGNSTITTQEAANSVVAYGRWPEYIKDSEANPVDQPTEPDVAACRFYTLD

TVTWRKESRGWWWKLPDALKDMGLFGQNMFYHYLGRSGYTVHVQCNASKFHQGALGVFAVPEMCLAGD

STTHMFTKYENANPGEKGGEFKGSFTLDTNATNPARNFCPVDYLFGSGVLAGNAFVYPHQIINLRTNN

CATLVLPYVNSLSIDSMTKHNNWGIAILPLAPLDFATESSTEIPITLTIAPMCCEENGLRNITVPRTQ

GLPVLNTPGSNQYLTADNYQSPCAIPEFDVTPPIDIPGEVRNMMELAEIDTMIPLNLTNQRKNTMDMY

RVELNDAAHSDTPILCLSLSPASDPRLAHTMLGEILNYYTHWAGSLKFTFLFCGSMMATGKLLVSYAP

PGAEAPKSRKEAMLGTHVIWDIGLQSSCTMVVPWISNTTYRQTINDSFTEGGYISMFYQTRVVVPLST

PRKMDILGFVSACNDFSVRLLRDTTHISQEAMPQGLGDLIEGVVEGVTRNALTPLTPANNLPDTQSSG

PAHSKETPALTAVETGATNPLVPSDTVQTRHVIQKRTRSESTVESFFARGACVAIIEVDNDAPTKRAS

KLFSVWKITYKDTVQLRRKLEFFTYSRFDMEFTFVVTSNYTDANNGHALNQVYQIMYIPPGAPIPGKW

-continued

NDYTWQTSSNPSVFYTYGAPPARISVPYVGIANAYSHFYDGFAKVPLAGQASTEGDSLYGAASLNDFG

SLAVRVVNDHNPTKLTSKIRVYMKPKHVRVWCPRPPRAVPYYGPGVDYKDGLAPLPEKGLTTY

Sabin 2 P1

SEQ ID NO: 19

MGAQVSSQKVGAHENSNRAYGGSTINYTTINYYRDSASNAASKQDFAQDPSKFTEPIKDVLIKTAPML

NSPNIEACGYSDRVLQLTLGNSTITTQEAANSVVAYGRWPEYIRDTEANPVDQPTEPDVAACRFYTLD

TVTWRKESRGWWWKLPDALKDMGLFGQNMFYHYLGRAGYTVHVQCNASKFHQGALGVFAVPEMCLAGD

STTHMFTKYENANPGEKGGEFKGSFTLDTNATNPARNFCPVDYLFGSGVLVGNAFVYPHQIINLRTNN

CATLVLPYVNSLSIDSMTKHNNWGIAILPLAPLDFATESSTEIPITLTIAPMCCEFNGLRNITVPRTQ

GLPVLNTPGSNQYLTADNYQSPCAIPEFDVTPPIDIPGEVRNMMELAEIDTMIPLNLTSQRKNTMDMY

RVELSDTAHSDTPILCLSLSPASDPRLAHTMLGEILNYYTHWAGSLKFTFLFCGSMMATGKLLVSYAP

PGAEAPKSRKEAMLGTHVIWDIGLQSSCTMVVPWISNTTYRQTINDSFTEGGYISMFYQTRVVVPLST

PRKMDILGFVSACNDFSVRLLRDTTHISQEAMPQGIGDMIEGAVEGITKNALVPPTSTNSLPDTKPSG

PAHSKEIPALTAVETGATNPLVPSDTVQTRHVIQRRTRSESTVESFFARGACVAIIEVDNDAPTKRAS

RLFSVWKITYKDTVQLRRKLEFFTYSRFDMEFTFVVTSNYIDANNGHALNQVYQIMYIPPGAPIPGKW

NDYTWQTSSNPSVFYTYGAPPARISVPYVGIANAYSHFYDGFAKVPLAGQASTEGDSLYGAASLNDFG

SLAVRVVNDHNPTRLTSKIRVYMKPKHVRVWCPRPPRAVPYFGPGVDYKDGTLTPLPEKGLTTY

Saukett P1

SEQ ID NO: 20

MGAQVSSQKVGAHENSNRAYGGSTINYTTINYYKDSASNAASKQDYSQDPSKFTEPLKDVLIKTAPTL

NSPNVEACGYSDRVLQLTLGNSTITTQEAANSVVAYGRWPEFTRDDEANPVDQPTEPDVATCRFYTLD

TVMWGKESKGWWWKLPDALRDMGLFGQNMYYHYLGRSGYTVHVQCNASKFHQGALGVFATPEYCLAGD

SDKQRYTSYANANPGEKGGKFYSQFNRDTAVTSPKREFCPVDYLLGCGVLLGNAFVYPHQIINLRTNN

SATIVLPYVNALAIDSMVKHNNWGIAILPLSPLDFAQDSSVEIPITVTIAPMCSEFNGLRNVTAPKFQ

GLPVLNTPGSNQYLTSDNHQSPCAIPEFDVTPPIDIPGEVKNMMELAEIDTMIPLNLENTKRNTMDMY

RVTLSDSADLSQPILCLSLSPASDPRLSHTMLGEVLNYYTHWAGSLKFTFLFCGSMMATGKILVAYAP

PGAQPPTSRKEAMLGTHVIWDLGLQSSCTMVVPWISNVTYRQTTQDSFTEGGYISMFYQTRIVVPLST

PKSMSMLGFVSACNDFSVRLLRDTTHISQSALPQGIEDLITEVAQGALTLSLPKQQDSLPDTKASGPS

HSKEVPALTAVETGATNPLVPSDTVQTRHVIQRRSRSESTIESFFARGACVAIIEVDNEEPTTRAQKL

FATWRITYKDTVQLRRKLEFFTYSRFDMEFTFVVTANFTNTNNGHALNQVYQIMYIPPGAPTPKSWDD

YTWQTSSNPSIFYTYGAAPARISVPYVGLANAYSHFYDGFAKVPLKTDANDQIGDSLYSAMTVDDFGV

LAIRVVNDHNPTKVTSKVRTYMKPKHVRVWCPRPPRAVPYYGPGVDYKDNLNPLSEKGLTTY

Sabin 3 P1

SEQ ID NO: 21

MGAQVSSQKVGAHENSNRAYGGSTINYTTINYYKDSASNAASKQDYSQDPSKFTEPLKDVLIKTAPAL

NSPNVEACGYSDRVLQLTLGNSTITTQEAANSVVAYGRWPEFIRDDEANPVDQPTEPDVATCRFYTLD

TVMWGKESKGWWWKLPDALRDMGLFGQNMYYHYLGRSGYTVHVQCNASKFHQGALGVFAIPEYCLAGD

SDKQRYTSYANANPGERGGKFYSQFNKDNAVTSPKREFCPVDYLLGCGVLLGNAFVYPHQIINLRTNN

SATIVLPYVNSLAIDSMVKHNNWGIAILPLSPLDFAQDSSVEIPITVTIAPMCSEFNGLRNVTAPKFQ

GLPVLNTPGSNQYLTSDNHQSPCAIPEFDVTPPIDIPGEVKNMMELAEIDTMIPLNLESTKRNTMDMY

RVTLSDSADLSQPILCLSLSPAFDPRLSHTMLGEVLNYYTHWAGSLKFTFLFCGSMMATGKILVAYAP

PGAQPPTSRKEAMLGTHVIWDLGLQSSCTMVVPWISNVTYRQTTQDSFTEGGYISMFYQTRIVVPLST

PKSMSMLGFVSACNDFSVRLLRDTTHISQSALPQGIEDLISEVAQGALTLSLPKQQDSLPDTKASGPA

-continued

HSKEVPALTAVETGATNPLAPSDTVQTRHVVQRRSRSESTTESFFARGACVAIIEVDNEQPTTRAQKL

FAMWRITYKDTVQLRRKLEFFTYSRFDMEFTFVVTANFTNANNGHALNQVYQIMYIPPGAPTPKSWDD

YTWQTSSNPSIFYTYGAAPARISVPYVGLANAYSHFYDGFAKVPLKTDANDQIGDSLYSAMTVDDFGV

LAVRVVNDHNPTKVTSKVRIYMKPKHVRVWCPRPPRAVPYYGPGVDYRNNLDPLSEKGLTTY

Primer P1F

SEQ ID NO: 22

GCGAGTTGGATTGGCCATCCAGTG

Primer P1R

SEQ ID NO: 23

TGGAAGGTGGGTCCCACAAACGAC

EXAMPLES

The invention will be further clarified by the following examples, which are intended to be purely exemplary of the invention and are in no way limiting.

Example 1—Identification of Stabilising Mutations in Type 3 Poliovirus

Type 3 Sabin Vaccine Strain

One of the two main attenuating mutations in the type 3 Sabin vaccine strain is in the structural protein VP3 at residue 91 (3091), which is a serine in the wild type Leon strain and a phenylalanine in the vaccine strain. Amino acid 91 of VP3 lies at the interface between protomers and makes virus growth and capsid assembly temperature sensitive in vitro. Infants given oral polio vaccine eventually excrete virus in which the mutation is either reverted or suppressed and the suppressor mutations have been shown to increase the stability of capsid assembly intermediates.

Additional mutations that suppress the phenotype were identified by growing the type 3 vaccine strain at semi-permissive temperatures. The mutations identified that increase capsid stability are listed in Table 1 herein. Eight of the mutations were selected for further study (see Table 5, together with how they were identified and their origin). The mutations shown in Table 5 were selected from the total identified on the basis that if two mutations acted at the same point in the structure, only one was studied further.

TABLE 5

Mutations that suppress the effect of the capsid destabilising mutation VP3 91F in the Sabin type 3 strain.

| Mutation | Location | Basis of identification |
|---|---|---|
| VP2 18 leucine-isoleucine | Beta sheet at pentamer interface | Isolates from vaccinees and in vitro passage at elevated temperatures |
| VP2 215 leucine-methionine | Protomer interface | Isolates from vaccinees |
| VP2 241 aspartate-glutamate | VP2/VP3 interface, buried | In vitro passage at elevated temperatures |
| VP3 19 histidine-tyrosine | Internal network, β-annulus beneath 5 fold axis | In vitro passage at elevated temperatures |
| VP3 85 leucine-phenylalanine | Beta sheet at pentamer interface | In vitro passage at elevated temperatures |
| VP3 91 phenylalanine-serine | Protomer interface | Isolates from vacinees and in vitro passage at elevated temperatures |
| VP1 54 alanine-valine | Internal network at 3 fold axis | Isolates from vaccinees and in vitro passage at elevated temperatures |
| VP1 132 phenylalanine-leucine | Capsid pocket | In vitro passage at elevated temperatures |

Type 3 Leon Strain

Mutations identified as candidate capsid stabilising changes were introduced into Leon, the virulent precursor of the Sabin vaccine strain of type 3 in different combinations. Derivation of the pT7/Leon cDNA clone has have been described previously (Stanway G, et al. Arch Virol. 1984; 81(1-2):67-78). Briefly, a ribozyme sequence was inserted between the T7 promoter and the polio cDNA so that RNA transcripts began with the authentic 5' end. In order to replace the P1 coding region a SacII site was introduced using standard PCR methods without coding change at nucleotides 3408-13.

Capsid regions from Mahoney, MEF-1 and Saukett were then introduced precisely using standard PCR methods. Mutations were introduced into the capsid protein coding regions of these clones using synthetic DNA and suitable restriction enzyme cleavage sites.

Viruses were recovered by transfection of HEp2C monolayers in 25 $cm^2$ flasks with 2 μg T7 transcripts followed by incubation at 33° C., 35° C. or 37° C. until complete cytopathic effect (CPE) was apparent. Transfected cells showing no signs of CPE at 7 days were frozen and cell lysates were blind-passaged on fresh HEp2c cells for a further 7 days.

It was hypothesized that if the capsid were stabilised beyond what is optimal for assembly or uncoating, growth would be slowed down. It was found that viruses possessing three or more mutations grew significantly more slowly than the parental Leon when recovered and grown in HEp2c cells at 35° C. a temperature fully permissive for the wild type strain. On passage at 37° C., faster growing variants emerged which had lost one or more of the stabilising capsid mutations or introduced additional mutations including one in VP4 at residue 67 where a threonine replaced an alanine and another in VP1 at residue 105 where a threonine replaced a methionine, in both cases as found in the wild-type 3 virus, Saukett (as shown in Table 6). As these changes rescued a virus with a more stable structure it was concluded that the amino acids introduced had a destabilising effect. Thus structures with the parental version of these residues (VP4 67A, i.e. alanine at residue 67 of VP4 and VP1 105M, i.e. methionine at residue 105 of VP1) were thought likely to be more stable than those that did not.

TABLE 6

Mutations that destabilise capsids in super-optimally stable Leon mutants and are also present in wild-type Saukett.

| Mutation | Location |
|---|---|
| VP4 67 alanine*-threonine | Internal network near three fold axis |
| VP1 105 methionine*-threonine | North wall of canyon |

*amino acid present in stable capsid

Origin of Type 3 Saukett Strain SC8

The virulent, wild-type Saukett type 3 strain that is used for production of inactivated polio vaccine (type 3) has capsid proteins that differ from those of Leon at 14 amino acid positions, some in antigenic sites. Wild-type Saukett already has the thermostable version of two of the mutations identified in the Sabin type 3 strain (VP3 91 serine and VP1 54 valine). Saukett also possesses the destabilising residue of the two mutations identified by passage of the Leon constructs. Constructs were therefore made in which the remaining 6 amino acids in Table 5 and the 2 mutations in Table 6 were exchanged for the stabilising forms, so giving Saukett-SC8 with eight amino acid differences from the Saukett sequence as shown in Table 7.

TABLE 7

Mutations included in capsid stabilised mutants for further study: Saukett-SC8.

| Mutation | Location |
|---|---|
| T4067A | Internal network near three fold axis |
| L2018I | Beta sheet at pentamer interface |
| L2215M | Protomer interface |
| D2241E | VP2/VP3 interface, buried |
| H3019Y | Internal network, tube below 5-fold axis |
| L3085F | Beta sheet at pentamer interface |
| T1105M | North wall of canyon |
| F1132L* | Pocket |

Example 2—Identification of Stabilising Mutations in Type 1 (Mahoney-SC7) and Type 2 (MEF-SC5a) Poliovirus Strains Origin of Type 1 Mahoney SC7 and Type 2 MEF SC5a Strains The similarities in the structures of type 1, 2 and 3 poliovirus suggested that the stabilising mutations identified for type 3 might have a stabilising effect on types 1 and 2. However the type 1 Mahoney strain used in most current IPV production already possesses four of the mutations incorporated into Saukett-SC8. The remaining four were introduced in addition but the construct produced no detectable capsid proteins or signs of infection.

A second identification strategy was therefore followed, which involved constructing a mutant of Mahoney possessing a phenylalanine at residue 91 of VP3 (3091), as in the Sabin 3 strain; this virus was recovered and shown to be temperature sensitive in its growth in vitro. HEp2c cells were transfected with RNA transcripts from this construct, incubated at the non-permissive temperature of 39° C. until at least 80% cytopathic effect (CPE) was seen, and the resulting progeny examined by deep sequencing to identify subpopulations of non-temperature sensitive mutants. The transfection was independently repeated six times and each population subject to deep sequencing twice to eliminate deep sequencing amplification artefacts.

To carry out the deep sequencing, RNA was extracted using Roche High Pure® viral RNA kits. Water only controls were extracted, amplified and sequenced in parallel with each set of samples. Capsid coding regions were amplified in duplicate by one-step RT-PCR using a SuperScript III HiFi kit and primers P1F (5'-GCGAGTTGGATTGGCCATCCAGTG-3', SEQ ID NO:22) and P1R (5'-TGGAAGGTGGGTCCCACAAACGAC-3', SEQ ID NO:23). Products were purified using AMPure XP® magnetic beads (Beckman Coulter), quantified using Qubit® High Sensitivity dsDNA assay (Life Technologies), analysed on an Agilent® High Sensitivity DNA chip (Agilent) and diluted to 0.2 ng/μl in molecular grade Tris-EDTA, pH8.0.

Sequencing libraries were prepared using Nextera XT® reagents (Illumina) and the manufacturer's protocol, and sequenced on a MiSeq® using a 2×251 paired-end v2 Flow Cell (Illumina). Quality trimming and assembly were carried out and reads were then mapped to parental reference sequences using Genious R7® (Biomatters) software and SNPs present at ≥0.5% identified. Only those SNPs present in both replica amplicons were retained.

The mutations identified are shown in Table 1 herein. Some of the mutations identified in this way were selected and inserted into Mahoney to give Mahoney SC7 and are shown in Table 8.

The same strategy was followed for the type 2 strain MEF-1 and the mutations identified and inserted into MEF-SC5a are given in Table 8. Reversion of VP3-91 (F-S) occurred in a significant proportion of both populations.

TABLE 8

Mutations included in capsid stabilised mutants for further study: Mahoney SC7 and MEF SC5a.

| Virus | Mutation | Location |
|---|---|---|
| Mahoney-SC7 | R4018G | Internal network near three fold axis |
| | T2025A | Pentamer interface |
| | D2057E | Pentamer interface |
| | L3119M | VP2/VP3 interface |
| | Q3178L | Protomer interface |
| | V1196L | Pocket |
| | H1248P | Protomer interface |
| MEFSC5a | L3085F | Beta sheet at pentamer interface |
| | Q3178L | Protomer interface |
| | T1041I | Pentamer interface |
| | F1134L* | Pocket |
| | Y1159F | Pocket |

*F1134L in type 2 is equivalent to F1132L in type 3

Example 3—Location of the Stabilising Mutations in the Three Poliovirus Serotypes The position of all the altered residues within a protomeric subunit and the location of the relevant capsid features were mapped onto a poliovirus capsid crystal structure, as shown in FIG. 2. Significantly, none of the candidate stabilising mutations selected in any of the three serotypes occurred at residues previously identified as contributing to antigenic sites. They were therefore thought unlikely to alter the antigenic structures of the particles in which they were present.

Example 4—Infection by Candidate Thermostable Mutants

Figure 3:
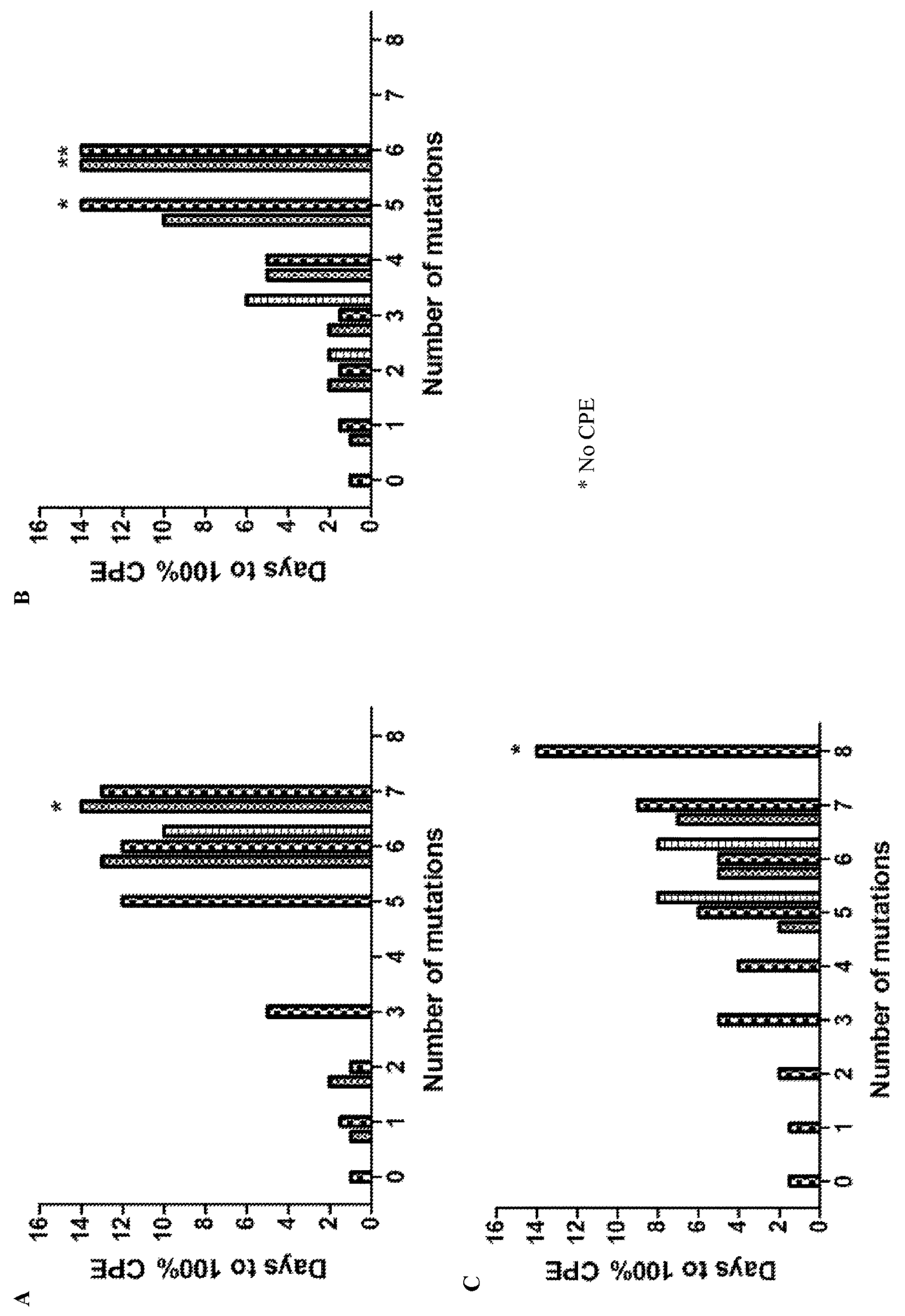
FIG. 3: Stabilisation of virus particles reduces infectivity. Different numbers and combinations of the stabilising mutations described in Tables 4 & 6/7, as well as others identified in similar ways, were introduced into capsid-coding sequences of infectious clones. HEp2c cells were transfected with infectious RNA transcripts and incubated at 37° C. until 100% cytopathic effect (CPE) was observed, or frozen after 7 days if no CPE was apparent. Clarified supernatants of these cell cultures were blind passaged into fresh HEp2c cells and cells incubated at 37° C. until 100% CPE was observed or for a further 7 days. (A) type 1 Mahoney capsid mutants, (B) type 2 MEF-1 capsid mutants, (C) type 3 Leon capsid mutants. * no CPE observed after blind passage.
Figure 6:
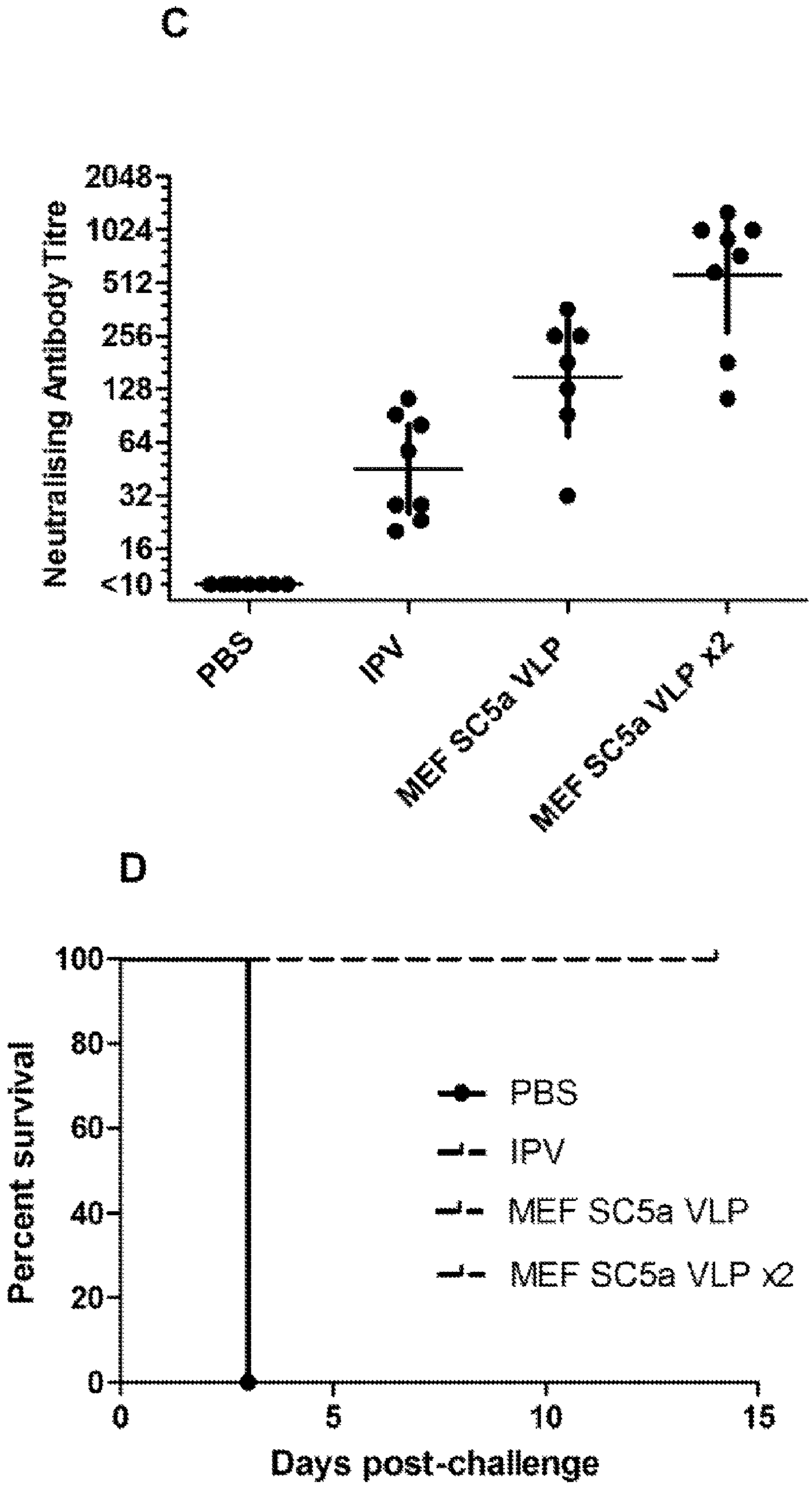
FIG. 6: Seroconversion and protection against challenge induced by VLPs. Transgenic mice expressing the human poliovirus receptor were immunised intraperitoneally once or twice (×2) with PBS or 0.5 human dose equivalents of IPV or VLPs (A, B-type 1; C, D-type 2; E, F-type 3) then challenged intramuscularly with 25 PD50 of homologous wild type virus. Graphs A, C & E show neutralising antibody titres against homologous serotype viruses in blood samples taken the day prior to challenge. Graphs B, D & F show survival rates following challenge with (B) type 1 Mahoney, (D) type 2 MEF-1 and (F) type 3 Saukett. Bars (A, C & E) indicate 95% CI of the geometric mean titre.
Figure 6:
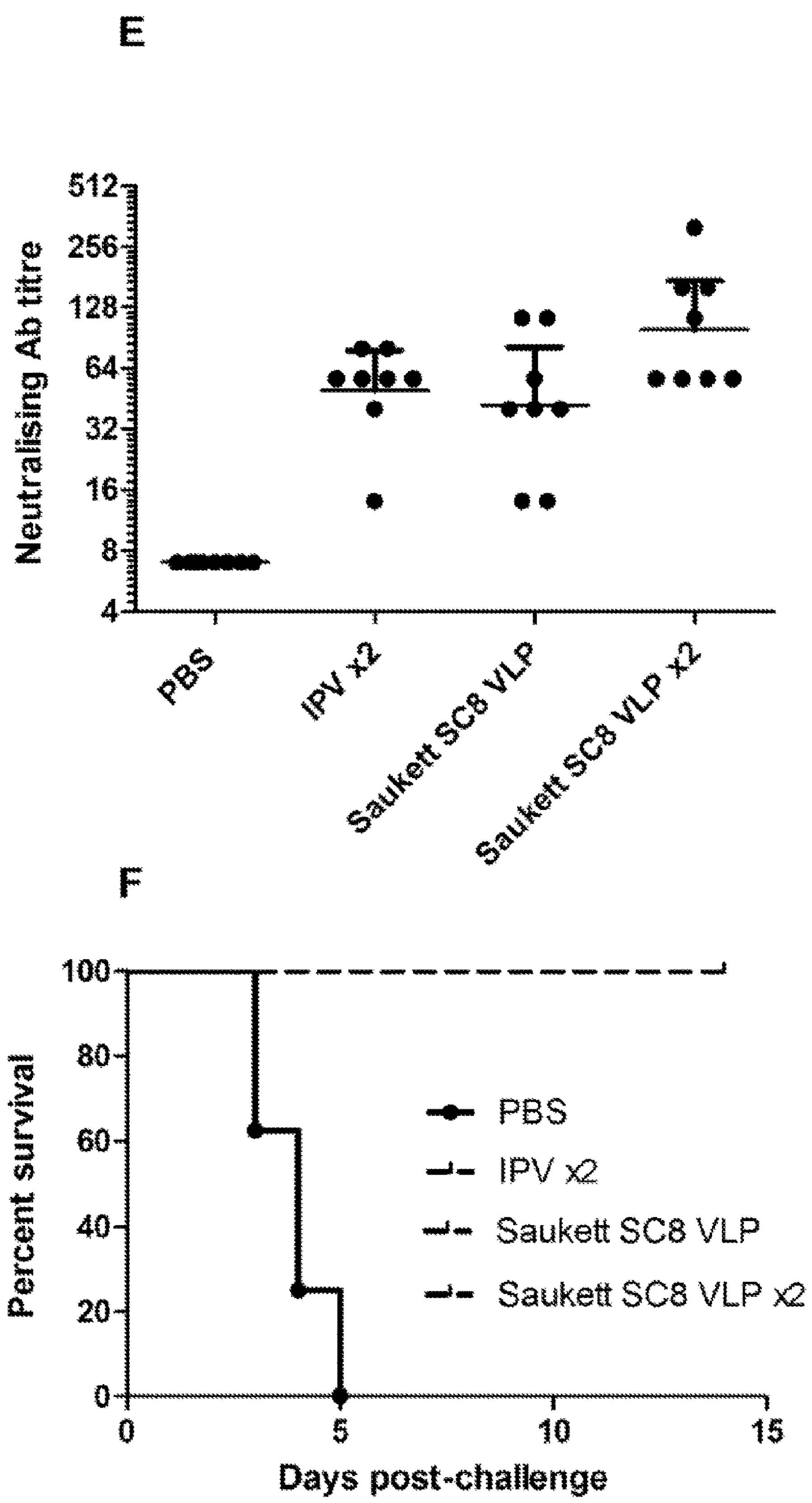

Genomes were constructed which included varying numbers of the candidate mutations identified and RNA transfected into Hep2C cells which are permissive for polio growth. The results obtained are shown in FIG. 3 where it can be seen that the time to full lysis of the cell culture at 37° C. increased with the number of mutations inserted until no CPE could be detected at all even after blind-passage (SC8 containing 8 mutations in the wild type Leon for type 3, SC5b, SC6a & SC6b containing 5 or 6 mutations in the wild type MEF1 for type 2 and SC7 containing 7 mutations in the wild type Mahoney for type 1). At 33° C. incubation times were even longer. Transfection of the type 3 construct Saukett SC8, like Leon SC8, did not result in any detectable CPE. The properties of Saukett SC8 (type3) MEF SC5a (type 2) and Mahoney SC7 (type1) were examined further.

Tables 9 and 10 show the effect of various combinations of stabilising mutations identified in Examples 1 and 2 in type 1 and 2 poliovirus respectively. The temperature at which D antigen (DAg) reactivity of the VLP is reduced by 50% and the number of days required to give 100% CPE by the corresponding virus were determined for all mutants. These values are indicators of the stability of the modified polioviruses (both an increase in temperature for a 50% reduction in DAg and an increase in the time to 100% CPE correlate with increasing stability). The corresponding data for the SC8 type 3 mutant is provided in Table 11 for comparison.

TABLE 9

Further combinations of mutations included in capsid stabilised type 1 mutants

| Mutation | Location | wt | SC1 | SC1a | SC2 | SC2a | SC2c | SC2d | SC3 | SC4 | SC5b | SC6 |
|---|---|---|---|---|---|---|---|---|---|---|---|---|
| R4018G | Internal network | | | | | | ✓ | ✓ | ✓ | | ✓ | ✓ |
| T2025A | Pentamer interface | | | | | | ✓ | | ✓ | | ✓ | ✓ |
| D2057E | Pentamer interface | | | | | | | ✓ | ✓ | | ✓ | ✓ |
| L3119M | Internal | | | | ✓ | | | | | ✓ | | |
| Q3178L | Protomer interface | | ✓ | | ✓ | | | | | ✓ | ✓ | ✓ |
| V1196L | Pocket | | | | | | | | | | | ✓ |
| A1231V | Protomer | | | | | ✓ | | | | ✓ | | |
| H1248P | Protomer interface | | | ✓ | | ✓ | | | | ✓ | ✓ | ✓ |
| Temp at which DAg reduced by 50% (° C.) | | 37.5 | 41.5 | 40 | 42.5 | 42 | 47 | 43 | 43.5 | 45 | 45 | 53 |
| Infectivity (days to CPE) | | 1 | 2 | 1 | 2 | 2 | <4 | <4 | 5 | ND | 12 | 12 |

| Mutation | Location | SC6a | SC6b | SC6c | SC6d | SC7 | SC7b | SC7c | SC7d | SC8 |
|---|---|---|---|---|---|---|---|---|---|---|
| R4018G | Internal network | ✓ | ✓ | ✓ | ✓ | ✓ | ✓ | ✓ | ✓ | ✓ |
| T2025A | Pentamer interface | ✓ | ✓ | ✓ | | ✓ | ✓ | ✓ | | ✓ |
| D2057E | Pentamer interface | ✓ | ✓ | | ✓ | ✓ | ✓ | | ✓ | ✓ |
| L3119M | Internal | | ✓ | ✓ | ✓ | ✓ | ✓ | ✓ | ✓ | ✓ |
| Q3178L | Protomer interface | ✓ | ✓ | ✓ | ✓ | ✓ | ✓ | ✓ | ✓ | ✓ |
| V1196L | Pocket | | | | | ✓ | | ✓ | ✓ | ✓ |
| A1231V | Protomer | ✓ | | ✓ | ✓ | | ✓ | ✓ | ✓ | ✓ |
| H1248P | Protomer interface | ✓ | ✓ | ✓ | ✓ | ✓ | ✓ | ✓ | ✓ | ✓ |
| Temp at which DAg reduced by 50% (° C.) | | 47 | 52 | 47.5 | 45 | 51 | 52 | 49 | 45 | 49 |
| Infectivity (days to CPE) | | 10 | 13 | 12 | 12 | >7 | 13 | 11 | 13 | —* |

*No CPE observed over the time course of the experiment.

TABLE 10

| Further combinations of mutations included in capsid stabilised type 2 mutants | | | | | | | | | | | | | | | | |
|---|---|---|---|---|---|---|---|---|---|---|---|---|---|---|---|---|
| Mutation | Location | wt | SC1 | SP1 | SC2 | SP2a | SP2b | SP3 | SC3a | SC3b | SC4a | SC4b | SC5a | SC5b | SC6a | SC6b |
| I4057V | internal network 3-fold | | | | | | | | | | | | | | | ✓ |
| D2057A | pentamer interface | | | | | | | | | | | | | | | ✓ |
| L3085F | pentamer interface | | ✓ | | | | | | ✓ | | ✓ | | ✓ | | ✓ | |
| Q3178L | protomer interface | | | | ✓ | | | | ✓ | ✓ | ✓ | ✓ | ✓ | ✓ | ✓ | ✓ |
| T1041I | pentamer interface | | | | ✓ | | | | ✓ | ✓ | ✓ | ✓ | ✓ | ✓ | ✓ | |
| V1107I | protomer interface | | | | | | | | | | | | | | | ✓ |
| F1134 L | pocket | | | ✓ | | ✓ | ✓ | ✓ | | ✓ | ✓ | ✓ | ✓ | ✓ | ✓ | ✓ |
| Y1159F | pocket | | | | | ✓ | | ✓ | | | | ✓ | ✓ | ✓ | ✓ | |
| V1183L | pocket | | | | | | | | | | | | | | | ✓ |
| I1194V | pocket | | | | | | ✓ | ✓ | | | | | | ✓ | ✓ | |
| Temp at which DAg reduced by 50% (° C.) | | 38 | 41 | 44 | 40 | 45 | 43 | 47 | 40 | 43 | 57 | 47 | 55 | 52 | 62 | 58 |
| Infectivity (days to CPE) | | 1 | <2 | 1 | <2 | 2 | 2 | 6 | <2 | 2 | 5 | 5 | 11 | —* | —* | —* |

*No CPE observed over the time course of the experiment.

TABLE 11

| Further data for the type 3 SC8 mutant | | | |
|---|---|---|---|
| Mutation | Location | wt | SC8 |
| T4067A | Internal network | | ✓ |
| L2018I | Pentamer interface | | ✓ |
| L2215M | Protomer interface | | ✓ |
| D2241E | VP2/VP3 interface | | ✓ |
| H3019Y | Internal network | | ✓ |
| L3085F | Pentamer interface | | ✓ |
| T1105M | North wall of canyon | | ✓ |
| F1132L | Pocket | | ✓ |
| Temp at which DAg reduced by 50% (° C.) | | 33 | 55 |
| Infectivity (days to CPE) | | 1 | —* |

*No CPE observed over the time course of the experiment.

Example 5—Thermostability of Particles Produced by Transfection

Poliovirus particles express two distinct antigens. D antigen is associated mainly with infectious virus and C antigen with non-infectious particles, for example after heating; empty capsids, outside the cell, are particularly prone to convert to C antigen specificity. IPV potency is expressed in D antigen units as D antigen is thought to be the inducer of a protective immune response. An ELISA developed for quantitating the antigen content of commercial vaccines was adapted for measuring the D antigen or C antigen content of virus particle preparations, based on the use of D antigen specific monoclonal antibodies against types 1, 2 and 3, and C antigen specific antibodies for types 1 and 3. No C specific antibody was available for type 2.

Mouse L cells, which lack the receptor for poliovirus, and hence are not infectable by whole virus, were electroporated with full length RNA transcripts from constructs encoding the wild type or capsid stabilised mutants to give a single cycle of infection. Overnight incubation produced predominantly C antigenic empty particles for wild type constructs so 6 hour incubations were used in these cases; production of predominantly D antigenic empty particles for mutant constructs after overnight incubation was an early indication that the introduced mutations had a significant stabilising effect.

The particles produced were purified on sucrose gradients. In more detail, particle preparations were made by high-efficiency electroporation of full-length RNA transcripts into mouse L cells. Linearised clones (1 μg) were transcribed using a T7 Megascript® kit (Life Technologies); cells from a 90% confluent 75 $cm^2$ flask were removed by trypsinisation, washed and resuspended in HeBS (20 mM HEPES, 137 mM NaCl, 5 mM KCl, 0.7 mM $Na_2HPO_4$, 6 mM glucose, pH 7.05), electroporated with RNA transcripts (250V, 250 μF, 360Ω) then returned to the flask and incubated in DMEM at 37° C. overnight or for 6h. Six flasks were used for each construct. Cell sheets were then frozen at −70° C. and thawed and cell debris removed by centrifugation. Igepal was added to supernatants to a final concentration of 0.1% and viral particles were concentrated by centrifugation at 4° C. through a 10 ml 30% sucrose cushion made up in lysis buffer (6-salt PBS containing 0.5% sodium deoxcholate, 20 mM EDTA and 1% Igepal). Pellets were resuspended in 1 ml 6-salt PBS per six flasks, layered on 10 ml 15%-30% sucrose gradients in lysis buffer and centrifuged at 4° C. for 12h at 18,000 rpm in a Beckman SW41® rotor before harvesting into 20 0.5 ml fractions.

Fractions were screened by C or D antigen specific ELISA to identify virus and empty capsid peaks. Specifically, a non-competitive sandwich ELISA assay was used to measure the D-antigen content of poliovirus. Briefly, two-fold dilutions of antigen were captured with a serotype-specific polyclonal antibody, then detected using serotype-specific, D antigen or C antigen specific monoclonal antibodies followed by anti-mouse peroxidase conjugate. The D antigen content of each test sample was evaluated against a reference of assigned D antigen content by parallel line analysis (Combistats). For D antigen specific ELISA the monoclonal antibodies used were 234 for type1, 1050 for type 2 and 520 for type 3, and for C antigen specific ELISA 15848 for type 1 and 517 for type 3. No C specific type 2 antibody was available.

Type 1 and type 3 peak fractions were also screened by immunoblotting with a VP2 specific antibody; virion fractions contained VP2 and empty capsid fractions contained VP0. Primary antibodies for immunoblots were rabbit anti-VP2 peptide sera 8271 for type 1 and R268 for type 3.

The fractions corresponding to the virions and empty capsids were then subjected to thermostability testing. The temperature at which a conformational change from D to C antigenicity occurred was determined by heating at a range of temperatures from 30-60° C. followed by D and C antigen ELISA (the latter where possible). Samples were diluted in 6-salt PBS to twice the concentration required to obtain an OD of 1.0 in D antigen ELISA, duplicate samples were heated for 10 min at each temperature then diluted 1:1 with 4% dried milk in 6-salt PBS and cooled on ice. D and C antigen content was measured by ELISA. Long-term stability was analysed by incubating, at 37° C., multiple aliquots of IPV, virus and empty capsid samples, diluted in 6-salt PBS to twice the concentration required to obtain an OD of 1.0 in D antigen ELISA. Samples were removed at intervals and analysed by D Antigen ELISA.

The results for the unmodified type 3 strain Leon are shown in FIG. 4A for the infectious virus and in FIG. 4B for the empty capsids where there was a high starting background of C antigen as expected. The loss of D antigen was mirrored by an increase in C antigen content; for the infectious particles the temperature at which 50% of D antigen was lost was 42° C. while it was 33° C. for the empty capsids.

The results for empty capsid preparations of all wild type and selected stabilised capsid mutants are summarised in Table 12. The modified empty capsids converted from D to C antigen specificity at 54° C., 56° C. and 55° C. for the stabilised forms of types 1, 2 and 3 respectively compared to 36° C., 42° C. and 33° C. for the corresponding wild type strains. The temperatures at which commercial IPV converted from D to C antigen specificity ranged from 49° C. to 52° C. for the three serotypes. By this assay therefore all of the empty capsids from the mutant strains selected for improved thermostability were more stable than the currently marketed IPV produced by formalin treatment of live virus. Assays using different D antigen specific MAbs directed against other antigenic sites gave indistinguishable results and all the antibodies tested reacted equally with wild type and stabilised particles in ELISA.

TABLE 12

Thermostability of empty capsid (VLP) preparations.

| Particle | | Temperature* |
|---|---|---|
| Native empty capsid (WT1) | | 36° C. |
| Native empty capsid (Mah SC7) | | 54° C. |
| Native empty capsid (WT2) | | 42° C. |
| Native empty capsid (MEF SC5a) | | 56° C. |
| Native empty capsid (WT3) | | 33° C. |
| Native empty capsid (Skt SC8) | | 55° C. |
| IPV (formaldehyde treated) | Type 1 | 49° C. |
| | Type 2 | 52° C. |
| | Type 3 | 52° C. |

*at which native antigenicity is reduced by 50% after a 10 minute incubation

The study involved exposure at elevated temperature for ten minutes. A study that would better imitate real use involved exposing the materials to 37° C. for prolonged periods; the results are shown in FIG. 5 for the D antigen loss, in comparison with IPV, of both the empty capsid (VLP) peak and the virus peak relative to samples incubated at 4° C. for the same period. The 4° C. samples showed no significant loss of reactivity throughout the incubation period and were used as controls for inter-assay variability. For type 3 (FIG. 5C) IPV had lost all activity by the second time point at 62 days; it is possible that total loss occurred much earlier. The type 3 Saukett SC8 virus retained full activity for 180 days and the empty capsids of SC8 (SC8 VLP) retained 56% of the activity at 62 days and 13% at 180 days. The type 2 component of IPV (FIG. 5B) lost D antigen content less quickly than observed for type 3 but was reduced to 41% of the starting value at day 62 and 8% by day 111. The virus particle of the mutant type 2 virus MEF-SC5a retained 75% of starting D antigen content on day 111, and retained 64% at day 180. The empty capsids of MEF-SC5a retained 82% of starting D antigen content by day 110 and 52% of the activity at 180 days. The type 1 component of IPV (FIG. 5A) retained 35% of D antigen content by day 43 and only 4% by day 86; reactivity was abolished by day 182. Neither the virus particle nor the empty capsids of the mutant type 1 virus Mah-SC7 lost any D antigen content by day 86; the empty capsids of MEF-SC7 retained 87% of D antigen content on day 182. The stabilised empty capsids were therefore strikingly more stable than IPV at 37°. If this were also true of a commercial product it could survive well outside the cold chain.

Example 6—Immunogenicity in Rats

It is known that the type 2 component of Sabin IPV is less immunogenic than the wild type 2 strain in classical IPV an observation that has not previously been explained in a satisfactory way. It was therefore necessary to investigate the immunogenicity of empty capsids (or VLPs) of the stabilised strains to compare them to classical IPV.

The immunogenicity assay of commercial IPV involves measuring the antigen content, usually by ELISA as above, and then immunising rats with a range of dilutions based on the human dose. The proportion of animals seroconverting at a specific cut off in neutralisation assays is compared to that seen with a reference preparation tested at the same time and a relative potency can be calculated. Immunogenicity was assessed using Pharmacopieal methods established at NIBSC for the release of IPV lots. D antigen content was measured by ELISA and immunogenicity was assessed in Wistar rats. Readout was based on the proportion of animals having a neutralisation titre above a predetermined cut off as given in Table 13.

In this test the type 2 strain used in most current production induces a greater serological response and the cut off is therefore far higher. Results for type 1, 2 and 3 are shown in Table 13.

TABLE 13

Immunogenic potency of strains in rats.

Type 1: Proportion of animals responding at a dilution endpoint titre of >4

| Sample | 32 D Antigen Units | 16 D Antigen Units | 8 D Antigen Units | 4 D Antigen Units |
|---|---|---|---|---|
| Type 1 IPV | 9/10 | 5/10 | 2/10 | 1/10 |
| Mah SC7 VLP | 10/10 | 10/10 | 10/10 | 10/10 |

Type 2: proportion of animals responding at a dilution endpoint titre of >512

| Sample | 8 D Antigen Units | 4 D Antigen Units | 2 D Antigen Units | 1 D Antigen Unit |
|---|---|---|---|---|
| Type 2 IPV | 8/10 | 8/10 | 2/10 | 2/10 |
| MEF SC5a VLP | 10/10 | 9/10 | 8/10 | 6/10 |

TABLE 13-continued

| Immunogenic potency of strains in rats. | | | | |
|---|---|---|---|---|
| Type 3: proportion of animals responding at a dilution endpoint titre of >4 | | | | |
| Sample | 28 D antigen Units | 14 D Antigen Units | 7 D Antigen Units | 3.5 D Antigen Units |
| Type 3 IPV | 9/10 | 7/10 | 2/10 | 3/10 |
| SktSC8 VLP | 10/10 | 10/10 | 10/10 | 10/10 |

The thermostable VLPs MahSC7 (type 1) and SktSC8 (type 3) caused seroconversion in all animals at all doses given, whereas the responses in animals given the same doses of classical IPV spanned the 50% response dose. For type 2 the responses in animals given IPV spanned the 50% end point and the potency of the SC5a VLPs was at least four fold higher. The stabilised VLPs are therefore at least four times more immunogenic than the equivalent IPV component.

Example 7—Protection from Challenge in Mice

Transgenic mice carrying the human receptor for poliovirus (TgPVR) are susceptible to infection and paralysis.

TgPVR mice of both sexes (8 per test group) received one or two intraperitoneal injections of PBS (controls) or the equivalent D antigen corresponding to 0.5 human doses of purified VLPs or the IPV European reference BRP. VLP preparations were shown to be non-infectious by inoculation of HEp2c monolayers and blind-passage after 7 days. The second dose, where given, was on day 14. On day 35 blood samples were taken and mice were challenged intramuscularly with the equivalent of 25 times the $PD_{50}$ of the relevant serotype of wild type poliovirus (Mahoney type 1, MEF-1 type 2 or Saukett type 3) then monitored for any signs of paralysis for 14 days. The results are shown in FIGS. 6A-F which also show the pre-challenge neutralising antibody titres. In all cases the stabilised capsids given as either one or two doses were more immunogenic than IPV and protected all animals from challenge with the corresponding virulent virus.

Ethics Statement

All animal experiments were performed under licenses granted by the UK Home Office under the Animal (Scientific Procedures) Act 1986 revised 2013 and reviewed by the internal NIBSC Animal Welfare and Ethics Review Board. The TgPVR mouse and rat immunogenicity experiments were performed under Home Office licences PPL 80/2478 and PPL 80/2050 which were reviewed and approved by the NIB SC Animal Welfare and Ethics Review Board before submission.

CONCLUSIONS

The production of empty capsids by expression of poliovirus proteins in recombinant baculovirus-infected insect cells that did not involve poliovirus growth was reported more than two decades ago, but the particles were too unstable to be useful as a vaccine candidate. Immunogenic, but unstable, VLPs were also produced by recombinant expression in yeast. The work described herein represents the first development of stable empty capsids, also known as poliovirus like particles (VLPs). The present inventors developed an innovative approach, in which candidate stabilising modifications were identified and then multiple changes introduced into capsid proteins in combination. In more detail, the methods used herein involved a mutation known to be present in the type 3 Sabin vaccine strain of poliovirus that destabilises capsid assembly intermediates (including empty capsids) without affecting virion stability. Thus revertants from vaccinees and other sources were thought likely to possess mutations that restore assembly and increase empty capsid stability. Stabilising mutations in the type 1 and 2 strains were identified by inserting the destabilising Sabin type 3 mutation, selecting in transfected cells at non permissive temperature and screening for revertant genomes by deep sequencing. The approach could also be used to guide selection for other, non-polio, picornaviruses. In some cases stabilising mutations found for type 3 were already present in the type 1 and type 2 viruses.

In most cases the structural locations of the mutations responsible for stabilising empty capsids provide insight into their mechanisms of action. Thus, some mutations appear to act by stabilising interfaces between particle subunits; others may stabilise contacts within subunits including those with the "pocket factor", thought to be a short chain fatty acid that is present in all polioviruses that acts to stabilise particles against conformational transitions, yet others plausibly strengthen interactions between subunits in the internal network that hold subunits together, such as the tube-like beta-annulus structure beneath the 5-fold axis. The overall strategy may be useful in the development of stable VLP vaccines for other picornaviruses.

Licensing and regulation of a new vaccine would normally require a clinical trial that demonstrates efficacy against the target disease. This is clearly impractical for a new polio vaccine where the number of cases in the world is approaching zero. There are precedents for other approaches; Sabin based IPV is licensed in China and Japan on the results of immunogenicity studies and guidance is provided in WHO guidelines on the types of clinical and preclinical trials that might be done. Meningitis C vaccine was licensed and implemented in the UK on the basis of immunogenicity data from clinical trials, and Human Papilloma vaccines were licensed on their ability to prevent non-cancerous lesions not cervical cancer. The decision on whether to license a vaccine lies with the National Regulatory Authorities (NRAs) rather than WHO, but these examples prove that it is possible to gain approval without direct evidence of clinical efficacy from studies showing protection from natural challenge.

The final VLPs studied were extremely stable compared to IPV and have potential utility as a vaccine that would not require a cold chain. Moreover, the VLPs were more immunogenic than IPV made from the equivalent strains in the animal model used for testing IPV potency and in challenge studies in transgenic mice. Without being bound by theory, is possible that this is partly because the VLPs, unlike IPV, were not treated with formalin. The viruses from which they were derived had lost infectivity presumably because they were unable to uncoat by virtue of their hyperstable capsids. The properties of the VLPs make them a very promising vaccine candidate.

The invention claimed is:

1. A poliovirus-like particle (VLP) which comprises modifications relative to the poliovirus particle from which the VLP is derived which stabilise the VLP, wherein:

(a) the VLP is derived from a type 1 poliovirus and comprises the following mutations: R4018G, T2025A, D2057E, L3119M, Q3178L and H1248P;

(b) the VLP is derived from a type 2 poliovirus and comprises the following mutations: L3085F, Q3178L, T1041I, F1134L and Y1159F;

(c) the VLP is derived from a type 2 poliovirus and comprises the following mutations: I4057V, D2057A, Q3178L, V1107I, F1134L and V1183L; or (d) the VLP is derived from a type 3 poliovirus and comprises the following mutations: T4067A, L2018I, L2215M, D2241E, H3019Y, L3085F, T1105M and F1132L;

wherein the modifications relative to the poliovirus particle from which the VLP is derived stabilises the native-antigenic conformation of the poliovirus capsid.

2. The poliovirus-like particle (VLP) of claim 1, which is:

(a) derived from a wild-type poliovirus or from a vaccine strain; and (b) derived from a type 1, type 2 or type 3 poliovirus.

3. The poliovirus-like particle (VLP) of claim 2, which is derived from:

(a) a type 1 poliovirus selected from Mahoney and Sabin 1;

(b) a type 2 poliovirus selected from MEF and Sabin 2; or (c) a type 3 poliovirus selected from Saukett and Sabin 3.

4. The poliovirus-like particle (VLP) of claim 1, which further comprises at least one additional modification relative to the poliovirus particle from which the VLP is derived; wherein said at least one additional modification is in the pocket domain and:

(a) the VLP is derived from a type 1 poliovirus and the at least one additional modification is V1196L;
(b) the VLP is derived from a type 2 poliovirus and the at least one additional modification is Y1159F, V1183L and I1194V; or
(c) the VLP is derived from a type 3 poliovirus and the at least one additional modification is M1260I.

5. The poliovirus-like particle (VLP) of claim 1, which comprises:
(a) one or more additional modifications within one or more of the pocket domain, the protomer interface and/or the pentamer interface; and/or
(b) at least one further modification in one or more additional structural domain.

6. The poliovirus-like particle (VLP) of claim 5, wherein the one or more additional structural domain is selected from:
(a) a VP2/VP3 interface;
(b) an internal network; and/or
(c) a canyon;
wherein the internal network comprises a three-fold axis, a five-fold axis and/or a tube below the five-fold axis, and wherein said at least one further modification is located at or in close proximity to said three-fold axis, five-fold axis or tube below the five-fold axis.

7. The poliovirus-like particle (VLP) of claim 5, wherein said one or more additional modification within one or more of the pocket domain, the protomer interface and/or the pentamer is selected from the group consisting of:
(a) a pocket domain serotype 1 capsid stabilising modification selected from the group consisting of: V1196L; and/or
(b) a pocket domain serotype 2 capsid stabilising modification selected from the group consisting of: Y1159F, V1183L and I1194V; and/or
(c) a pocket domain serotype 3 capsid stabilising modification selected from the group consisting of: M1260I; and/or
(d) a protomer interface serotype 1 capsid stabilising modification selected from the group consisting of: T3108A, K1101E, E1168K, A1231V, A1231T, A1232V, D1236Y and D1247Y; and/or
(e) a protomer interface serotype 2 capsid stabilising modification selected from the group consisting of S2139L, T3108A, A3141G, T3175A, I3180T, F3184Y, T3229P, T1030S, T1041I, I1067L, 1104L deletion, V1107I, I1160V, S1179C, V1199M, S1222P, T1223S, A1231V, A1232V and L1234M; and/or
(f) a protomer interface serotype 3 capsid stabilising modification selected from the group consisting of: F3091S, I3190V, I1075V, I1181L, L1199I and I1155M; and/or
(g) a pentamer interface serotype 1 capsid stabilising modification selected from the group consisting of: L2014M, D2067N, L2251V, T2252S, E1040K, I1041V and K1218R; and/or
(h) a pentamer interface of serotype 2 capsid stabilising modification selected from the group consisting of: V2013L, I2014M, D2057E, D2057A, D2057N, I2246L, T2251S, N3073H, L3085F, A3141G and K1039R; and/or
(i) a pentamer interface serotype 3 capsid stabilising modification selected from the group consisting of: L2016I, I3190V and A1034V.

8. The poliovirus-like particle (VLP) of claim 5, wherein said one further modification in one or more additional structural domain is selected from the group consisting of:
(a) a VP2/VP3 interface serotype 1 capsid stabilising modification selected from the group consisting of: S1295P and I2197V; and/or
(b) an internal network serotype 1 capsid stabilising modification selected from the group consisting of: N4017T, S4023Y, F4046L, E4055Q and M1009V; and/or
(c) a canyon serotype 1 capsid stabilising modification selected from the group consisting of: M1090L and K1252T; and/or
(d) a VP1/VP2 interface serotype 1 capsid stabilising modification selected from the group consisting of: V2127I; and/or
(e) an other serotype 1 capsid stabilising modification selected from the group consisting of: A3059D, G2159S, S2168A and G2228V; and/or
(f) a VP2/VP3 interface serotype 2 capsid stabilising modification selected from the group consisting of: I2191V; and/or
(g) an internal network serotype 2 capsid stabilising modification selected from the group consisting of: E4055A, E4055Q, I4057L, I4057V, V2033I, Q3161E and L1021P; and/or
(h) a canyon serotype 2 capsid stabilising modification selected from the group consisting of: M2140T; and/or
(i) an other serotype 2 capsid stabilising modification selected from the group consisting of: T2161S, R3094K and R1100C; and/or
(j) an internal network serotype 3 capsid stabilising modification selected from the group consisting of: E4055Q, M2124I, A1054V, A1054T, V1265I and I1075V; and/or
(k) an external (protomer near interface) serotype 3 capsid stabilising modification selected from the group consisting of: K2269R.

9. The poliovirus-like particle (VLP) of claim 1, which is:
(a) a type 1 VLP derived from a type 1 poliovirus with (i) a P1 having an amino acid sequence of SEQ ID NO: 16 or 17; (ii) a VP1 having an amino acid sequence of SEQ ID NO: 1, a VP0 having an amino acid sequence of SEQ ID NO: 5, and a VP3 having an amino acid sequence of SEQ ID NO: 3, (iii) a VP1 having an amino acid sequence of SEQ ID NO: 1, a VP2 having an amino acid sequence of SEQ ID NO: 2, and a VP3 having an amino acid sequence of SEQ ID NO: 3 and a VP4 having an amino acid sequence of SEQ ID NO: 4; and/or (iv) a P1; VP1, VP0 and VP3; or a VP1, VP2, VP3 and VP4 having an amino acid sequence with at least 90% sequence identity to the amino acid sequences of (i) to (iii);
(b) a type 2 VLP derived from a type 2 poliovirus with (i) a P1 having an amino acid sequence of SEQ ID NO: 18 or 19; (ii) a VP1 having an amino acid sequence of SEQ ID NO: 6, a VP0 having an amino acid sequence of SEQ ID NO: 10, and a VP3 having an amino acid sequence of SEQ ID NO: 8, (iii) a VP1 having an amino acid sequence of SEQ ID NO: 6, a VP2 having an amino acid sequence of SEQ ID NO: 7, and a VP3 having an amino acid sequence of SEQ ID NO: 8 and a VP4 having an amino acid sequence of SEQ ID NO: 9; and/or (iv) a P1; VP1, VP0 and VP3; or a VP1, VP2, VP3 and VP4 having an amino acid sequence with at least 90% sequence identity to the amino acid sequences of (i) to (iii); or
(c) a type 3 VLP derived from a type 3 poliovirus with (i) a P1 having an amino acid sequence of SEQ ID NO: 20 or 21; (ii) a VP1 having an amino acid sequence of SEQ ID NO: 11, a VP0 having an amino acid sequence of SEQ ID NO: 15, and a VP3 having an amino acid sequence of SEQ ID NO: 13, (iii) a VP1 having an amino acid sequence of SEQ ID NO: 11, a VP2 having an amino acid sequence of SEQ ID NO: 12, and a VP3 having an amino acid sequence of SEQ ID NO: 13 and a VP4 having an amino acid sequence of SEQ ID NO: 14; and/or (iv) a P1; VP1, VP0 and VP3; or a VP1, VP2, VP3 and VP4 having an amino acid sequence with at least 90% sequence identity to the amino acid sequences of (i) to (iii).

10. A composition comprising the poliovirus-like particle (VLP) of claim 1 and a pharmaceutically acceptable excipient, diluent or adjuvant.

11. A method of vaccinating a subject against poliovirus, the method comprising administering to a subject in need thereof an effective amount of the poliovirus-like particle (VLP) of claim 1.

* * * * *